United States Patent [19]

Teutsch et al.

[11] Patent Number: 4,547,493
[45] Date of Patent: * Oct. 15, 1985

[54] NOVEL 11β-SUBSTITUTED-19-NOR-STEROIDS

[75] Inventors: Jean-Georges Teutsch, Pantin; Vesperto Torelli, Maisons-Alfort; Roger Deraedt, Pavillons-sous-Bois; Daniel Philibert, La Varenne-Saint-Hilaire, all of France

[73] Assignee: Roussel Uclaf, Paris, France

[*] Notice: The portion of the term of this patent subsequent to May 31, 2000 has been disclaimed.

[21] Appl. No.: 501,373

[22] Filed: Jun. 6, 1983

[30] Foreign Application Priority Data

Jun. 11, 1982 [FR] France .................. 82 10205

[51] Int. Cl.[4] .................. C07J 1/00; A61K 31/56
[52] U.S. Cl. .................. 514/179; 260/397.45
[58] Field of Search .................. 424/243, 238; 260/397.45; 514/180, 179

[56] References Cited

U.S. PATENT DOCUMENTS 4,292,251  9/1981  Overpeek .................. 260/397.45
4,386,085  5/1983  Teutsch .................. 260/397.45

Primary Examiner—Elbert L. Roberts
Attorney, Agent, or Firm—Charles A. Muserlian

[57] ABSTRACT

Novel 19-nor-steroids of the formula

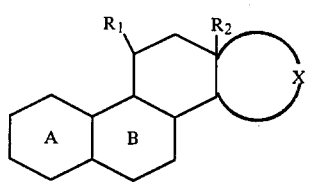

wherein $R_1$ is an organic group of 1 to 18 carbon atoms optionally containing at least one heteroatom with the atom immediately adjacent the 11-carbon atom being carbon, $R_2$ is a hydrocarbon of 1 to 8 carbon atoms, X is the remainder of a pentagonal or hexagonal ring optionally substituted and optionally containing one unsaturated bond, the A and B rings are selected from the group consisting of

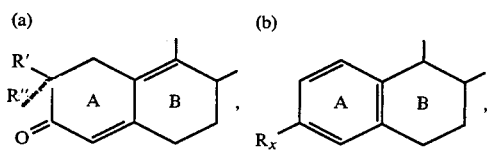

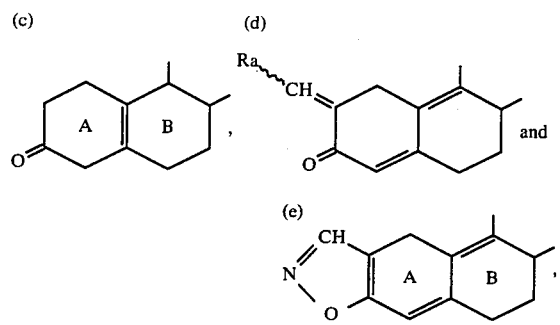

$R'$ and $R''$ are individually selected from the group consisting of hydrogen, —CN and alkyl of 1 to 4 carbon atoms with at least one being other than hydrogen, $R_x$ is selected from the group consisting of hydrogen and $OR_c$, $R_c$ is selected from the group consisting of hydrogen, optionally substituted alkyl of 1 to 6 carbon atoms and acyl, $R_a$ may be in the E or Z positions as indicated by the wavy line and is selected from the group consisting of

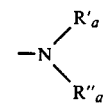

and acyloxy, $R_a'$ and $R_a''$ are alkyl of 1 to 4 carbon atoms or taken together with the nitrogen atom form a heterocycle of 5 to 6 chain members optionally containing another heteroatom with the proviso that when A and B are

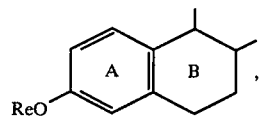

$R_1$ contains at least one nitrogen, phosphorus or silicium atom and when A and B are

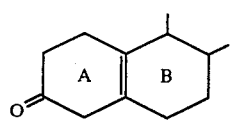

$R_1$ is not a linear alkyl and their non-toxic, pharmaceutically acceptable acid addition salts having a remarkable antigluococorticoid activity, their preparation and novel intermediates.

44 Claims, No Drawings

NOVEL 11β-SUBSTITUTED-19-NOR-STEROIDS

STATE OF THE ART

Commonly assigned U.S. Pat. No. 4,272,530 and co-pending U.S. patent applications Ser. No. 469,042 filed Feb. 23, 1983 now U.S. Pat. No. 4,477,445 and Ser. No. 386,967 filed June 10, 1982 now U.S. Pat. No. 4,447,424 describe related steroids of different structures.

OBJECTS OF THE INVENTION

It is an object of the invention to provide the novel compounds of formula I and their non-toxic, pharmaceutically acceptable acid addition salts and a novel process for their preparation and novel intermediates.

It is another object of the invention to provide novel antiglucocorticoid composition and a novel method of inducing antiglucocorticoidal activity in warm-blooded animals.

These and other objects and advantages of the invention will become obvious from the following detailed description.

THE INVENTION

The novel compounds of the invention are selected from the group consisting of 19-nor-steroids of the formula

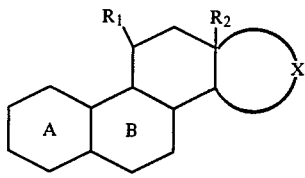

I wherein $R_1$ is an organic group of 1 to 18 carbon atoms optionally containing at least one heteroatom with the atom immediately adjacent the 11-carbon atom being carbon, $R_2$ is a hydrocarbon of 1 to 8 carbon atoms, X is the remainder of a pentagonal or hexagonal ring optionally substituted and optionally containing one unsaturated ═ bond, the A and B rings are selected from the group consisting of

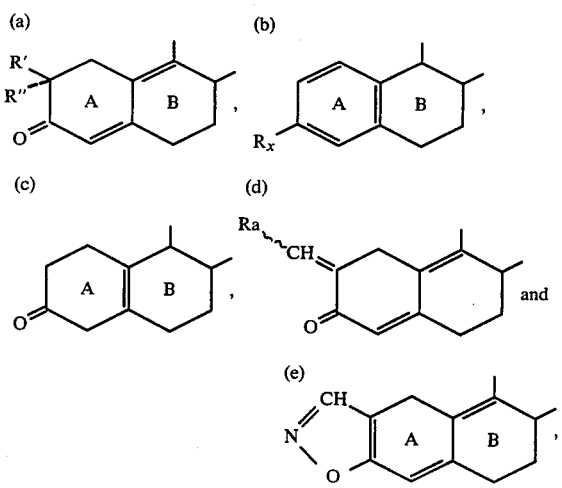

R' and R" are individually selected from the group consisting of hydrogen, —CN and alkyl of 1 to 4 carbon atoms with at least one being other than hydrogen, $R_x$ is selected from the group consisting of hydrogen and $OR_3$, $R_e$ is selected from the group consisting of hydrogen, optionally substituted alkyl of 1 to 6 carbon atoms and acyl, $R_a$ may be in the E or Z positions as indicated by the wavy line and is selected from the group consisting of

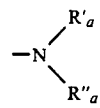

and acyloxy, $R_a'$ and $R_a''$ are alkyl of 1 to 4 carbon atoms or taken together with the nitrogen atom form a heterocycle of 5 to 6 chain members optionally containing another heteroatom with the proviso that when A and B are

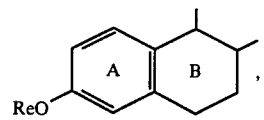

$R_1$ contain at least one nitrogen, phosphorus or silicium atom and when A and B are

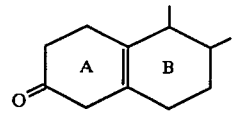

$R_1$ is not a linear alkyl and their non-toxic, pharmaceutically acceptable acid addition salts.

$R_1$ is preferably an optionally unsaturated alkyl of 1 to 12 carbon atoms such as methyl, ethyl, isopropyl, propyl, butyl, isobutyl, tert.-butyl, n-pentyl, n-hexyl, 2-methyl-pentyl, 2,3-dimethyl-pentyl, n-heptyl, 2-methyl-hexyl-, 2,2-dimethylpentyl, 3,3-dimethyl-pentyl, 3-ethyl-pentyl, n-octyl, 2,2-dimethyl-hexyl, 3,3-dimethyl-hexyl, 3-methyl-3-ethylpentyl, nonyl, 2,4-dimethyl-heptyl, n-decyl, vinyl, isopropenyl, allyl, 2-methyl-allyl and isobutenyl.

Examples of suitable optional substituents are thioalkyl such as thiomethyl or thioethyl and $R_1$ may be substituted with at least one halogen such as fluorine, chlorine, bromine, iodine; substituted amino such as dimethylamino, $R_1$ may also be aryl or aralkyl, especially phenyl or benzyl and the aromatic rings may be substituted in the p-, o- or m-positions with at least one member of the group consisting of alkyl of 1 to 4 carbon atoms, alkoxy of 1 to 4 carbon atoms such as methoxy, ethoxy, propoxy, isopropoxy, butoxy, isobutoxy and tert.-butoxy; alkenyloxy of 2 to 4 carbon atoms such as allyloxy or vinyloxy; halogen such as chlorine or fluorine; —OH; —CF$_3$; alkylthio of 1 to 4 carbon atoms such as methylthio or ethylthio which may be oxidized to sulfoxide or sulfone or a combination thereof such as 3-fluoro-4-dimethylamino-phenyl.

$R_1$ may also be an aryl heterocycle optionally substituted such as thienyl, furyl, isothienyl, isofuryl, thiazolyl, isothiazolyl, oxazolyl, isoxazolyl, thiadiazolyl, pyridinyl, piperidinyl and other heterocycles known to those skilled in the art.

$R_1$ may also be cycloalkyl such as cyclopropyl, cyclobutyl, cyclopentyl or cyclohexyl; cycloalkenyl such as cyclobutenyl or cyclopropenyl; aryl substituted with a member of the group consisting of amino optionally substituted with one or 2 alkyls of 1 to 8 carbon atoms, nitrogen heterocycle group optionally containing a second oxygen, sulfur or nitrogen heteroatom such as morpholino or piperidinyl, substituted aminoalkyl or alkoxy such as dimethylaminomethyl, dimethylaminoethyl or dimethylaminoethoxy or a silicum group such as trimethylsilylphenyl. The preferred aryl is phenyl and the substituent may also be a nitrogen atom which can be oxidized. The preferred heteroatom of $R_1$ is sulfur or nitrogen.

$R_2$ is preferably substituted alkyl of 1 to 4 carbon atoms such as methyl, ethyl, propyl, isopropyl or butyl and preferably methyl or ethyl and most preferably methyl. X is preferably an optionally substituted pentagonal ring and R' and R" are alkyl as discussed above. When Re is a substituted alkyl, it is preferably substituted with a dialkylamino such as dimethylamino, diethylamino or methyl ethylamino. When Ra is

it is preferably an dialkylamino such as dimethylamino, diethylamino or methylethylamino, it also is pyrrolidino, piperidino or morpholino.

$R_a$ may also be alkanoyloxy such as acetyloxy, propionyloxy and their higher homologs or arylcarbonyloxy such as benzoyloxy.

Examples of suitable acids for the preparation of the non-toxic, pharmaceutically acceptable acid addition salts are mineral acids such as hydrochloric acid, hydrobromic acid, nitric acid, sulfuric acid and phosphoric acid and organic acids such as formic acid, acetic acid, propionic acid, benzoic acid, maleic acid, fumaric acid, succinic acid, tartaric acid, citric acid, oxalic acid, glyoxylic acid, aspartic acid, alkane sulfonic acids such as methane sulfonic acid and ethane sulfonic acid, arylsulfonic acids such as benzene sulfonic acid and p-toluene sulfonic acid and arylcarboxylic acids.

Among the preferred compounds of formula I are those wherein X is a ring of the formula

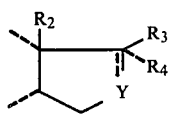

wherein $R_2$ has the above definition, the dotted line in the 16,17-position indicates an optional double bond, Y is

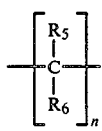

n is 1 or 2, $R_5$ is selected from the group consisting of hydrogen, alkyl of 1 to 8 carbon atoms, alkenyl and alkynyl of 2 to 8 carbon atoms, aryl of 6 to 14 carbon atoms and aralkyl of 7 to 15 carbon atoms, $R_6$ is selected from the group consisting of hydrogen, —OH, alkyl of 1 to 8 carbon atoms, alkenyl and alkynyl of 2 to 8 carbon atoms, aryl of 6 to 14 carbon atoms and aralkyl of 7 to 15 carbon atoms and $R_3$ and $R_4$ are individually selected from the group consisting of hydrogen, —OH, —OAlK$_4$,

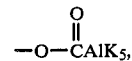

alkenyl and alkynyl of 2 to 8 carbon atoms,

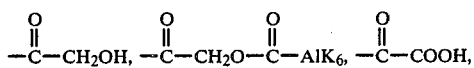

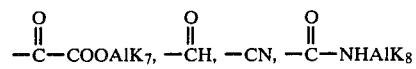

or $R_3$ and $R_4$ together with the carbon atoms are

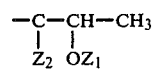

or

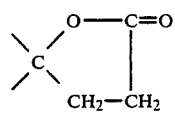

AlK$_4$, AlK$_5$ and AlK$_8$ are selected from the group consisting of alkyl of 1 to 8 carbon atoms and aralkyl of 7 to 15 carbon atoms, Alk$_6$ are selected from the group consisting of alkyl of 1 to 8 carbon atoms optionally substituted and aralkyl of 7 to 15 carbon atoms, alk$_7$ and Z$_2$ are alkyl of 1 to 8 carbon atoms and Z$_1$ is selected from the group consisting of hydrogen, alkyl of 1 to 8 carbon atoms and acyl of 1 to 8 carbon atoms.

Examples of preferred examples of $R_5$ or $R_6$ are methyl, ethyl, vinyl, isopropenyl, allyl, ethynyl, propynyl, phenyl and benzyl. Preferred examples of $R_3$ and $R_4$ are —OAlK$_4$ and

wherein AlK$_4$ and AlK$_5$ are methyl, ethyl, n-propyl, butyl, pentyl, hexyl or benzyl or are vinyl, isopropenyl, allyl, 2-methylallyl, —C≡CH, —C≡CAlK$_9$ wherein AlK$_9$ is methyl, ethyl, n-propyl, isopropyl, isopropenyl, butyl, benzyl or CF$_3$—AlK$_6$, AlK$_7$ and AlK$_8$ have the same preferred values as AlK$_4$ and AlK$_5$. The preferred compounds are those in which $R_3$ and $R_4$ are different except if one is hydrogen.

Among preferred values of

are the groups

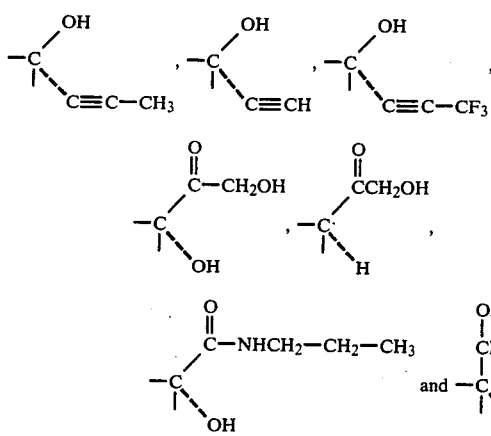

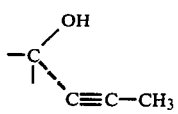

wherein $Z_1$ is hydrogen, alkyl of 1 to 8 carbon atoms or acyl of 2 to 8 carbon atoms such as acetyloxy or benzoyl and $Z_2$ is alkyl of 1 to 8 carbon atoms such as methyl. More preferable is the group

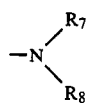

The D ring of the compounds of formula I is preferably not unsaturated, n is 1 and $R_5$ and $R_6$ are hydrogen. Another preferred group of compounds are those of formula I wherein $R_3$ is —OH or $$-O\overset{O}{\underset{\|}{C}}AlK_5$$

and $R_4$ is alkenyl or alkynyl of 2 to 4 carbon atoms.

Among the preferred compounds of formula I are those wherein $R_1$ is a hydrocarbon of 1 to 18 carbon atoms containing at least one nitrogen atom and especially primary, secondary or tertiary alkyl of 1 to 8 carbon atoms containing at least one heteroatom selected from the group consisting of oxygen, nitrogen and sulfur, at least one being nitrogen or substituted with a heterocycle containing at least one nitrogen atom. The hydrocarbon may be alkyl such as methyl, ethyl, n-propyl, isopropyl, butyl, isobutyl, tert.-butyl, pentyl, hexyl or cycloalkyl such as cyclopropyl, cyclobutyl, cyclopentyl or cyclohexyl. The heterocycle containing at least one nitrogen is preferably 2-pyridyl, 3-pyridyl, 4-pyridyl, thiazolyl or piperidinyl.

Another preferred groups of compounds of the invention are those wherein $R_1$ is a heterocycle containing at least one nitrogen atom optionally substituted with alkyl of 1 to 8 carbon atoms such as 2-pyridyl, 3-pyridyl, 4-pyridyl, thiazolyl or piperidinyl and the alkyl substituent is preferably methyl, ethyl or n-propyl.

$R_1$ may also preferably be aryl or aralkyl carrying an amino of the formula $$-N\begin{matrix}R_7\\ \diagdown\\ R_8\end{matrix}$$

wherein $R_7$ and $R_8$ are alkyl of 1 to 8 carbon atoms or primary, secondary or tertiary alkyl of 1 to 8 carbon atoms containing at least one heteroatom of the group consisting of —O—, —S— or —N— with at least one being nitrogen or substituted with a heterocycle containing at least one nitrogen atom. The alkyl, aryl, aralkyl and heterocycles are those discussed above.

Especially preferred are compounds of formula I wherein $R_1$ is selected from the group consisting of 2-pyridyl, 3-pyridyl, 4-pyridyl,

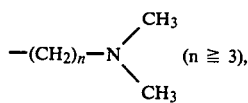

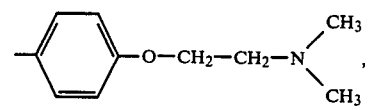

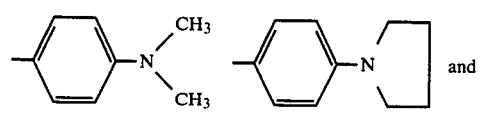

 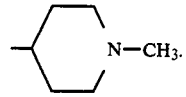

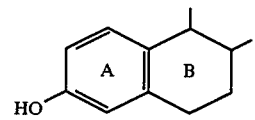

Another preferred group of compounds of formula I are those wherein $R_1$ is selected from the group consisting of thienyl, furyl, cycloalkyl of 3 to 6 carbon atoms and phenyl optionally substituted with at least one member of the group consisting of —OH, halogen, —CF_3, alkyl and alkoxy of 1 to 8 carbon atoms and alkylthio of 1 to 8 carbon atoms optionally oxidized to sulfoxide or sulfone and A and B rings are not

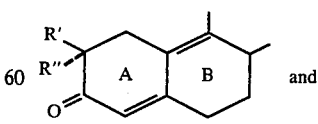

The preferred substituents are those listed above and among the more preferred values of $R_1$ are phenyl substituted with a member of the group consisting of chlorine, fluorine, methylthio, methylsulfonyl, methoxy, —OH and allyloxy.

Equally preferred compounds of formula I are those wherein the A and B rings are selected from the group consisting of

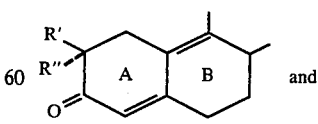 and

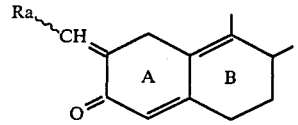

wherein Ra is morpholino or acetyloxy and R' and R"
are both methyl or both —CN or one is hydrogen and
the other is methyl or —CN.

Specific preferred compounds of formula I are 2,2-dimethyl-11β-(4-dimethylaminophenyl)-17α-(prop-1-ynyl)-Δ$^{4,9}$-estradiene-17β-ol-3-one, 2,2-dicyano-11β-(4-dimethylaminophenyl)-17α-(prop-1-ynyl)-Δ$^{4,9}$-estradiene-17β-ol-3-one, 2α-methyl-11β-(4-dimethylaminophenyl)-17α-(prop-1-ynyl)-Δ$^{4,9}$-estradiene-17β-ol-3-one, 2β-methyl-11β-(4-dimethylaminophenyl)-17α-(prop-1-ynyl)-Δ$^{4,9}$-estradiene-17β-ol-3-one, 2-cyano-11β-(4-dimethylaminophenyl)-17α-(prop-1-ynyl)-Δ$^{4,9}$-estradiene-17β-ol-3-one, 11β-(4-dimethylamino)-17α-(prop-1-ynyl)-Δ$^{1,3,5(10)}$-estratriene-3,17β-diol, 11β-(4-dimethylaminophenyl)-17β-acetoxy-17α-(prop-1-ynyl)-Δ$^{1,3,5(10)}$-estratriene-3-ol, 3-methoxy-11β-(4-dimethylaminophenyl)-17α-(prop-1-ynyl)-Δ$^{1,3,5(10)}$-estratriene-17β-ol-, 3-methoxy-11β-(4-dimethylaminophenyl)-17β-acetoxy-17α-(prop-1-ynyl)-Δ$^{1,3,5(10)}$-estratriene, 11β-(3-methoxyphenyl)-17α-(prop-1-ynyl)-Δ$^{5(10)}$-estrene-17β-ol-3-ne, (E)11β-(3-methoxyphenyl)-17α-(prop-1-enyl)-Δ$^{5(10)}$-estrene-17β-ol-3-one, 11β-(4-dimethylaminophenyl)-17α-(prop-1-ynyl)-Δ$^{5(10)}$,-estrene-17β-ol-3-one, 2-(acetyloxymethylene)-11β-(4-dimethylaminophenyl)-17β-(prop-1-ynyl)-Δ$^{4,9}$-estradiene-17β-ol-3one, 2-(4-morpholinomethylene)-11β-(4-dimethylaminophenyl)-17α-(prop-1-ynyl)-Δ$^{4,9}$-estradiene-17β-ol-3-one, 11β-(4-dimethylaminophenyl)-17α-(prop-1-ynyl)-isozazolo[4,5-b]-Δ$^{4,9}$-estradiene-17β-ol, 11β-[4-(2-dimethylaminoethoxy)-phenyl]-Δ$^{1,3,5(10)}$-estratriene-3,17β-diol, 11β-[4-(2-dimethylaminoethoxy)-phenyl]-Δ$^{1,3,5(10)}$-estradiene-17β-ol, 3-(2-dimethylaminoethoxy)-11β-phenyl-Δ$^{1,3,5(10)}$-estratriene-17β-ol and their non-toxic, pharmaceutically acceptable acid addition salts.

The novel process of the invention for the preparation of the compounds of the formula

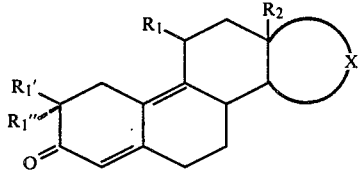

wherein $R_1$, $R_2$ and X have the above definition and $R_1'$ and $R_1''$ are each alkyl or one is hydrogen and the other is alkyl or each are —CN or one is alkyl and the other is —CN comprises reacting a compound of the formula

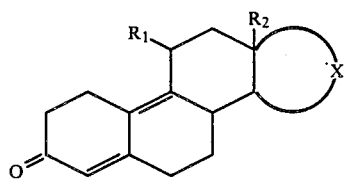

wherein $R_1$, $R_2$ and X have the above definitions after optionally reacting the same with a protective agent for functional groups with a strong base and/or an alkyl halide or tosyl cyanide or with an alkyl halide and then tosyl cyanide, followed by removal of any protective groups, if necessary.

The process for the preparation of compounds of the formula

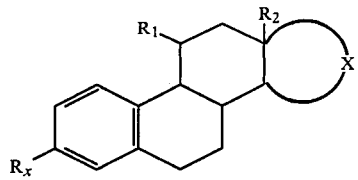

corresponding to the formula

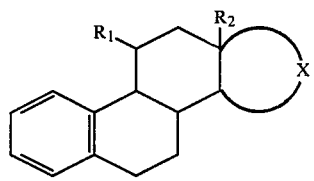

comprises reacting a compound of formula II with a reducing agent to obtain a compound of the formula

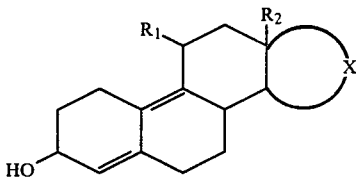

and reacting the latter with an aromatization acid agent to obtain the compound of formula $I_B$.

The process for the preparation of compounds of the formula

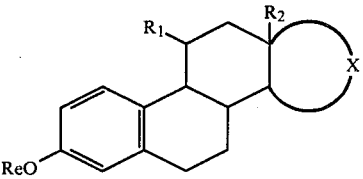

wherein Re, $R_1$, $R_2$ and X have the above definitions comprises reacting a compound of formula II with an aromatization agent which is then saponified and optionally reacted with an alkylation agent or an acylation agent.

The process for the preparation of a compound of the formula

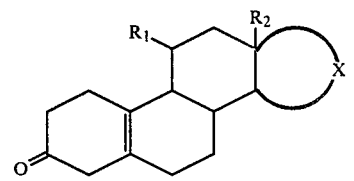

wherein $R_1$, $R_2$ and X have the above definitions comprises reacting a compound of formula II with a reducing agent.

The process for the preparation of a compound of the formula

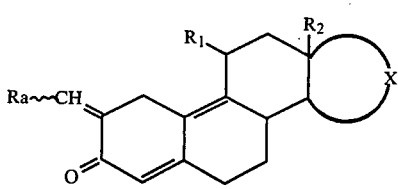

wherein Ra, R₁, R₂ and X have the above definitions comprises reacting a compound of formula II with a formylation agent to obtain a compound of the formula

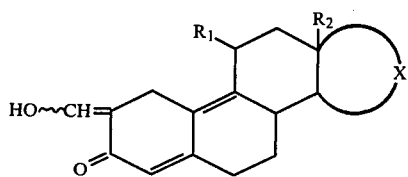

and reacting the latter with an acylation agent or an amine of the formula

wherein $R_a'$ and $R_a''$ have the above definitions.

The process for the preparation of a compound of the formula

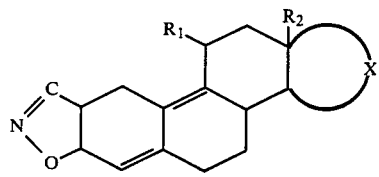

wherein R₁, R₂ and X have the above definitions comprises reacting a compound of formula III with hydroxylamine.

The process for the preparation of a compound of the formula

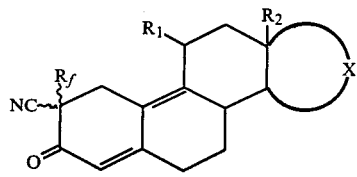

wherein R₁,R₂ and X have the above definitions and $R_f$ is hydrogen or alkyl comprises reacting a compound of formula $I_E$ with a base to obtain the compound of formula $I_A'$ wherein $R_f$ is hydrogen and if desired, reacting the latter with a strong base and an alkyl halide to obtain the compound of formula $I_A'$ wherein $R_f$ is alkyl.

When the compounds of formula II contain one or more groups capable of reacting with a reactant such as alkyl halide, the groups preferably are protected with a group known in the literature. This is particularly important when the group

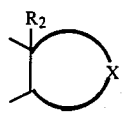

contains a 17β-ol and this group is preferably protected by tetrahydropyranyl by reacting the compound of formula II with dihydropyran.

The strong bases used are preferably alkali metal alcoholates such as potassium tert.-butylate but equally useful are alkali metal amides such as sodium amide or lithium amide prepared in situ. The alkyle halide is preferably an iodide such as methyl iodide and if gem dialkylation in the 2-positions is desired, at least two equivalents of the strong base are used and the reaction is effected in an excess of alkyl iodide. Monoalkylation is obtained when only one equivalent of the strong base is used. Generally, the α- and β-isomers may be separated by conventional techniques such as chromatography.

The addition of two cyano groups in the 2-position is effected with tosyl cyanide whose preparation is described in Chem. Com., 1968, p. 440 and is used as in Tetrahedron Letters No. 50 (1981), p. 5011. The addition of an alkyl halide and then tosyl cyanide yields the compounds wherein one of $R_1'$ and $R_1''$ is alkyl and the other is —CN and may be effected under the preceding conditions.

The eventual removal of the protective groups may be effected by the classical methods for instance, acid hydrolysis, preferably hydrochloric acid may be used to remove the tetrahydropyranyl group.

The reducing agent to prepare the compound of formula II₁ is preferably an alkali metal borohydride such as sodium borohydride and the reaction is preferably effected in an alkanol such as methanol or ethanol. The aromatization agent for the preparation of compounds of formula $I_{B1}$ is preferably a mineral acid such as hydrochloric acid or sulfuric acid or an agent such as phosphorus pentachloride, phosphorus tribromide or phosphorus oxychloride or an anhydride such as acetic anhydride or trifluoroacetic anhydride. The aromatization agent for the preparation of compounds of formula $I_{B2}$ is preferably an acyl halide such as acetyl bromide or acetic anhydride or a mixture thereof.

The preferred saponification agent is an alkali metal base such as sodium hydroxide or potassium hydroxide, sodium amide, potassium tert.-butylate or lithium acetylide in ethylenediamine. The reaction is preferably effected in a lower alkanol such as methanol or ethanol.

Depending on the conditions used and for example if the compound contains a group such as

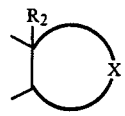

with a reactive group like 17β-ol, a partial acetylation of this group will occur resulting in 17β-ol product containing a variable percentage of 17β-acetyloxy product and the two can be separated by the usual methods such as chromatography. When the starting compound of formula II contains a 17-one group in the pentagonal ring, it can be reduced with sodium borohydride for example.

The eventual alkylation can be effected by usual methods and the preferred alkylating agent is an alkyl halide such as alkyl iodide or an alkylsulfate, preferably methyl sulfate. The acylation may also be effected by known methods and is usually effected with an acyl halide. The reducing agent used to form the compounds of formula $I_C$ are preferably an alkali metal in liquid ammonia, preferably lithium but sodium is also useful.

Depending upon the amount of metal used, other portions of the molecule may be effected and for example, this is the case when the compound has the group

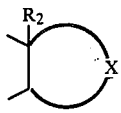

containing a 17α-acetylenic group such as propynyl. The use of two moles of alkali metal results in a practically selective reduction of a 3-keto-$\Delta^{4,9}$-steroid into a 3-keto-$\Delta^{5(10)}$-steroid. If a supplemental amount of reducing agent is used, there is simultaneously obtained a reduction of an acetylenic group into a trans olefin group, i.e. a 17-prop-1-ynyl into a 17α-prop-1-enyl. The separation of the two products may be effected by classical methods such as chromatography.

The formylation of the compounds of formula II is effected under known conditions such as by reaction with a formate such as alkyl formates, i.e. ethyl formate, in the presence of a strong base such as sodium hydride and the acylation of the compound of formula III is effected under known conditions as well. Preferably, the acylating agent is an acid anhydride oracid halide such as acetyl chloride and the reaction is effected in the presence of an acid receptor such as pyridine.

The reaction with an amine of the formula

is effected under known conditions, preferably with heating. The reaction of the compound of formula III with hydroxylamine which is preferably in the form of an acid salt such as its hydrochloride is effected in a refluxing alkanol such as tert.-butanol. The hydrolysis of the compounds of formula $I_E$ is preferably effected with a base such as sodium hydroxide or potassium hydroxide, preferably in methanol. The alkylation of the compounds of formula $I_4'$ when $R_f$ is hydrogen is effected under the usual conditions indicated above.

In a preferred mode of the process of the invention, the starting materials of formula II have the group

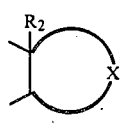

which is

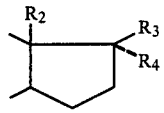

wherein $R_2$ is methyl, $R_3$ is —OH or

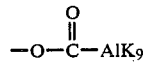

and $AlK_9$ is alkyl of 1 to 4 carbon atoms, $R_4$ is alkenyl or alkynyl of 2 to 4 carbon atoms and $R_1$ is

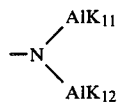

or alkoxyphenyl wherein the alkyl has 1 to 4 carbon atoms and $Alk_{11}$ and $AlK_{12}$ are alkyl of 1 to 4 carbon atoms.

The novel antiglucocorticoid compositions of the invention are comprised of an antiglucocorticoidally effective amount of at least one compound of formula I and its non-toxic, pharmaceutically acceptable acid addition salts and an inert pharmaceutical carrier. The compositions may be in the form of tablets, dragees, gelules, granules, suppositories, ovules, injetable solutions or suspensions, pommades, creams and gels prepared in the usual fashion.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants and emulsifiers and preservatives.

The compositions are useful to principally counter effect secondary effects of glucocorticoids and are useful for the treatment of troubles due to a hypersecretion of glucocorticoids, especially against aging in general and especially against hypertension, atherosclerosis, osteoporosis, diabetics, obesity as well as immuno-suppressive effects and insomnia.

The study of the products on hormonal receptors shows that they possess progestomimetic or antiprogestomimetic activity or androgen or antiandrogen activity. The compounds of formula I which possess antiprogestomimetic activity are useful as original contraceptives or as interruption of pregnancy agents. They may also be useful for inducing regular cycles in females and more generally in warm-blooded females.

The products may be administered during periods or when progesterone discharges an essential physiological role which is notably during the luteal phase of the cycle at the moment of nidation or implantation of the embryo and during the pregnancy. One method of contraception of the invention consists of administering to the female at least one of the products of formula I or its salts 1 to 5 days before the end of the cycle. The products are preferably administered orally or in the vagina but may also be administered parenterally or endonasally.

The compounds of formula I possessing antiprogestomimetic activity are equally useful against hormonal irregularities and by other means they present an interest in the treatment of hormonodependent tumors. Their action against hypophysial secretions make the compounds useful in menopause.

The compounds are equally useful for the synchronization of estrus in larger animals such as bovines and sheep and are useful for controlling the fertility of household pets such as cats and dogs.

Certain compounds of formula I also present progestomimetic properties and are useful for the treatment of amenorrhea, of dysmenorrhea and luteal insufficiencies.

The compounds of formula I possessing antiandrogenic activity are useful in the treatment of hypertrophies and prostate cancer, or hyperandrogenia, of anemia, hirsutism and of acne as well as male contraception.

Certain of the compounds of formula I possess estrogenic properties and are useful for the treatment of troubles due to a hypofolliculinia such as amenorrhea, dysmenorrhea, repeated abortions, premenstrual troubles as well as for the treatment of menopause.

Certain of the compounds of formula I possess antiestrogenic properties and are useful for the treatment of mammalogy carcinoma and its meta stases.

Among the preferred compositions of the invention ae those wherein the active ingredient is selected from the group consisting of 2,2-dimethyl-11$\beta$-(4-dimethylaminophenyl)-17$\alpha$-(prop-1-ynyl)-$\Delta^{4,9}$-estradiene-17$\beta$-ol-3-one, 2,2-dicyano-11$\beta$-(4-dimethylaminophenyl)-17$\alpha$-(prop-1-ynyl)-$\Delta^{4,9}$-estradiene-17$\beta$-ol3-one, 2$\alpha$-methyl-11$\beta$-(4-dimethylaminophenyl)-17$\alpha$-(prop-1-ynyl)-$\Delta^{4,9}$-estradiene-17$\beta$-ol-3-one, 2$\beta$-methyl-11$\beta$-(4-dimethylaminophenyl)-17$\alpha$-(prop-1-ynyl)-$\Delta^{4,9}$-estradiene-17$\beta$-ol-3-one, 2-cyano-11$\beta$-(4-dimethylaminophenyl)-17$\alpha$-(prop-1-ynyl)-$\Delta^{4,9}$-estradiene-17$\beta$-ol-3-one, 11$\beta$-(4-dimethylamino)-17$\alpha$-(prop-1-ynyl)-$\Delta^{1,3,5(10)}$-estratriene-3,17$\beta$-diol, 11$\beta$-(4-dimethylaminophenyl)-17$\beta$-acetoxy-17$\alpha$-(prop-1-ynyl)-$\Delta^{1,3,5(10)}$-estratriene-3-ol, 3-methoxy-11$\beta$-(4-dimethylaminophenyl)-17$\alpha$-(prop-1-ynyl)-$\Delta^{1,3,5(10)}$-estratriene-17$\beta$-ol, 3-methoxy-11$\beta$-(4-dimethylaminophenyl)-17$\beta$-acetoxy-17$\alpha$-(prop-1-ynyl)-$\Delta^{1,3,5(10)}$-estratriene, 11$\beta$-(3-methoxyphenyl)-17$\alpha$-(prop-1-ynyl)-$\Delta^{5(10)\text{-}estrene}$-17$\beta$-ol-3-one, (E) 11$\beta$-(3-methoxyphenyl)-17$\alpha$-(prop-1-enyl)-$\Delta^{5(10)}$-estrene-17$\beta$-ol-3-one, 11$\beta$-(4-dimethylaminophenyl)-17$\alpha$-(prop-1-ynyl)-$\Delta^{5(10)}$-estrene-17$\beta$-ol-3-one, 2-(acetyloxymethylene)-11$\beta$-(4-dimethylaminophenyl)-17$\alpha$-(prop-1-ynyl)-$\Delta^{4,9}$-estradiene-17$\beta$-ol-3-one, 2-(4-morpholinomethylene)-11$\beta$-(4-dimethylaminophenyl)-17$\alpha$-(prop-1-ynyl)-$\Delta^{4,9}$-estradiene-17$\beta$-ol-3-one, 11$\beta$-(4-dimethylaminophenyl)-17$\alpha$-(prop-1-ynyl)-isoxazolo[4,5-b]-$\Delta^{4,9}$-estradiene-17$\beta$-ol, 11$\beta$-[4-(2-dimethylaminoethoxy)-phenyl]-$\Delta^{1,3,5(10)}$-estratriene-3,17$\beta$-diol, 11$\beta$-[4-(2-dimethylaminoethoxy)-phenyl]-$\Delta^{1,3,5(10)}$-estratriene-17$\beta$-ol, 3-(2-dimethylaminoethoxy)-11$\beta$-phenyl-$\Delta^{1,3,5(10)}$-estratriene-17$\beta$-ol and their non-toxic, pharmaceutically acceptable acid addition salts.

The novel method of the invention for inducing antiglucocorticoid activity in warm-blooded animals, including humans, comprises administering to warm-blooded animals an antiglucocorticoidally effective amount of at least one compound of formula I and their non-toxic, pharmaceutically acceptable acid addition salts. The compounds may be administered orally, rectally, parenterally or topically and the usual daily dose is 0,15 to 0,150 mg/kg depending upon the compound, the condition treated and the method of treatment.

The novel intermediates of the invention are the compounds of formula III.

The compounds of formula II may be prepared by reacting a compound of the formula

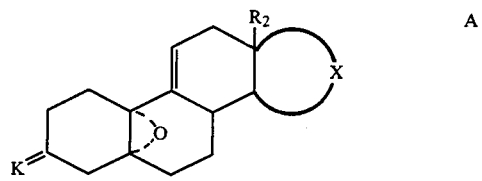

A wherein K is a blocked ketone in the form of a ketal, thioketal, oxime or methyloxime with a compound of the formula $R_1Li$ or $(R_1)_2CuLi$ or $R_1MgHal$ to obtain a compound of the formula

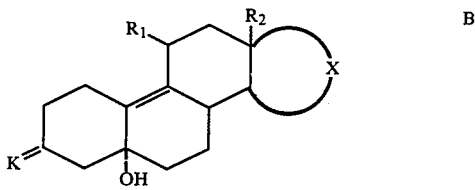

B which is then reacted with a deshydration agent capable of freeing the protected groups to form the compound of formula II. The deshydration agent is preferably a sulfonic acid resin of polystyrene or a mineral acid such as sulfuric acid or hydrochloric acid.

The compounds of formula A can be prepared by reacting a compound of the formula

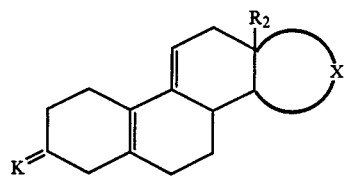

with an oxidizing agent such as hydrogen peroxide in the presence of a catalyst or with a organic peracid.

Examples of compounds of formula I are illustrated in the following tables but are not limited thereto.

| A-B ring | R₁ | R₂ | R₃ | R₄ |
|---|---|---|---|---|
| (6-hydroxy, 1-Me, 2-Me tetralin) | | CH₃ | OH | —C≡C—H |
| (6-hydroxy, 1-Me, 2-Me tetralin) | N-ethyl-N-(p-tolyl)amino | | | |
| " | " | " | " | —C≡C—CF₃ |
| " | " | " | " | —C≡C—CH₂CH₃ |
| " | " | " | " | —CH₂—C≡C—H |
| " | " | " | " | —C≡C—SiMe₃ |
| " | " | " | —C≡C—H | OH |
| " | " | " | —C≡C—SiMe₃ | OH |
| (6-hydroxy, 1-Me, 2-Me tetralin) | N-ethyl-N-(p-tolyl)amino | CH₂CH₃ | OH | —C≡C—H |
| " | " | " | OH | —C≡C—CH₃ |
| " | " | " | OH | —CH₂—C≡C—H |
| " | " | CH₃ | —C(=O)—CH₂OH | H |
| " | " | " | " | OH |
| " | N,N-dimethyl-(p-tolyl)amino | " | OH | —C≡C—H |
| " | " | " | (spiro-γ-butyrolactone at C-R3/R4) | |
| (6-hydroxy, 1-Me, 2-Me tetralin) | N,N-dimethyl-(p-tolyl)amino | " | —C≡C—H | OH |
| " | " | " | OH | —CH₂—C≡C—H |
| " | N,N-dimethyl-(2-fluoro-p-tolyl)amino | " | OH | —C≡C—H |
| " | " | " | " | —C≡C—CH₃ |
| " | " | " | " | —CH₂—C≡C—H |
| " | " | " | —C≡C—H | OH |
| " | 1-methyl-5-indolinyl (N-methylindoline-5-yl) | " | OH | —C≡C—H |

-continued
| | $R_1$ | $R_2$ | $R_3$ | $R_4$ |
|---|---|---|---|---|
| | | " | " | —C≡C—CF₃ |
| 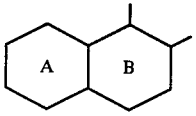 | 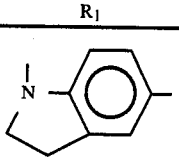 | " | " | |
| " | " | " | " | —CH₂—C≡C—H |
| " | " | " | " | —C≡C—CH₂CH₃ |
| " | " | " | " | —C≡C—Cl |
| " | " | " | " | —C≡C—SiMe₃ |
| " | " | " | —C≡C—H | OH |
| " | " | " | —C≡C—SiMe₃ | OH |
| " | " | " | OH | —C≡C—H |
| 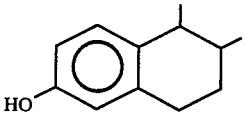 | 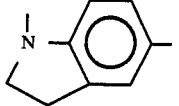 | " | | |
| " | " | " | " | —C≡C—CF₃ |
| " | " | " | " | —C≡C—CH₂CH₃ |
| " | " | " | " | —CH₂—C≡C—H |
| " | " | " | " | —C≡C—SiMe₃ |
| " | " | " | —C≡C—H | OH |
| " | " | " | —C≡C—SiMe₃ | OH |
| 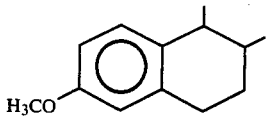 | 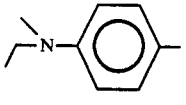 | CH₂CH₃ | OH | —C≡C—H |
| " | " | " | OH | —C≡C—CH₃ |
| " | " | " | OH | —CH₂—C≡C—H |
| " | " | CH₃ | —C(=O)—CH₂OH | H |
| " | " | " | " | OH |
| " | 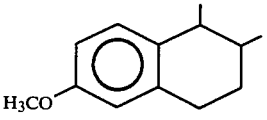 | " | OH | —C≡C—H |
| " | " | " | 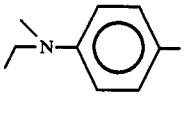 | |
| " | " | " | —C≡C—H | OH |
| 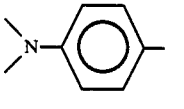 | 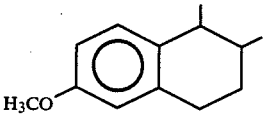 | " | | |
| " | " | " | OH | —CH₂—C≡C—H |
| " | 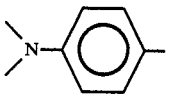 | " | OH | —C≡C—H |
| " | " | " | " | —C≡C—CH₃ |

-continued

| [decalin A-B structure] | R₁ | R₂ | R₃ | R₄ |
|---|---|---|---|---|
| | " | " | " | —CH₂—C≡C—H |
| | " | " | —C≡C—H | OH |
| | " | [N-methyl indoline-methylphenyl] | OH | —C≡C—H |
| [methoxy-tetralin structure] | " | " | " | —C≡C—CF₃ |
| " | " | " | " | —CH₂—C≡C—H |
| " | " | " | " | —C≡C—CH₂CH₃ |
| " | " | " | " | —C≡C—Cl |
| " | " | " | " | —C≡C—SiMe₃ |
| " | " | " | —C≡C—H | OH |
| " | " | " | —C≡C—SiMe₃ | OH |
| " | " | " | OH | —C≡C—H |
| [octahydronaphthalenone structure] | " | [N-ethyl-methylphenyl] | " | " |
| " | " | " | " | —C≡C—CF₃ |
| " | " | " | " | —C≡C—CH₂CH₃ |
| " | " | " | " | —CH₂—C≡C—H |
| " | " | " | " | —C≡C—SiMe₃ |
| " | " | " | —C≡C—H | OH |
| " | " | " | —C≡C—SiMe₃ | OH |
| [octahydronaphthalenone structure] | " | [N-ethyl-methylphenyl] | CH₂CH₃ | OH | —C≡C—H |
| " | " | " | " | OH | —C≡C—CH₃ |
| " | " | " | " | OH | —CH₂—C≡C—H |
| " | " | " | CH₃ | —C(=O)—CH₂OH | H |
| " | " | " | " | " | OH |
| " | " | [N,N-dimethyl-methylphenyl] | " | OH | —C≡C—H |
| " | " | " | " | " | [γ-butyrolactone] |
| [octahydronaphthalenone structure] | " | [N,N-dimethyl-methylphenyl] | " | —C≡C—H | OH |
| " | " | " | " | OH | —CH₂—C≡C—H |

-continued

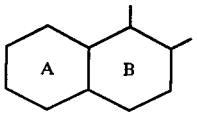

| R₁ | R₂ | R₃ | R₄ |
|---|---|---|---|
| | 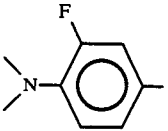 (2-F, N(CH₃)₂ phenyl) | OH | —C≡C—H |
| " | " | " | —C≡C—CH₃ |
| " | " | " | —CH₂—C≡C—H |
| " | " | —C≡C—H | OH |
| " | 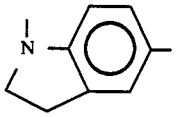 (N-methylindoline) | OH | —C≡C—H |
| 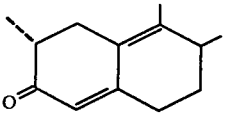 | 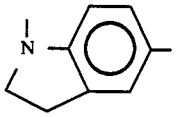 | " | —C≡C—CF₃ |
| " | " | " | —CH₂—C≡C—H |
| " | " | " | —C≡C—CH₂CH₃ |
| " | " | " | —C≡C—Cl |
| " | " | " | —C≡C—SiMe₃ |
| " | " | —C≡C—H | OH |
| " | " | —C≡C—SiMe₃ | OH |
| " | " | OH | —C≡C—H |
| 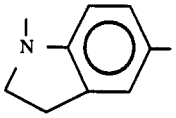 | 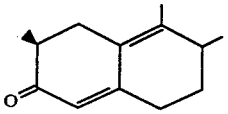 (N-ethyl-N-methyl-p-phenyl) | " | —C≡C—H |
| " | " | " | —C≡C—CF₃ |
| " | " | " | —C≡C—CH₂CH₃ |
| " | " | " | —CH₂—C≡C—H |
| " | " | " | —C≡C—SiMe₃ |
| " | " | —C≡C—H | OH |
| " | " | —C≡C—SiMe₃ | OH |
| 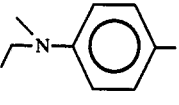 | 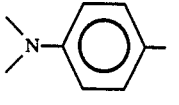 (N,N-diethyl-p-phenyl) | CH₂CH₃ | OH | —C≡C—H |
| " | " | " | OH | —C≡C—CH₃ |
| " | " | " | OH | —CH₂—C≡C—H |
| " | " | CH₃ | —C(=O)—CH₂OH | H |
| " | " | " | " | OH |
| " | 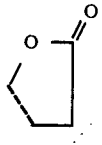 (N,N-dimethyl-p-phenyl) | " | OH | —C≡C—H |
| " | " | " | (lactone ring) | |

-continued

| [Ring A-B structure] | R₁ | R₂ | R₃ | R₄ |
|---|---|---|---|---|
| [Structure 1: cyclohexenone with methyl groups, O=] | [N,N-dimethyl-p-aminophenyl] | " | —C≡C—H | OH |
| " | " | " | OH | —CH₂—C≡C—H |
| " | [2-fluoro-4-(N,N-dimethylamino)phenyl] | " | OH | —C≡C—H |
| " | " | " | " | —C≡C—CH₃ |
| " | " | " | " | —CH₂—C≡C—H |
| " | " | " | —C≡C—H | OH |
| " | [N-methylindoline] | " | OH | —C≡C—H |
| [Structure 2: same as structure 1] | [N-methylindoline] | " | " | —C≡C—CF₃ |
| " | " | " | " | —CH₂—C≡C—H |
| " | " | " | " | —C≡C—CH₂CH₃ |
| " | " | " | " | —C≡C—Cl |
| " | " | " | " | —C≡C—SiMe₃ |
| " | " | " | —C≡C—H | OH |
| " | " | " | —C≡C—SiMe₃ | OH |
| [Structure 3: tetrahydronaphthol, HO-] | [N-methylindoline] | CH₂CH₃ | OH | —C≡C—H |
| " | " | " | " | —C≡C—CH₃ |
| " | " | " | " | —CH₂—C≡C—H |
| " | " | CH₃ | —C(=O)—CH₂OH | —H |
| " | " | " | " | —OH |
| " | " | " | —C(=O)—CH₃ | —H |
| [Structure 4: cyclohexanone with methyls, O=] | [N,N-dimethyl-p-aminophenyl] | " | —OH | —C≡C—H |
| " | " | " | [γ-butyrolactone fused structure] | |

-continued

| 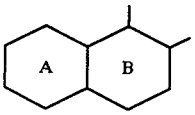 | R₁ | R₂ | R₃ | R₄ |
|---|---|---|---|---|
| " | " | " | " | —C≡C—CH₂CH₃<br>—CH₂—C≡C—H |
| " | " | " | —C≡C—H | —OH |
| " | " | " | $\underset{O}{\overset{\|\|}{-C}}$—CH₂OH | H |
| " | 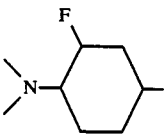 | " | " | " |
| 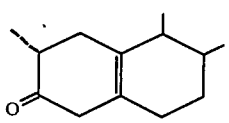 | 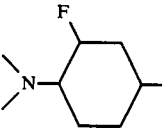 | " | OH | —C≡C—H |
| " | " | " | " | —C≡C—CH₃<br>—C≡C—CH₂CH₃<br>—CH₂—C≡C—H |
| " | " | " | —C≡C—H | —OH |
| 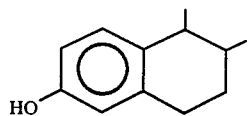 | 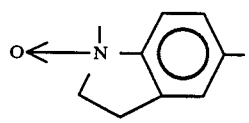 | " | " | " |
| " | " | " | OH | —C≡C—H<br>—C≡C—CF₃<br>—C≡C—Cl<br>—C≡C—CH₂CH₃<br>—CH₂—C≡C—H<br>—C≡C—SiMe₃ |
| 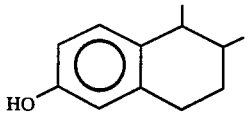 | 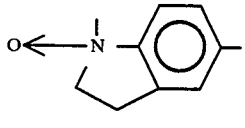 | " | $\underset{O}{\overset{\|\|}{-C}}$—CH₂OH | —H |
| 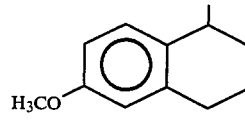 | 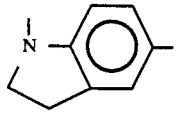 | CH₂CH₃ | OH | —C≡C—H |
| " | " | " | " | —C≡C—CH₃<br>—CH₂—C≡C—H |
| " | " | CH₃ | $\underset{O}{\overset{\|\|}{-C}}$—CH₂OH | —H |
| " | " | " | " | —OH |
| " | " | " | $\underset{O}{\overset{\|\|}{-C}}$—CH₃ | —H |
| 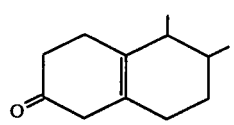 | 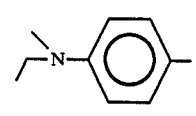 | " | —OH | —C≡C—H |

-continued
| 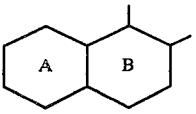 | R₁ | R₂ | R₃ | R₄ |
|---|---|---|---|---|
| " | " | " | " | —C≡C—CH₃ |
| " | " | " | " | —C≡C—CH₂CH₃ |
| " | " | " | " | —CH₂—C≡C—H |
| " | " | " | —C≡C—H | —OH |
| " | " | " | —C(O)—CH₂OH | H |
| " | " | " | 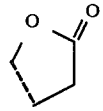 | |
| 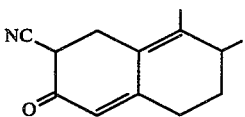 | 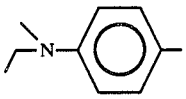 | " | OH | —C≡C—H |
| " | " | " | " | —C≡C—CH₃ |
| " | " | " | " | —C≡C—CH₂CH₃ |
| " | " | " | " | —CH₂—C≡C—H |
| " | " | " | —C≡C—H | —OH |
| 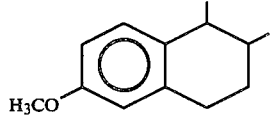 | 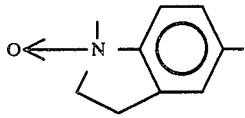 | " | " | " |
| " | " | " | OH | —C≡C—H |
| " | " | " | " | —C≡C—CF₃ |
| " | " | " | " | —C≡C—Cl |
| " | " | " | " | —C≡C—CH₂CH₃ |
| " | " | " | " | —CH₂—C≡C—H |
| " | " | " | " | —C≡C—SiMe₃ |
| 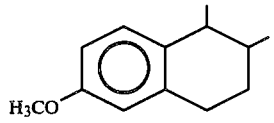 | 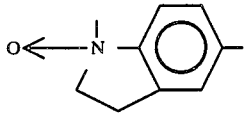 | " | —C(O)—CH₂OH | —H |
| 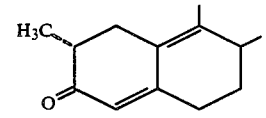 | 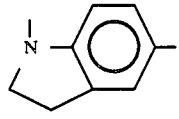 | CH₂CH₃ | OH | —C≡C—H |
| " | " | " | " | —C≡C—CH₃ |
| " | " | " | " | —CH₂—C≡C—H |
| " | " | CH₃ | —C(O)—CH₂OH | —H |
| " | " | " | " | —OH |
| " | " | " | —C(O)—CH₃ | —H |
| 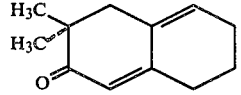 | 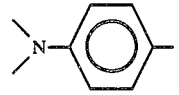 | " | —OH | —C≡C—H |

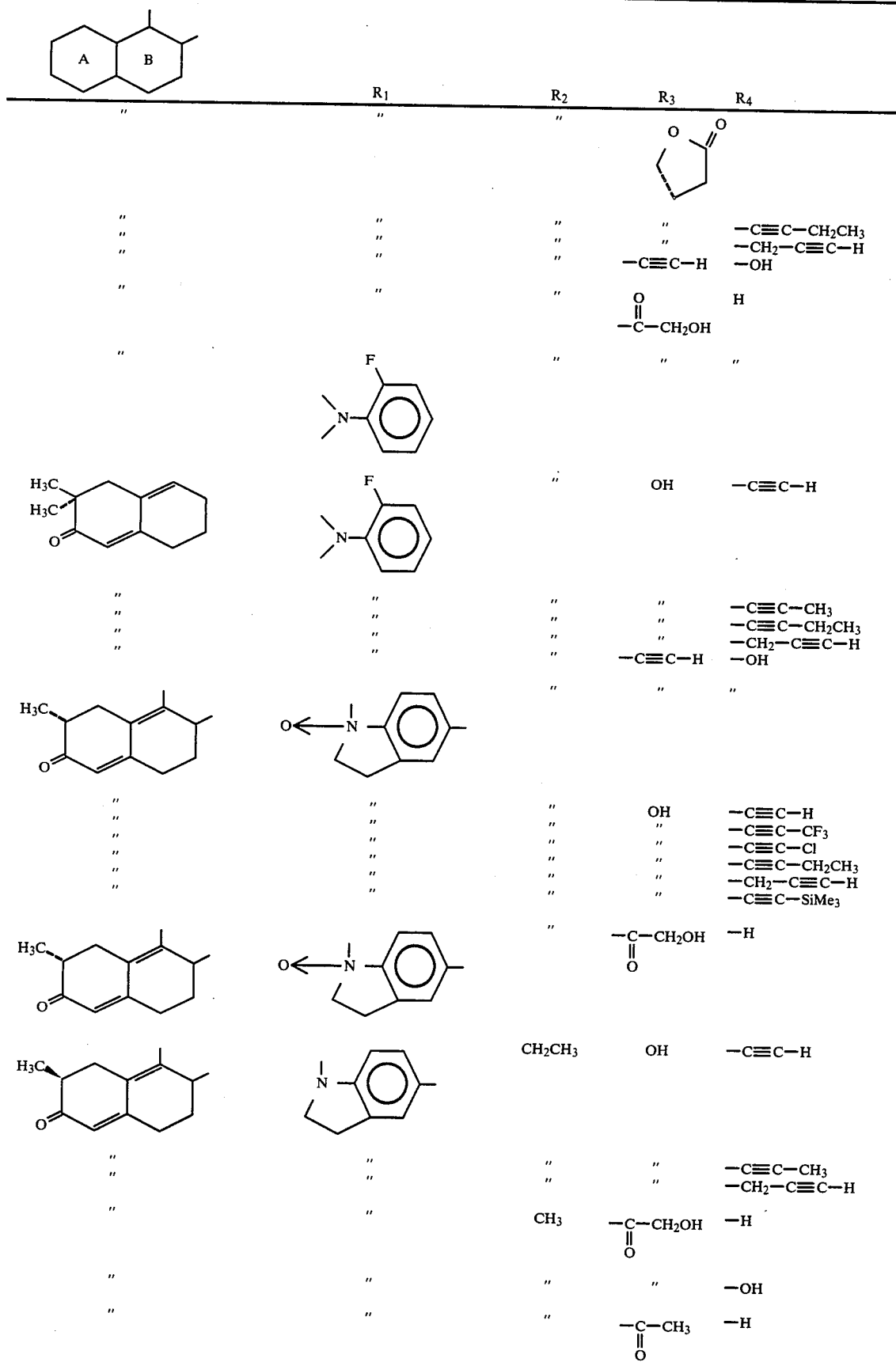

-continued
| | $R_1$ | $R_2$ | $R_3$ | $R_4$ |
|---|---|---|---|---|
| 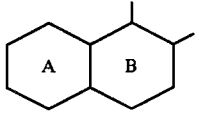 | 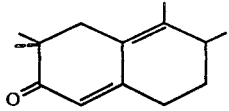 | " | —OH | —C≡C—H |
| " | " | " | " | —C≡C—CH₃ |
| " | " | " | " | —C≡C—CH₂CH₃ |
| " | " | " | " | —CH₂—C≡C—H |
| " | " | " | —C≡C—H | —OH |
| " | " | " | —C(O)—CH₂OH | H |
| " | 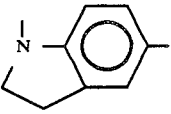 | " | " | " |
| 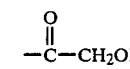 | 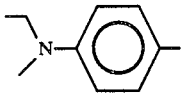 | " | OH | —C≡C—H |
| " | " | " | " | —C≡C—CH₃ |
| " | " | " | " | —C≡C—CH₂CH₃ |
| " | " | " | " | —CH₂—C≡C—H |
| " | " | " | —C≡C—H | —OH |
| 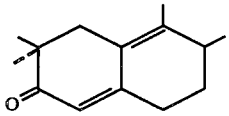 | 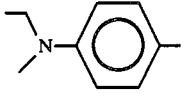 | " | " | " |
| " | " | " | OH | —C≡C—H |
| " | " | " | " | —C≡C—CF₃ |
| " | " | " | " | —C≡C—Cl |
| " | " | " | " | —C≡C—CH₂CH₃ |
| " | " | " | " | —CH₂—C≡C—H |
| " | " | " | " | —C≡C—SiMe₃ |
| " | " | " | —C(O)—CH₂OH | —H |
| 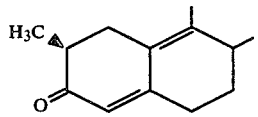 | 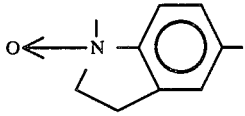 | " | OH | —C≡C—H |
| 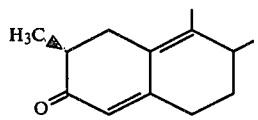 | 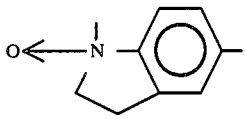 | " | " | —C≡C—CH₃ |
| " | " | " | " | —CH₂—C≡C—H |
| " | " | " | —C≡C—H | —OH |
| " | 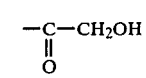 | " | " | " |

-continued

| ![A-B ring system with methyl groups] | R₁ | R₂ | R₃ | R₄ |
|---|---|---|---|---|
| " | " | " | OH | —C≡C—H |
| | | | " | —C≡C—CH₃ |
| " | " | " | " | —CH₂—C≡C—H |
| HO-[tetrahydronaphthalene with methyls] | " | " | " | —C≡C—CH₂CH₃ |
| | | (CH₃)₂N—C₆H₄— | | |
| " | " | " | —C≡C—SiMe₃ | —C≡C—CF₃ |
| | | | —OH | |
| " | " | " | —C(=O)—CH₂OH | —H |
| " | " | " | " | —OH |
| " | " | " | —C(=O)—CH₃ | —H |
| HO-[tetrahydronaphthalene with methyls] | (CH₃)₂N—C₆H₄— | —CH₂CH₃ | OH | —C≡C—H |
| " | " | " | " | —C≡C—CH₃ |
| " | " | " | " | —C≡C—Cl |
| " | " | " | " | —C≡C—CH₂—CH₃ |
| " | " | " | " | —C≡C—SiMe₃ |
| " | " | " | " | —CH₂—C≡C—H |
| " | " | " | —C(=O)—CH₂OH | —H |
| HO-[tetrahydronaphthalene with methyls] | H₃CS—C₆H₄— | CH₃ | —C≡C—H | —OH |
| " | " | " | —C(=O)—CH₂OH | —H |
| " | " | " | OH | —CH₂—C≡C—H |
| " | " | " | " | " |
| | | EtS—C₆H₄— | | |
| H₃CO-[tetrahydronaphthalene] | H₃CS—C₆H₄— (3-position) | " | OH | —C≡C—H |
| " | " | " | " | —C≡C—CH₃ |
| " | " | " | " | —CH₂—C≡C—H |

-continued

| | $R_1$ | $R_2$ | $R_3$ | $R_4$ |
|---|---|---|---|---|
| " | " | " | —C≡C—H | —OH |
| " | 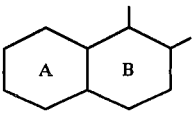 (3-EtS-phenyl) | " | " | " |
| " | " | " | OH | —C≡C—H |
| " | " | " | " | —C≡C—CH$_3$ |
| 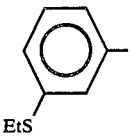 (6-methoxy-tetrahydronaphthyl) | " | " | " | —CH$_2$—C≡C—H |
| " | 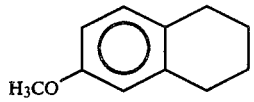 (4-NMe$_2$-phenyl) | " | " | —C≡C—CH$_2$CH$_3$ |
| " | " | " | " | —C≡C—CF$_3$ |
| " | " | " | —C≡C—SiMe$_3$ | —OH |
| " | " | " | —C(=O)—CH$_2$OH | —H |
| " | " | " | " | —OH |
| " | " | " | —C(=O)—CH$_3$ | —H |
| 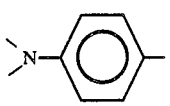 | 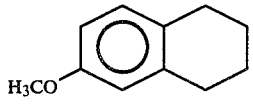 (4-NMe$_2$-phenyl) | —CH$_2$CH$_3$ | OH | —C≡C—H |
| " | " | " | " | —C≡C—CH$_3$ |
| " | " | " | " | —C≡C—Cl |
| " | " | " | " | —C≡C—CH$_2$—CH$_3$ |
| " | " | " | " | —C≡C—SiMe$_3$ |
| " | " | " | " | —CH$_2$—C≡C—H |
| " | " | " | —C(=O)—CH$_2$OH | —H |
| 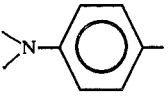 | 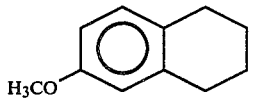 (4-H$_3$CS-phenyl) | CH$_3$ | —C≡C—H | —OH |
| " | " | " | —C(=O)—CH$_2$OH | —H |
| " | " | " | OH | —CH$_2$—C≡C—H |
| " | 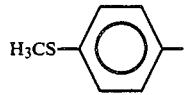 (4-EtS-phenyl) | " | " | " |

-continued
| | $R_1$ | $R_2$ | $R_3$ | $R_4$ |
|---|---|---|---|---|
| 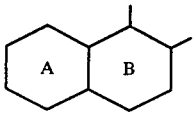 | 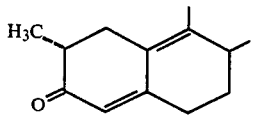 H₃CS— | " | OH | —C≡C—H |
| " | " | " | " | —C≡C—CH₃ |
| " | " | " | " | —CH₂—C≡C—H |
| " | " | " | —C≡C—H | —OH |
| " | 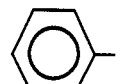 EtS— | " | " | " |
| " | " | " | OH | —C≡C—H |
| " | " | " | " | —C≡C—CH₃ |
| 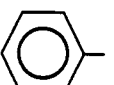 | " | " | " | —CH₂—C≡C—H |
| " | 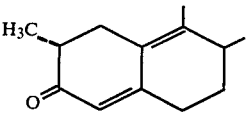 (CH₃)₂N— | " | " | —C≡C—CH₂CH₃ |
| " | " | " | —C≡C—SiMe₃ | —C≡C—CF₃ |
| " | " | " | " | —OH |
| " | " | " | —C(O)—CH₂OH | —H |
| " | " | " | " | —OH |
| " | " | " | —C(O)—CH₃ | —H |
| 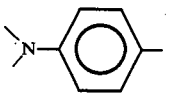 | 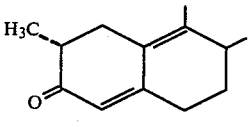 (CH₃)₂N— | —CH₂CH₃ | OH | —C≡C—H |
| " | " | " | " | —C≡C—CH₃ |
| " | " | " | " | —C≡C—Cl |
| " | " | " | " | —C≡C—CH₂—CH₃ |
| " | " | " | " | —C≡C—SiMe₃ |
| " | " | " | " | —CH₂—C≡C—H |
| " | " | " | —C(O)—CH₂OH | —H |
| 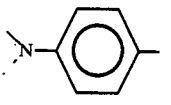 | 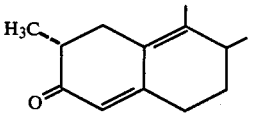 H₃CS— | CH₃ | —C≡C—H | —OH |
| " | " | " | —C(O)—CH₂OH | —H |

-continued

| | R₁ | R₂ | R₃ | R₄ |
|---|---|---|---|---|
| " | " | " | OH | —CH₂—C≡C—H |
| " | EtS-C₆H₄- | " | " | " |
| (H₃C ketone decalin structure) | H₃CS-C₆H₄- | " | OH | —C≡C—H |
| " | " | " | " | —C≡C—CH₃ |
| " | " | " | " | —CH₂—C≡C—H |
| " | " | " | —C≡C—H | —OH |
| " | EtS-C₆H₄- | " | " | " |
| " | " | " | OH | —C≡C—H |
| " | " | " | " | —C≡C—CH₃ |
| (H₃C ketone decalin structure) | " | " | " | —CH₂—C≡C—H |
| " | Me₂N-C₆H₄- | " | " | —C≡C—CH₂CH₃ |
| " | " | " | " | —C≡C—CF₃ |
| " | " | " | —C≡C—SiMe₃ | —OH |
| " | " | " | —C(=O)—CH₂OH | —H |
| " | " | " | " | —OH |
| " | " | " | —C(=O)—CH₃ | —H |
| (H₃C ketone decalin structure) | Me₂N-C₆H₄- | —CH₂CH₃ | OH | —C≡C—H |
| " | " | " | " | —C≡C—CH₃ |
| " | " | " | " | —C≡C—Cl |
| " | " | " | " | —C≡C—CH₂—CH₃ |
| " | " | " | " | —C≡C—SiMe₃ |
| " | " | " | " | —CH₂—C≡C—H |
| " | " | " | —C(=O)—CH₂OH | —H |

-continued

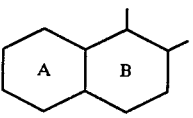

| R₁ structure | R₁ | R₂ | R₃ | R₄ |
|---|---|---|---|---|
| 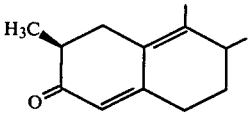 | H₃CS—⌬— | CH₃ | —C≡C—H | —OH |
| " | " | " | —C(=O)—CH₂OH | —H |
| " | " | " | OH | —CH₂—C≡C—H |
| " | EtS—⌬— | " | " | " |
| 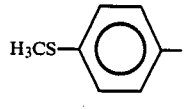 | (Me)₂N→O —⌬— | " | —C≡C—H | —OH |
| " | " | " | —C(=O)—CH₂OH | —H |
| 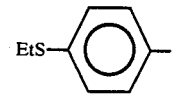 | " | " | " | " |
| " | " | " | —C≡C—H | —OH |
| " | " | " | OH | —CH₂—C≡C—H |
| " | " | " | " | —C≡C—CH₂CH₃ |
| " | " | " | " | —C≡C—CF₃ |
| " | " | " | " | —C≡C—H |
| " | " | " | " | —C≡C—SiMe₃ |
| 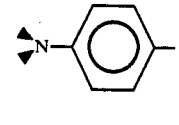 | " | " | OH | —C≡C—H |
| " | " | " | " | —C≡C—CH₃ |
| " | " | " | " | —C≡C—CH₂CH₃ |
| " | " | " | " | —C≡C—Cl |
| " | " | " | " | —C≡C—SiMe₃ |
| " | " | " | " | —CH₂—C≡C—H |
| " | " | " | —C≡C—H | —OH |
| " | " | " | " | " |
| 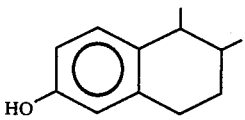 | 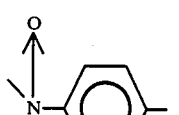 | " | " | " |
| " | " | " | OH | —C≡C—H |
| " | " | " | " | —C≡C—CH₃ |
| " | " | " | " | —C≡C—CH₂—CH₃ |
| " | " | " | " | —C≡C—Cl |
| " | " | " | " | —C≡C—SiMe₃ |
| " | " | " | " | —CH₂—C≡C—H |

-continued
| | R₁ | R₂ | R₃ | R₄ |
|---|---|---|---|---|
| 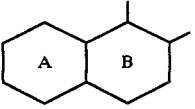 | 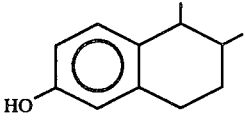 | " | OH | —C≡C—H |
| " | " | " | " | —C≡C—CF₃ |
| " | " | " | " | —C≡C—CH₃ |
| " | " | " | " | —C≡C—Cl |
| 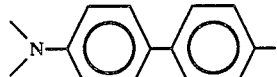 | 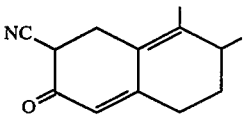 | " | —C≡C—H | —OH |
| " | " | " | —C(O)—CH₂OH | —H |
| 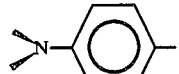 | 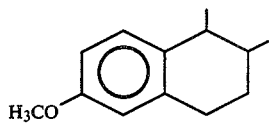 | " | " | " |
| " | " | " | —C≡C—H | —OH |
| " | " | " | OH | —CH₂—C≡C—H |
| " | " | " | " | —C≡C—CH₂CH₃ |
| " | " | " | " | —C≡C—CF₃ |
| " | " | " | " | —C≡C—H |
| " | " | " | " | —C≡C—SiMe₃ |
| 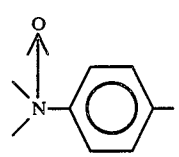 | 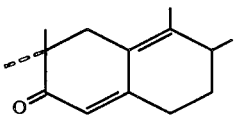 | " | OH | —C≡C—H |
| " | " | " | " | —C≡C—CH₃ |
| " | " | " | " | —C≡C—CH₂CH₃ |
| " | " | " | " | —C≡C—Cl |
| " | " | " | " | —C≡C—SiMe₃ |
| " | " | " | " | —CH₂—C≡C—H |
| " | " | " | —C≡C—H | —OH |
| 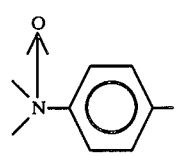 | 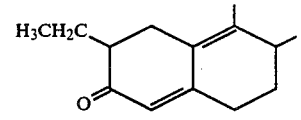 | " | " | " |
| " | " | " | OH | —C≡C—H |
| " | " | " | " | —C≡C—CH₃ |
| " | " | " | " | —C≡C—CH₂—CH₃ |
| " | " | " | " | —C≡C—Cl |
| " | " | " | " | —C≡C—SiMe₃ |
| " | " | " | " | —CH₂—C≡C—H |
| 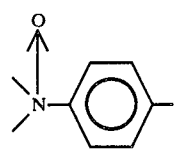 | 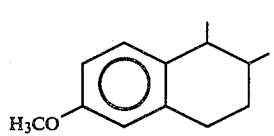 | " | OH | —C≡C—H |
| " | " | " | " | —C≡C—CF₃ |

-continued
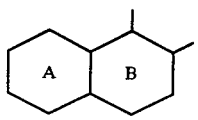
| | R₁ | R₂ | R₃ | R₄ |
|---|---|---|---|---|
| " | " | " | " | —C≡C—CH₃ |
| " | " | " | " | —C≡C—Cl |
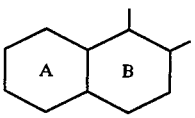
| | R₁ | R₂ | R₃ | R₄ |
|---|---|---|---|---|
| 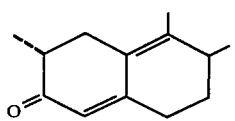 | 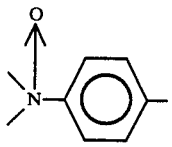 | CH₃ | —C≡C—H | —OH |
| " | " | " | —C(O)—CH₂OH | —H |
| 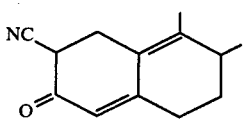 | 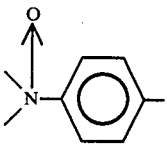 | " | " | " |
| " | " | " | —C≡C—H | —OH |
| " | " | " | OH | —CH₂—C≡C—H |
| " | " | " | " | —C≡C—CH₂CH₃ |
| " | " | " | " | —C≡C—CF₃ |
| " | " | " | " | —C≡C—H |
| " | " | " | " | —C≡C—SiMe₃ |
| 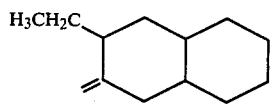 | 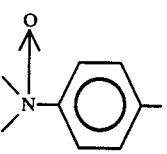 | " | OH | —C≡C—H |
| " | " | " | " | —C≡C—CH₃ |
| " | " | " | " | —C≡C—CH₂CH₃ |
| " | " | " | " | —C≡C—Cl |
| " | " | " | " | —C≡C—SiMe₃ |
| " | " | " | " | —CH₂—C≡C—H |
| " | " | " | —C≡C—H | —OH |
| 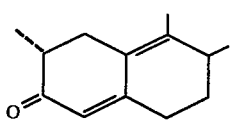 |  | " | " | " |
| " | " | " | OH | —C≡C—H |
| " | " | " | " | —C≡C—CH₃ |
| " | " | " | " | —C≡C—CH₂—CH₃ |
| " | " | " | " | —C≡C—Cl |
| " | " | " | " | —C≡C—SiMe₃ |
| " | " | " | " | —CH₂—C≡C—H |
| | | " | OH | —C≡C—H |
| " | " | " | " | —C≡C—CF₃ |

-continued

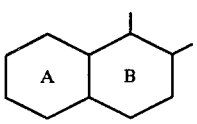

| Structure | R₁ | R₂ | R₃ | R₄ |
|---|---|---|---|---|
| " | " | " | " | —C≡C—CH₃ |
| " | " | " | " | —C≡C—Cl |
| 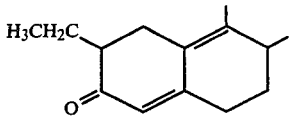 | 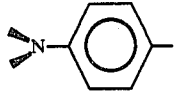 | CH₃ | —C≡C—H | —OH |
| " | " | " | —C(=O)—CH₂OH | —H |
| 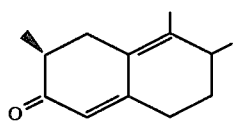 | 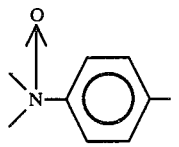 | " | " | " |
| " | " | " | —C≡C—H | —OH |
| " | " | " | OH | —CH₂—C≡C—H |
| " | " | " | " | —C≡C—CH₂CH₃ |
| " | " | " | " | —C≡C—CF₃ |
| " | " | " | " | —C≡C—H |
| " | " | " | " | —C≡C—SiMe₃ |
| " | " | " | OH | —C≡C—H |
| 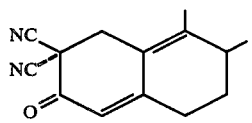 | 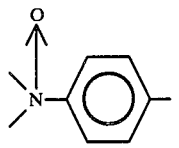 | " | " | " |
| " | " | " | " | —C≡C—CH₃ |
| " | " | " | " | —C≡C—CH₂CH₃ |
| " | " | " | " | —C≡C—Cl |
| " | " | " | " | —C≡C—SiMe₃ |
| " | " | " | " | —CH₂—C≡C—H |
| " | " | " | —C≡C—H | —OH |
| 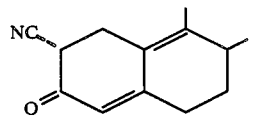 | 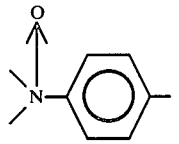 | " | " | " |
| " | " | " | OH | —C≡C—H |
| " | " | " | " | —C≡C—CH₃ |
| " | " | " | " | —C≡C—CH₂—CH₃ |
| " | " | " | " | —C≡C—Cl |
| " | " | " | " | —C≡C—SiMe₃ |
| " | " | " | " | —CH₂—C≡C—H |
| 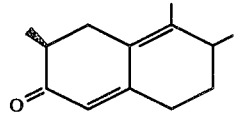 | 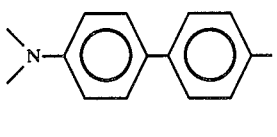 | " | OH | —C≡C—H |
| " | " | " | " | —C≡C—CF₃ |
| " | " | " | " | —C≡C—CH₃ |
| " | " | " | " | —C≡C—Cl |
| 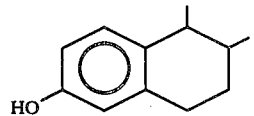 | 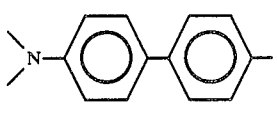 | CH₃ | OH | —CH₂—C≡C—H |

-continued
| 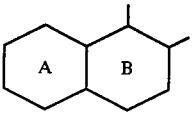 | R₁ | R₂ | R₃ | R₄ |
|---|---|---|---|---|
| " | " | " | —C≡C—H | —H |
| " | " | " | " | —OH |
| " | " | " | —C(=O)—CH₂OH | —H |
| " | 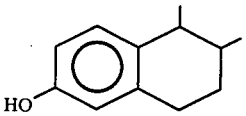 | " | " | " |
| 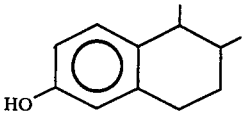 | " | " | OH | —C≡C—H |
| " | " | " | " | —C≡C—CH₃ |
| " | " | " | " | —C≡C—Cl |
| " | " | " | " | —CH₂—C≡C—H |
| " | " | " | —C≡C—H | —OH |
| " | 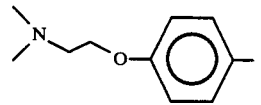 | " | " | " |
| 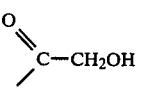 | " | " | OH | —C≡C—H |
| " | " | " | " | —C≡C—CF₃ |
| " | " | " | " | —C≡C—CH₃ |
| " | " | " | " | —CH₂—C≡C—H |
| " | " | " | " | —H |
| " | 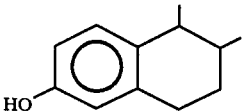 | " | " | —C≡C—H |
| " | " | " | " | —CH₂—C≡C—H |
| " | " | " | —C≡C—H | —OH |
| " | " | " | —C(=O)—CH₂OH | —H |
| 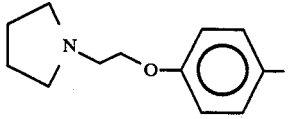 | " | " | " | " |
| " | " | " | —C≡C—H | —OH |
| " | " | " | —OH | —C≡C—H |
| " | " | " | " | —C≡C—CH₃ |
| " | " | " | " | —CH₂—C≡C—H |

-continued
| | R$_1$ | R$_2$ | R$_3$ | R$_4$ |
|---|---|---|---|---|
| " | 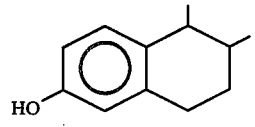 | " | —OH | —C≡C—H |
| | " | " | " | —C≡C—CH$_3$ |
| 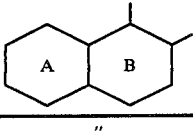 | | | | |
| 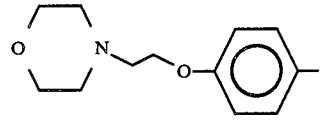 | 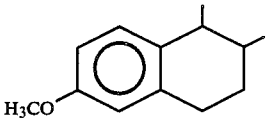 | CH$_3$ | OH | —CH$_2$—C≡C—H |
| " | " | " | " | —H |
| " | " | " | —C≡C—H | —OH |
| " | " | " | —C(=O)—CH$_2$OH | —H |
| " | 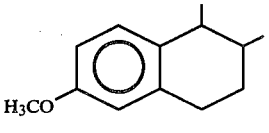 | " | " | " |
| " | " | " | OH | —C≡C—H |
| " | " | " | " | —C≡C—CH$_3$ |
| " | " | " | " | —C≡C—Cl |
| 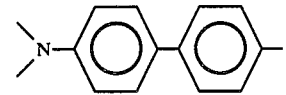 | | | | |
| " | " | " | " | —CH$_2$—C≡C—H |
| " | " | " | —C≡C—H | —OH |
| " |  | " | " | " |
| " | " | " | OH | —C≡C—H |
| " | " | " | " | —C≡C—CF$_3$ |
| " | " | " | " | —C≡C—CH$_3$ |
| " | " | " | " | —CH$_2$—C≡C—H |
| 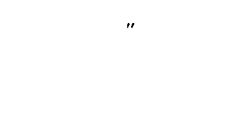 | | | | |
| " | " | " | " | —H |
| " | 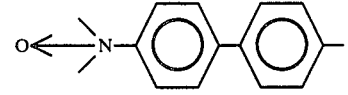 | " | " | —C≡C—H |
| " | " | " | " | —CH$_2$—C≡C—H |
| " | " | " | —C≡C—H | —OH |

-continued
| 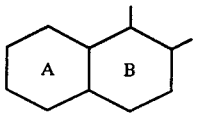 | R₁ | R₂ | R₃ | R₄ |
|---|---|---|---|---|
| " | " | " | 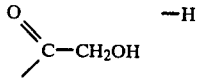 | —H |
| " | 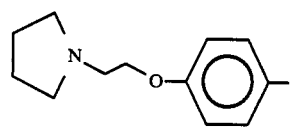 | " | " | " |
| 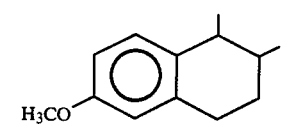 | " | " | —C≡C—H | —OH |
| " | " | " | —OH<br>"<br>" | —C≡C—H<br>—C≡C—CH₃<br>—CH₂—C≡C—H |
| " | 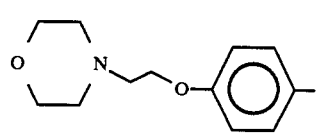 | " | —OH | —C≡C—H |
| " | " | " | " | —C≡C—CH₃ |
| 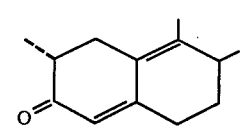 | 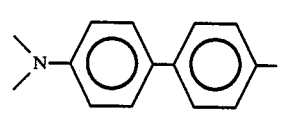 | CH₃ | OH | —CH₂—C≡C—H |
| " | " | " | —C≡C—H | —H<br>—OH |
| " | " | " | 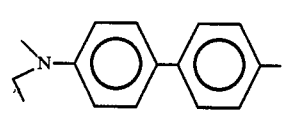 | —H |
| " | " | " | " | " |
| " | " | " | OH<br>" | —C≡C—H<br>—C≡C—CH₃ |
| " | " | " | " | —C≡C—Cl |
| 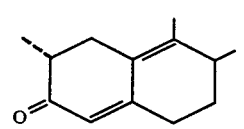 | " | " | "<br>—C≡C—H | —CH₂—C≡C—H<br>—OH |
| " | " | " | " | " |
| " | 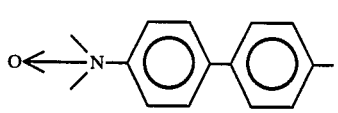 | " | " | " |
| " | " | " | OH<br>"<br>" | —C≡C—H<br>—C≡C—CF₃<br>—C≡C—CH₃ |

-continued
| A-B structure | R₁ | R₂ | R₃ | R₄ |
|---|---|---|---|---|
| 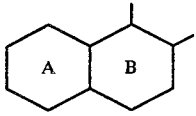 |  | " | " | —CH₂—C≡C—H |
| " | " | " | " | —H |
| " | " | " | " | —C≡C—H |
| " | 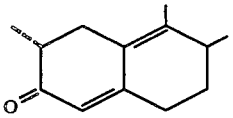 | " | " | " |
| " | " | " | " | —CH₂—C≡C—H |
| " | " | " | —C≡C—H | —OH |
| " | " | " | —C(=O)—CH₂OH | —H |
| " | 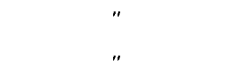 | " | " | " |
| 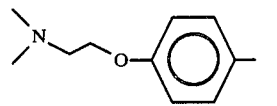 | " | " | —C≡C—H | —OH |
| " | " | " | —OH | —C≡C—H |
| " | " | " | " | —C≡C—CH₃ |
| " | " | " | " | —CH₂—C≡C—H |
| " | 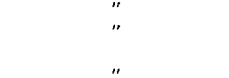 | " | —OH | —C≡C—H |
| " | " | " | " | —C≡C—CH₃ |
|  |  | CH₃ | OH | —CH₂—C≡C—H |
| " | " | " | " | —H |
| " | " | " | —C≡C—H | —OH |
| " | " | " | —C(=O)—CH₂OH | —H |
| " | 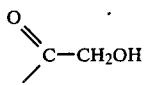 | " | " | " |
| " | " | " | " | —C≡C—H |
| " | " | " | " | —C≡C—CH₃ |

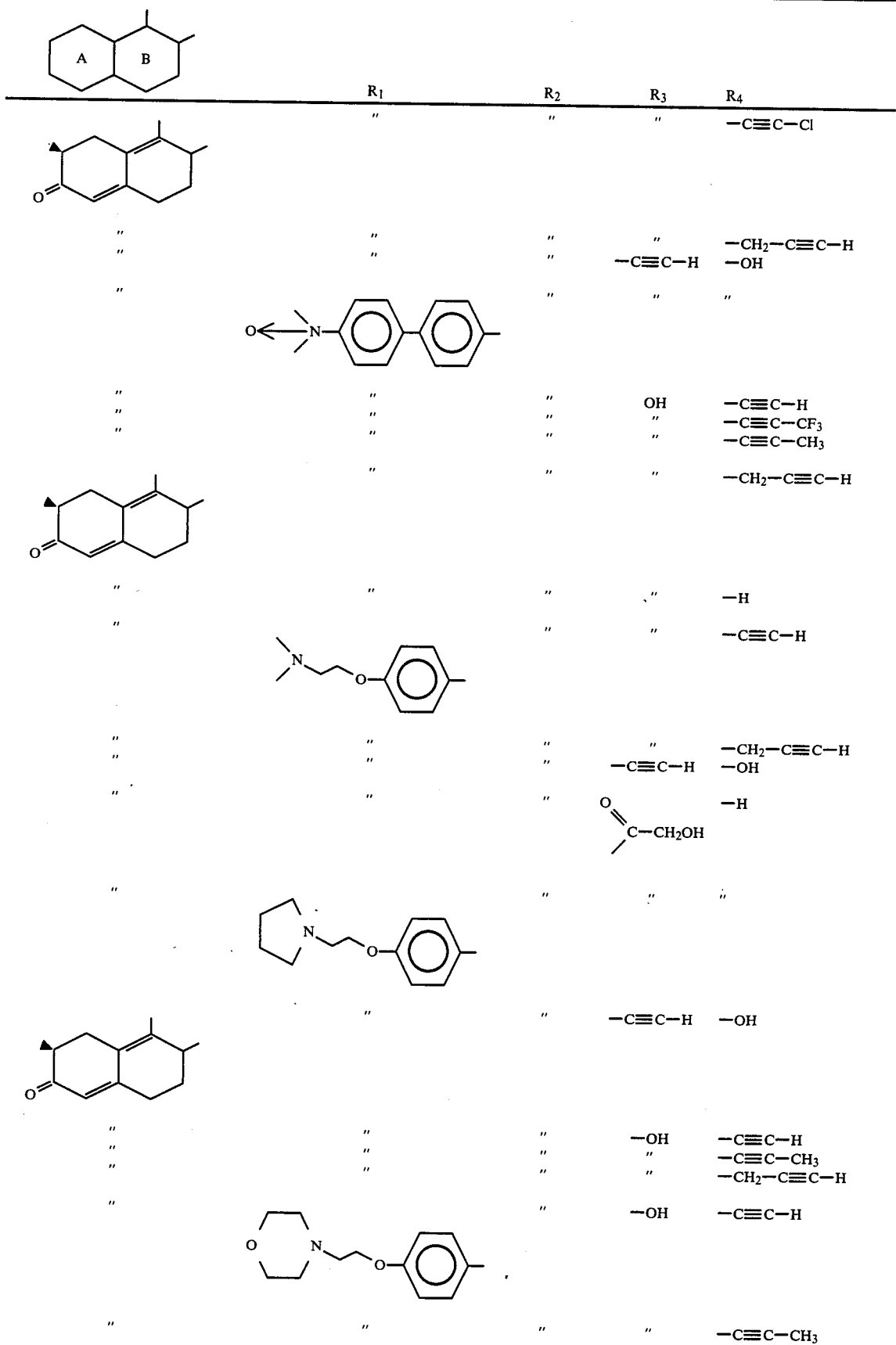

-continued

| A B (structure) | R₁ | R₂ | R₃ | R₄ |
|---|---|---|---|---|
| HO-tetrahydronaphthalene (dimethyl) | morpholino-ethoxy-phenyl | CH₃ | —OH | —CH₂—C≡C—H |
| " | " | " | —C≡C—H | —OH |
| " | " | " | =O, —CH₂OH (acyl) | —H |
| " | (CH₃)₂N-CH₂CH₂-S-phenyl | " | | |
| " | " | " | —C≡C—H | OH |
| " | " | " | OH | —C≡C—CF₃ |
| " | " | " | OH | —C≡C—H |
| " | " | " | " | —CH₂—CH=CH₂ |
| HO-tetrahydronaphthalene (dimethyl) | " | " | " | CH₂—C≡C—H, —CH₂ |
| " | (CH₃)₂N-CH₂CH₂-S-phenyl | " | =O, —CH₃ (acetyl) | —CH₃ |
| " | " | " | OH | —CH₂—CN |
| " | " | " | OH | —C≡C—H |
| NC, O-substituted dimethyl octahydronaphthalene | | | | |
| " | " | " | " | —C≡C—CH₃ |
| " | " | " | " | —C≡C—CH₂CH₃ |
| " | " | " | " | —C≡C—Cl |
| " | " | " | " | —CH₂—C≡C—H |
| " | (CH₃)₂N-CH₂CH₂-S-phenyl | " | —C≡C—H | —OH |
| " | " | " | =O, —CH₂OH | —H |
| isoxazole-fused tetrahydronaphthalene | (CH₃)₂N-phenyl | " | " | " |

4,547,493
-continued
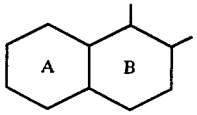
| | R₁ | R₂ | R₃ | R₄ |
|---|---|---|---|---|
| " | " | " | —C≡C—H | —OH |
| " | " | " | OH | —C≡C—H |
| " | " | " | " | —C≡C—CH₃ |
| " | " | " | " | —C≡C—CH₂—CH₃ |
| " | " | " | " | —C≡C—Cl |
| " | " | " | " | —CH₂—C≡C—H |
| | 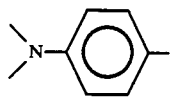 | CH₂CH₃ | " | —C≡C—H |
| 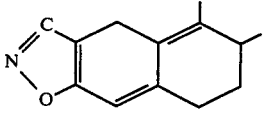 | " | " | " | —C≡C—CH₃ |
| 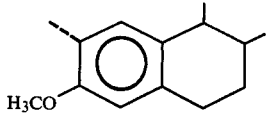 | 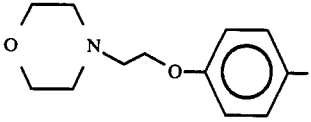 | CH₃ | —OH | —CH₂—C≡C—H |
| " | " | " | —C≡C—H | —OH |
| " | " | " | 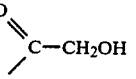 | —H |
| " | 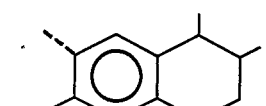 | " | " | " |
| " | " | " | —C≡C—H | OH |
| " | " | " | OH | —C≡C—CF₃ |
| " | " | " | OH | —C≡C—H |
| 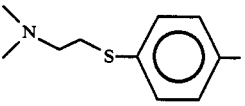 | " | " | " | —CH₂—CH=CH₂ |
| " | " | " | " | CH₂—C≡C—H |
| " | " | " | " | —CH₂ |
| " | 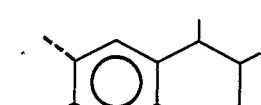 | " | 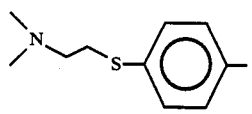 | —CH₃ |
| " | " | " | OH | —CH₂—CN |
| " | " | " | OH | —C≡C—H |
| 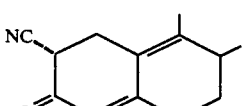 | " | " | " | —C≡C—CH₃ |
| " | " | " | " | —C≡C—CH₂CH₃ |
| " | " | " | " | —C≡C—Cl |
| " | " | " | " | —CH₂—C≡C—H |

-continued
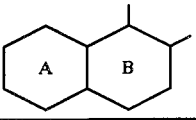
| | R₁ | R₂ | R₃ | R₄ |
|---|---|---|---|---|
| " | 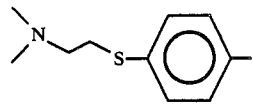 | " | —C≡C—H | —OH |
| " | " | " | 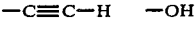 | —H |
|  | " | " | " | " |
| " | " | " | —C≡C—H | —OH |
| " | " | " | OH | —C≡C—H |
| " | " | " | " | —C≡C—CH₃ |
| " | " | " | " | —C≡C—CH₂—CH₃ |
| " |  | " | " | —C≡C—Cl |
| " | " | " | " | —CH₂—C≡C—H |
| " | " | CH₂CH₃ | " | —C≡C—H |
| " | " | " | " | —C≡C—CH₃ |
|  |  | CH₃ | —OH | —CH₂—C≡C—H |
| " | " | " | —C≡C—H | —OH |
| " | " | " | 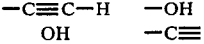 | —H |
| " | 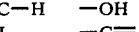 | " | " | " |
| " | " | " | —C≡C—H | OH |
| " | " | " | OH | —C≡C—CF₃ |
| " | " | " | OH | —C≡C—H |
| " | " | " | " | —CH₂—CH=CH₂ |
|  | | | | |
| " | " | " | " | CH₂—C≡C—H |
| " | " | " | " | —CH₂ |

-continued

| | R₁ | R₂ | R₃ | R₄ |
|---|---|---|---|---|
| " | (CH₃)₂N-CH₂CH₂-S-C₆H₄- | " | -C(=O)-CH₃ | -CH₃ |
| " | " | " | OH | -CH₂-CN |
| [H₃C, NC, =O substituted bicyclic] | " | " | OH | -C≡C-H |
| " | " | " | " | -C≡C-CH₃ |
| " | " | " | " | -C≡C-CH₂CH₃ |
| " | " | " | " | -C≡C-Cl |
| " | " | " | " | -CH₂-C≡C-H |
| " | (CH₃)₂N-CH₂CH₂-S-C₆H₄- | " | -C≡C-H | -OH |
| " | " | " | -C(=O)-CH₂OH | -H |
| [isoxazole-fused bicyclic] | 2-F-4-(CH₃)₂N-C₆H₃- | " | " | " |
| " | " | " | -C≡C-H | -OH |
| " | " | " | OH | -C≡C-H |
| " | " | " | " | -C≡C-CH₃ |
| " | " | " | " | -C≡C-CH₂-CH₃ |
| " | " | " | " | -C≡C-Cl |
| " | " | " | " | -CH₂-C≡C-H |
| " | 2-F-4-(CH₃)₂N-C₆H₃- | CH₂CH₃ | " | -C≡C-H |
| " | " | " | " | -C≡C-CH₃ |
| [methyl-oxo bicyclic] | morpholino-CH₂CH₂-O-C₆H₄- | CH₃ | -OH | -CH₂-C≡C-H |
| " | " | " | -C≡C-H | -OH |
| " | " | " | -C(=O)-CH₂OH | -H |

-continued

| [Ring A-B structure] | R₁ | R₂ | R₃ | R₄ |
|---|---|---|---|---|
| " | (CH₃)₂N-CH₂CH₂-S-C₆H₄- | " | " | " |
| " | " | " | —C≡C—H | OH |
| " | " | " | OH | —C≡C—CF₃ |
| " | " | " | OH | —C≡C—H |
| [methyl-enone decalin structure] | " | " | " | —CH₂—CH=CH₂ |
| " | " | " | " | CH₂—C≡C—H |
| " | " | " | " | —CH₂ |
| " | (CH₃)₂N-CH₂CH₂-S-C₆H₄- | " | CH₃-C(=O)- | —CH₃ |
| | | | -CH₃ | |
| " | " | " | OH | —CH₂—CN |
| " | " | " | OH | —C≡C—H |
| [decalone structure] | " | " | " | " |
| " | " | " | " | —C≡C—CH₃ |
| " | " | " | " | —C≡C—CH₂CH₃ |
| " | " | " | " | —C≡C—Cl |
| " | " | " | " | —CH₂—C≡C—H |
| " | (CH₃)₂N-CH₂CH₂-S-C₆H₄- | " | —C≡C—H | —OH |
| " | " | " | HOCH₂-C(=O)- | —H |
| [isoxazole-fused decalin structure] | CH₃S-C₆H₄- | " | " | " |
| " | " | " | —C≡C—H | —OH |
| " | " | " | OH | —C≡C—H |
| " | " | " | " | —C≡C—CH₃ |
| " | " | " | " | —C≡C—CH₂—CH₃ |
| " | " | " | " | —C≡C—Cl |
| " | " | " | " | —CH₂—C≡C—H |
| " | CH₃S-C₆H₄- | CH₂CH₃ | " | —C≡C—H |

-continued
| A-B structure | | $R_1$ | $R_2$ | $R_3$ | $R_4$ |
|---|---|---|---|---|---|
| 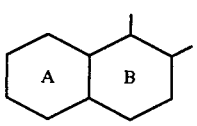 | | " | " | " | —C≡C—CH₃ |
| 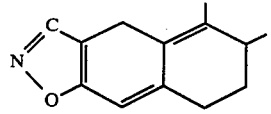 | 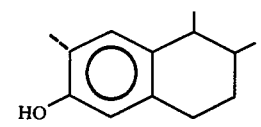 | CH₂CH₃ | OH | | —CH₂—C≡—H |
| " | " | " | " | | —CH₂—CH=CH₂ |
| " | " | " | 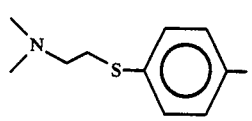 | | —CH₃ |
| " | " | " | 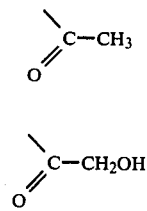 | | —H |
| " | " | " | " | —C≡C—H | —OH |
| " | 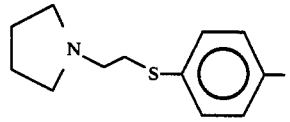 | CH₃ | OH | | —C≡C—H |
| " | " | " | " | | —C≡C—CH₃ |
| " | " | " | " | | —C≡C—Cl |
| 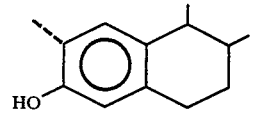 | " | " | " | | —C≡C—CH₂CH₃ |
| " | " | " | " | | —CH₂—C≡C—H |
| " | " | " | " | | —CH₂—CH=CH₂ |
| " | " | " | " | —C≡C—H | —OH |
| " | 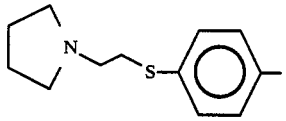 | " | 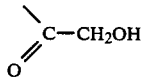 | | —H |
| " | " | " | 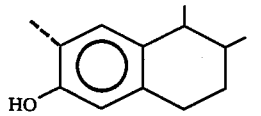 | | —CH₃ |
| 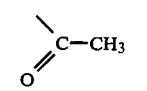 | " | " | 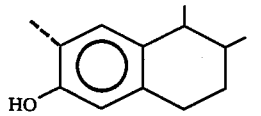 | | —H |

-continued
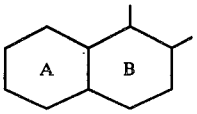
| | $R_1$ | $R_2$ | $R_3$ | $R_4$ |
|---|---|---|---|---|
| " | 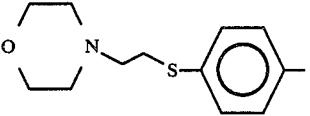 | " | " | " |
| " | " | " | " | —CH$_3$ |
| " | " | " | 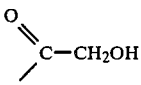 | —H |
| " | " | " | —C≡C—H | —OH |
| " | " | " | OH | —C≡C—H |
| " | " | " | " | —C≡C—CH$_3$ |
| " | " | " | " | —C≡C—Cl |
| 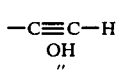 | | | | |
| " | 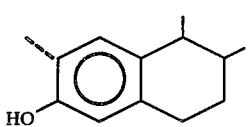 | " | " | —C≡C—CH$_2$CH$_3$ |
| " | " | " | " | —CH$_2$—C≡C—H |
| " | " | " | " | —CH$_2$—CH=CH$_2$ |
| " | 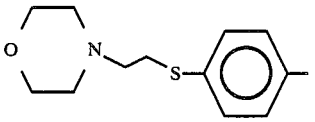 | " | " | —C≡C—H |
| " | " | " | " | —C≡C—CH$_3$ |
| " | " | " | " | —CH$_2$—C≡C—H |
| 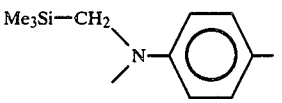 | 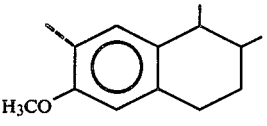 | CH$_2$CH$_3$ | OH | —CH$_2$—C≡C—H |
| " | " | " | " | —CH$_2$—CH=CH$_2$ |
| " | " | " | " | —CH$_3$ |
| " | " | " | 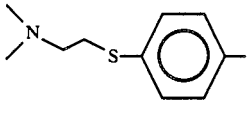 | —H |
| " | " | " | 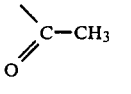 | —H |
| " | " | " | —C≡C—H | —OH |
| " | 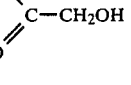 | CH$_3$ | OH | —C≡C—H |
| " | " | " | " | —C≡C—CH$_3$ |

-continued
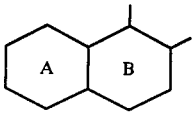
| | R₁ | R₂ | R₃ | R₄ |
|---|---|---|---|---|
| 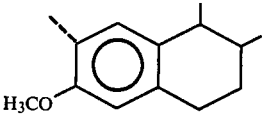 | | " | " | " | —C≡C—Cl |
| " | " | " | " | —C≡C—CH₂CH₃ |
| " | " | " | " | —CH₂—C≡C—H |
| " | " | " | " | —CH₂—CH=CH₂ |
| " | " | " | —C≡C—H | —OH |
| " | 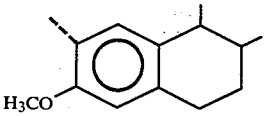 | " | 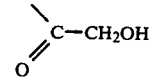 | —H |
| " | " | " | 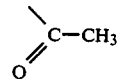 | —CH₃ |
| 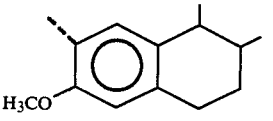 | " | " | 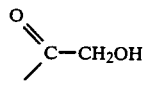 | —H |
| " | 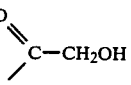 | " | " | " |
| " | " | " | " | —CH₃ |
| " | " | " | 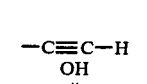 | —H |
| " | " | " | —C≡C—H OH | —OH |
| " | " | " | " | —C≡C—H |
| " | " | " | " | —C≡C—CH₃ |
| 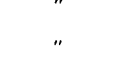 | " | " | " | —C≡C—Cl |
| " |  | " | " | —C≡C—CH₂CH₃ |
| " | " | " | " | —CH₂—C≡C—H |
| " | " | " | " | —CH₂—CH=CH₂ |
| " |  | " | " | —C≡C—H |
| " | " | " | " | —C≡C—CH₃ |

-continued
| 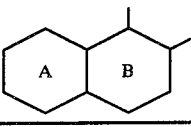 | | R₁ | R₂ | R₃ | R₄ |
|---|---|---|---|---|---|
| " | | " | " | " | —CH₂—C≡—H |
| 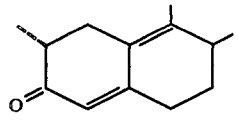 | | 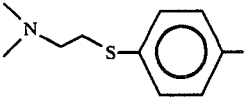 | CH₂CH₃ | OH | —CH₂—C≡—H |
| " | | " | " | " | —CH₂—CH=CH₂ |
| " | | " | " | 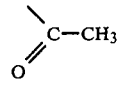 | —CH₃ |
| " | | " | " | 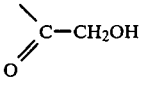 | —H |
| " | | " | " | —C≡C—H | —OH |
| " | | 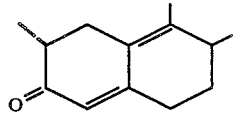 | CH₃ | OH | —C≡C—H |
| " | | " | " | " | —C≡C—CH₃ |
| " | | " | " | " | —C≡C—Cl |
| 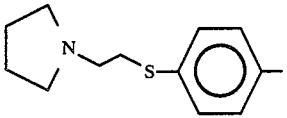 | | | | | |
| " | | " | " | " | —C≡C—CH₂CH₃ |
| " | | " | " | " | —CH₂—C≡C—H |
| " | | " | " | " | —CH₂—CH=CH₂ |
| " | | " | " | —C≡C—H | —OH |
| " | |  | " | 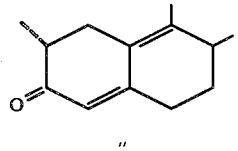 | —H |
| " | | " | " | 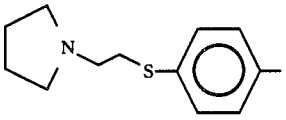 | —CH₃ |
|  | | " | " | 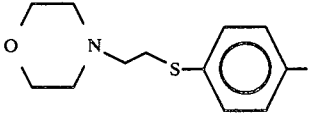 | —H |
| " | | morpholine-N-CH₂CH₂-S-C₆H₄- | " | " | " |
| " | | " | " | " | —CH₃ |

-continued
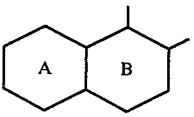
| | $R_1$ | $R_2$ | $R_3$ | $R_4$ |
|---|---|---|---|---|
| " | " | " | ![O=C-CH2OH with CH3] | —H |
| " | " | " | —C≡C—H | —OH |
| " | " | " | OH | —C≡C—H |
| " | " | " | " | —C≡C—CH$_3$ |
| 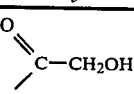 | " | " | " | —C≡C—Cl |
| " | 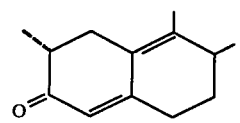 | " | " | —C≡C—CH$_2$CH$_3$ |
| " | " | " | " | —CH$_2$—C≡C—H |
| " | " | " | " | —CH$_2$—CH=CH$_2$ |
| " | 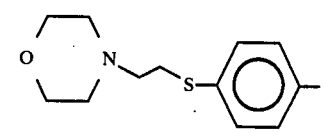 | " | " | —C≡C—H |
| " | " | " | " | —C≡C—CH$_3$ |
| " | " | " | " | —CH$_2$—C≡C—H |
| " | 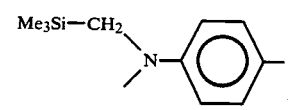 | CH$_2$CH$_3$ | OH | —CH$_2$—C≡C—H |
| " | " | " | " | —CH$_2$—CH=CH$_2$ |
| " | " | " | " | —CH$_3$ |
| " | " | " | ![C(=O)CH3] | |
| " | " | " | ![C(=O)CH2OH] | —H |
| " | " | " | —C≡C—H | —OH |
| " | 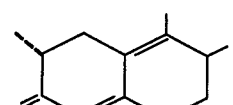 | CH$_3$ | OH | —C≡C—H |
| " | " | " | " | —C≡C—CH$_3$ |
| 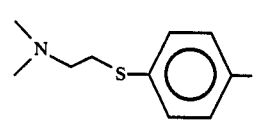 | " | " | " | —C≡C—Cl |
| " | " | " | " | —C≡C—CH$_2$CH$_3$ |
| " | " | " | " | —CH$_2$—C≡C—H |

| ![A-B ring] | R₁ | R₂ | R₃ | R₄ |
|---|---|---|---|---|
| " | " | " | " | —CH₂—CH=CH₂ |
| " | " | " | —C≡C—H | —OH |
| " | [pyrrolidine-N-CH₂CH₂-S-C₆H₄-] | " | —C(=O)—CH₂OH | —H |
| " | " | " | —C(=O)—CH₃ | —CH₃ |
| [decalone structure] | " | " | —C(=O)—CH₃ | —H |
| " | [morpholine-N-CH₂CH₂-S-C₆H₄-] | " | " | " |
| " | " | " | " | —CH₃ |
| " | " | " | —C(=O)—CH₂OH | —H |
| " | " | " | —C≡C—H | —OH |
| " | " | " | OH | —C≡C—H |
| " | " | " | " | —C≡C—CH₃ |
| " | " | " | " | —C≡C—Cl |
| [decalone structure] | " | " | " | —C≡C—CH₂CH₃ |
| " | [morpholine-N-CH₂CH₂-S-C₆H₄-] | " | " | " |
| " | " | " | " | —CH₂—C≡C—H |
| " | " | " | " | —CH₂—CH=CH₂ |
| " | [Me₃Si—CH₂—N(CH₃)—C₆H₄-] | " | " | —C≡C—H |
| " | " | " | " | —C≡C—CH₃ |
| " | " | " | " | —CH₂—C≡C—H |

| Core (A/B) | R₁ | R₂ | R₃ | R₄ |
|---|---|---|---|---|
| 3-methyl-6-hydroxy tetrahydronaphthalene (with methyl substituents) | Me₃Si—CH₂—N(CH₃)—(p-tolyl) | CH₃ | —C≡C—H | —OH |
| " | " | " | —C(=O)—CH₂OH | —H |
| " | Me₃Si—CH₂—N⁺(O⁻)(CH₃)—(p-tolyl) | " | OH | —C≡C—H |
| " | " | " | " | —C≡C—CH₃ |
| " | " | " | " | —CH₂—C≡C—H |
| " | " | " | —C≡C—H | —OH |
| " | " | " | —C(=O)—CH₂OH | —H |
| 3-methyl-6-hydroxy tetrahydronaphthalene | N,N-dimethyl-5-methyl-1-naphthylamine | " | OH | —C≡C—CH₃ |
| " | " | " | " | —CH₂—C≡C—H |
| " | N,N-dimethyl-6-methyl-2-naphthylamine | " | " | —C≡C—H |
| " | " | " | " | —C≡C—CH₃ |
| " | " | " | " | —C≡C—Cl |
| " | " | " | " | —CH₂—C≡C—H |
| " | " | " | —C≡C—H | —OH |
| " | " | " | —C(=O)—CH₂OH | —H |
| 3-methyl-6-hydroxy tetrahydronaphthalene | N,N-dimethyl-6-methyl-2-naphthylamine N-oxide | " | " | " |
| " | " | " | —C≡C—H | —OH |
| " | " | " | —OH | —C≡C—H |
| " | " | " | " | —C≡C—CH₃ |
| " | " | " | " | —C≡C—Cl |
| " | " | " | " | —CH₂—C≡C—H |

-continued
| Structure | R₁ | R₂ | R₃ | R₄ |
|---|---|---|---|---|
| 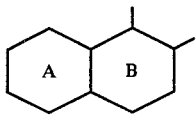 | Me₃SiCH₂— | " | " | —C≡C—H |
| " | " | " | " | —C≡C—CH₃ |
| " | " | " | " | —CH₂—C≡C—H |
| " | " | " | —C≡C—H | —OH |
| 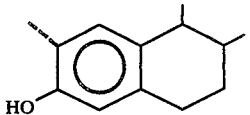 | " | " | " | " |
| " | " | " | OH | —C≡C—H |
| " | " | " | " | —C≡C—CH₃ |
| 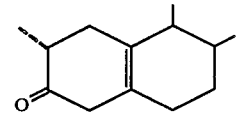 | 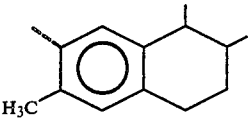 | CH₃ | —C≡C—H | —OH |
| " | " | " | O=C—CH₂OH | —H |
| " | 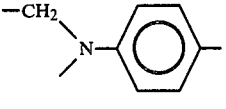 | " | OH | —C≡C—H |
| " | " | " | " | —C≡C—CH₃ |
| " | " | " | " | —CH₂—C≡C—H |
| " | " | " | —C≡C—H | —OH |
| " | " | " | O=C—CH₂OH | —H |
| 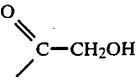 | 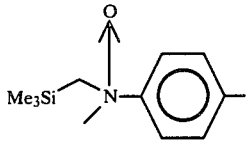 | " | OH | —C≡C—CH₃ |
| " | " | " | " | —CH₂—C≡C—H |
| " | " | " | " | —C≡C—H |
| " | 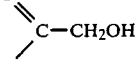 | " | " | " |
| " | " | " | " | —C≡C—CH₃ |
| " | " | " | " | —C≡C—Cl |
| " | " | " | " | —CH₂—C≡C—H |
| " | " | " | —C≡C—H | —OH |

-continued
| | R₁ | R₂ | R₃ | R₄ |
|---|---|---|---|---|
| 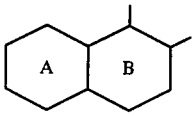 | " | " | 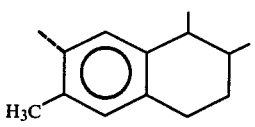—C(=O)—CH₂OH | —H |
| " | 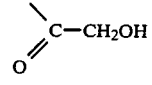 | " | " | " |
| " | " | " | —C≡C—H<br>—OH | —OH<br>—C≡C—H<br>—C≡C—CH₃<br>—C≡C—Cl<br>—CH₂—C≡C—H |
| 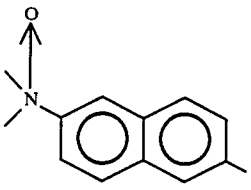 | Me₃SiCH₂— | " | " | —C≡C—H |
| "<br>" | "<br>" | "<br>" | "<br>—C≡C—H | —C≡C—CH₃<br>—CH₂—C≡C—H<br>—OH |
| 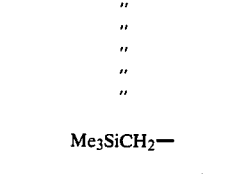 | " | " | " | " |
| "<br>" | "<br>" | "<br>" | OH<br>" | —C≡C—H<br>—C≡C—CH₃ |
|  | 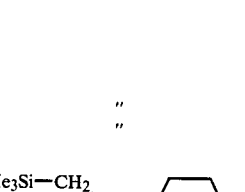 | CH₃ | —C≡C—H | —OH |
| " | " | " | —C(=O)—CH₂OH | —H |
| " | 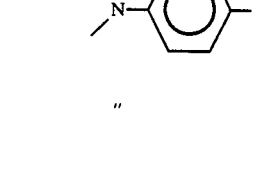 | " | OH | —C≡C—H |
| "<br>" | "<br>" | "<br>" | "<br>—C≡C—H | —C≡C—CH₃<br>—CH₂—C≡C—H<br>—OH |
| " | " | " | —C(=O)—CH₂OH | —H |

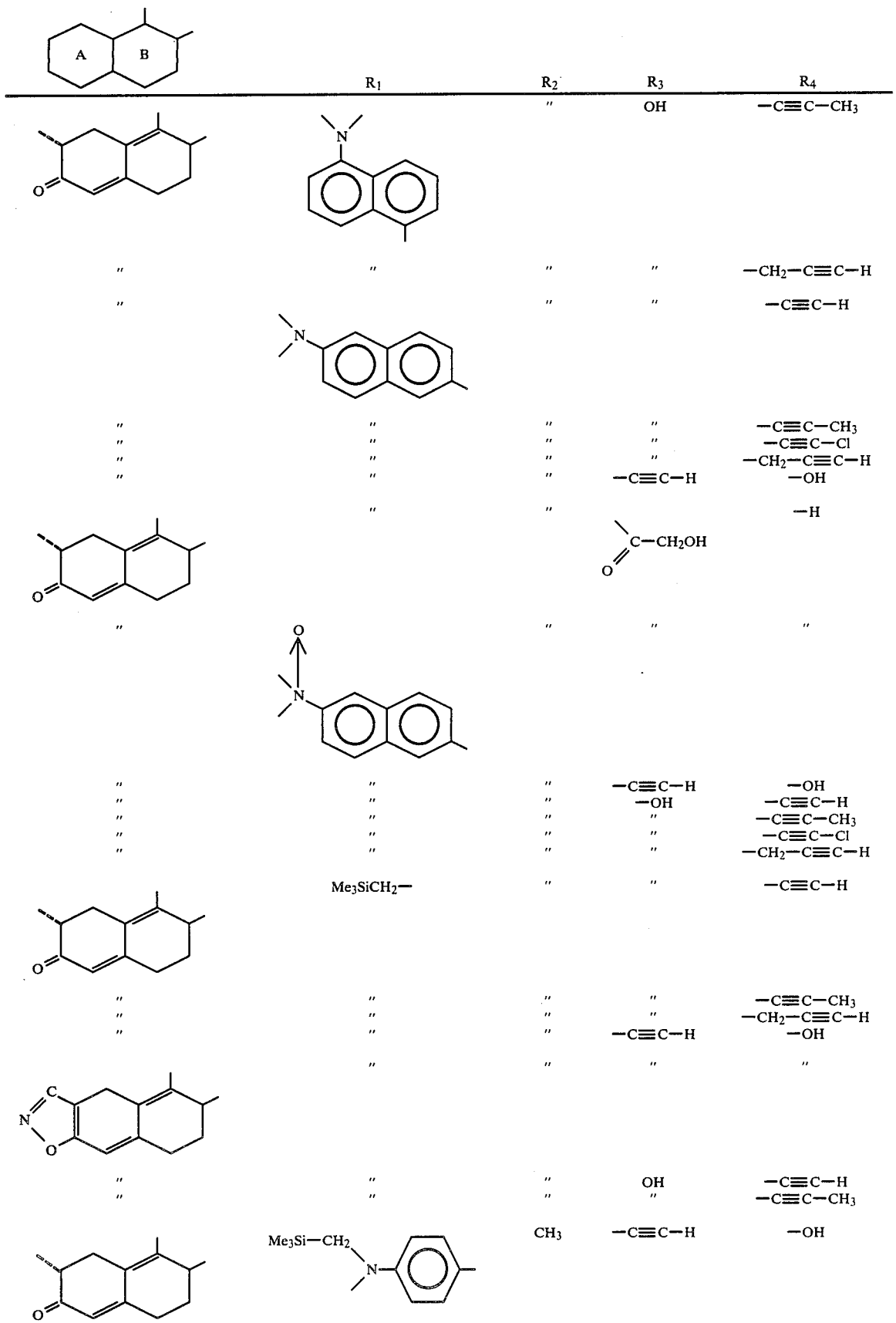

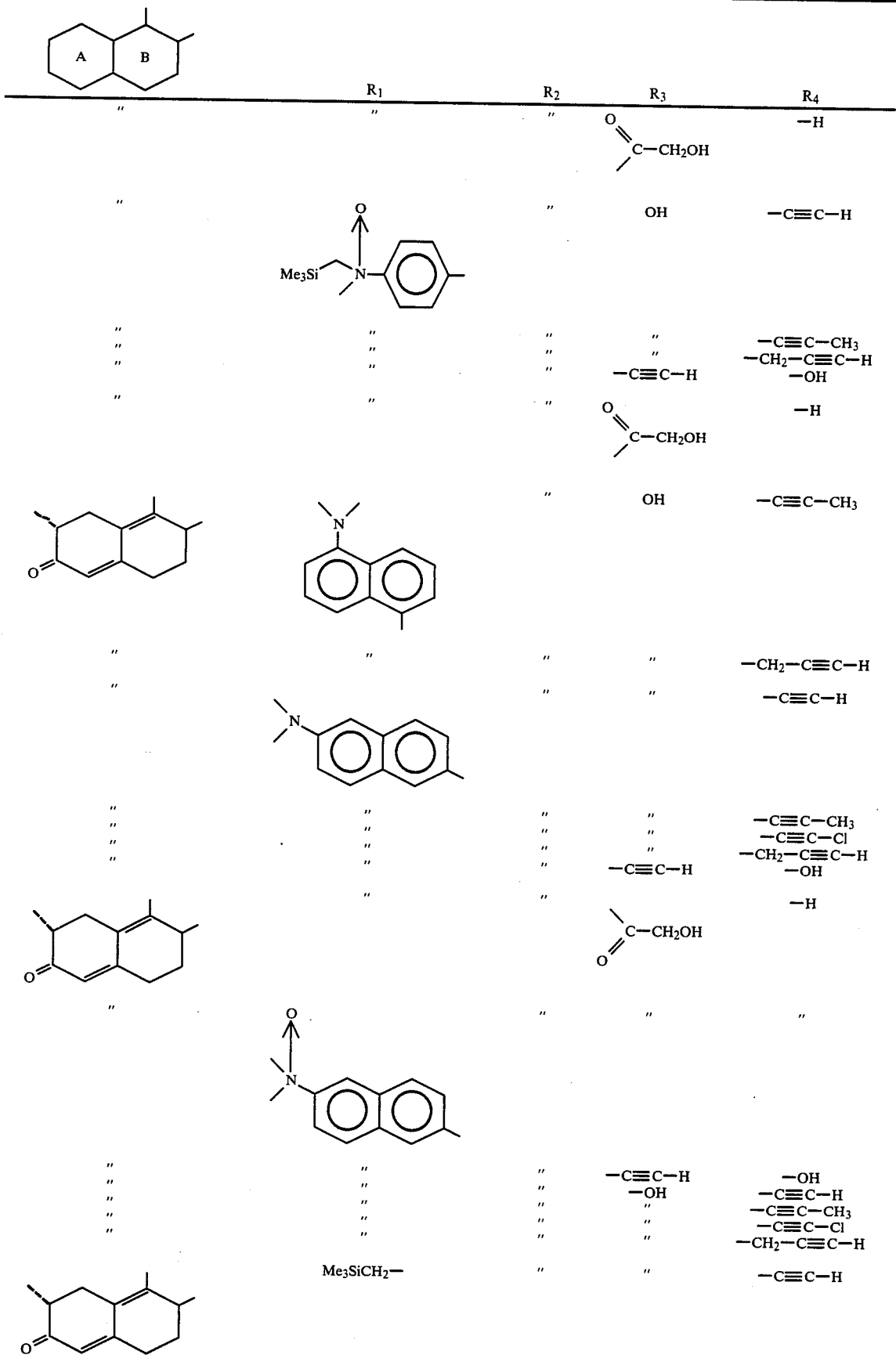

-continued
| | R₁ | R₂ | R₃ | R₄ |
|---|---|---|---|---|
| 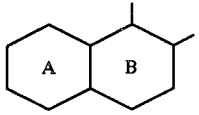 | | | | |
| " | " | " | " | —C≡C—CH₃ |
| " | " | " | " | —CH₂—C≡C—H |
| " | " | " | —C≡C—H | —OH |
| 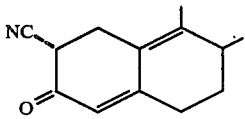 | " | " | " | " |
| " | " | " | OH | —C≡C—H |
| " | " | " | " | —C≡C—CH₃ |
| 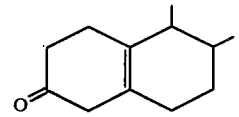 | Me₃SiCH₂— | CH₃ | OH | —CH₂—C≡C—H |
| " | " | CH₂CH₃ | —C≡C—H | —OH |
| " | " | " | OH | —C≡C—H |
| " | " | " | " | —C≡C—CH₃ |
| " | " | " | " | —CH₂—C≡C—H |
| " | " | " | " | —C≡C—CH₃ |
| 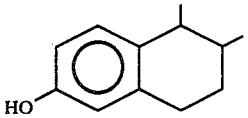 | 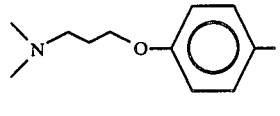 | | | |
| " | " | " | 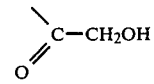 | —H |
| " | 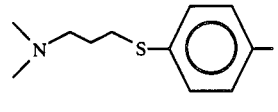 | " | " | " |
| " | " | " | OH | —C≡C—H |
| " | " | " | " | —C≡C—CH₃ |
| " | " | " | " | —CH₂—C≡C—H |
| " | " | " | " | —CH₂—CH=CH₂ |
| " | " | " | " | —CH₂CN |
| 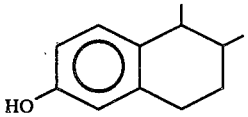 | " | " | " | |
| " | " | " | —C≡C—H | —OH |
| " | " | " | 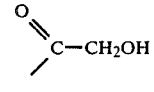 | —H |
| " | " | " | 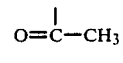 | —CH₃ |
| " | " | " | OH | —H |

-continued
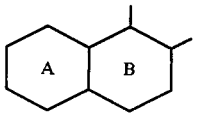
| | R₁ | R₂ | R₃ | R₄ |
|---|---|---|---|---|
| " | 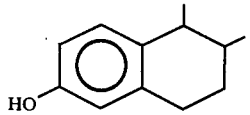 | " | OH | —C≡C—H |
| " | " | " | " | —C≡C—CF₃ |
| " | " | " | " | —C≡C—CH₂CH₃ |
| 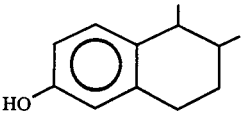 | | | | |
| " | " | " | " | —C≡C—Cl |
| " | " | " | " | —CH₂—C≡C—H |
| " | " | " | —C≡C—H | —OH |
| " | " | " | 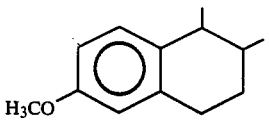 | —H |
| " | " | " |  | —CH₃ |
| " | " | CH₂CH₃ | OH | —C≡C—H |
| " | " | " | " | —C≡C—CH₃ |
| 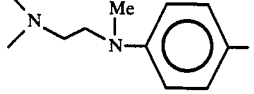 | | | | |
| " | " | " | " | —CH₂—C≡C—H |
|  | Me₃SiCH₂— | CH₃ | OH | —CH₂—C≡C—H |
| " | " | CH₂CH₃ | —C≡C—H | —OH |
| " | 41 | " | OH | —C≡C—H |
| " | " | " | " | —C≡C—CH₃ |
| " | " | " | " | —CH₂—C≡C—H |
| " | " | " | " | —C≡C—CH₃ |
| 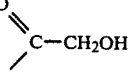 | 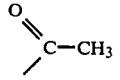 | | | |
| " | " | " |  | —H |
| " | 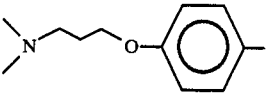 | " | " | " |
| " | " | " | OH | —C≡C—H |
| " | " | " | " | —C≡C—CH₃ |
| " | " | " | " | —CH₂—C≡C—H |

-continued

| 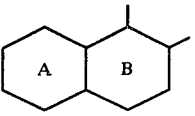 | R₁ | R₂ | R₃ | R₄ |
|---|---|---|---|---|
| " | " | " | " | —CH₂—CH=CH₂ |
| " | " | " | " | —CH₂CN |
| 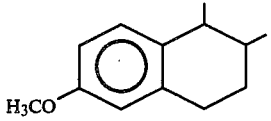 | | | | |
| " | " | " | —C≡C—H | —OH |
| " | " | " | $\overset{O}{\underset{}{C}}$—CH₂OH | —H |
| " | " | " | $\overset{O}{\underset{}{C}}$—CH₃ | —CH₃ |
| " | " | " | OH | —H |
| " | 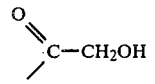 | " | OH | —C≡C—H |
| " | " | " | " | —C≡C—CF₃ |
| " | " | " | " | —C≡C—CH₂CH₃ |
| 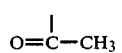 | | | | |
| " | " | " | " | —C≡C—Cl |
| " | " | " | " | —CH₂—C≡C—H |
| " | " | " | —C≡C—H | —OH |
| " | " | " | $\overset{O}{\underset{}{C}}$—CH₂OH | —H |
| " | " | " | $\overset{O}{\underset{}{C}}$—CH₃ | —CH₃ |
| " | " | CH₂CH₃ | OH | —C≡C—H |
| " | " | " | " | —C≡C—CH₃ |
| 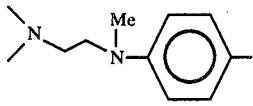 | | | | |
| " | " | " | " | —CH₂—C≡C—H |
| " | Me₃SiCH₂— | CH₃ | OH | —CH₂—C≡C—H |
| 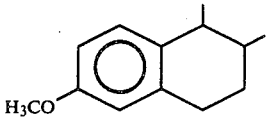 | | | | |
| " | " | CH₂CH₃ | —C≡C—H | —OH |
| " | " | " | OH | —C≡C—H |
| " | " | " | " | —C≡C—CH₃ |
| " | " | " | " | —CH₂—C≡C—H |

-continued
| | $R_1$ | $R_2$ | $R_3$ | $R_4$ |
|---|---|---|---|---|
| 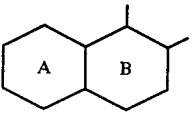 | 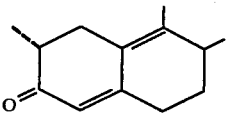 | " | " | —C≡C—CH$_3$ |
| " | " | " | 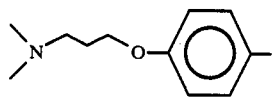 | —H |
| " | 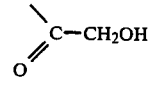 | " | " | " |
| " | " | " | OH | —C≡C—H |
| " | " | " | " | —C≡C—CH$_3$ |
| " | " | " | " | —CH$_2$—C≡C—H |
| " | " | " | " | —CH$_2$—CH=CH$_2$ |
| 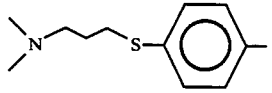 | " | " | " | —CH$_2$CN |
| " | " | " | —C≡C—H | —OH |
| " | " | " | 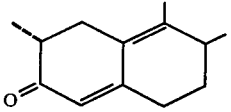 | —H |
| " | " | " | 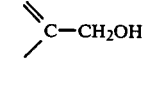 | —CH$_3$ |
| " | " | " | OH | —H |
| " | " | " | OH | —C≡C—H |
| " | 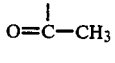 | " | " | " |
| " | " | " | " | —C≡C—CF$_3$ |
| " | " | " | " | —C≡C—CH$_2$CH$_3$ |
| 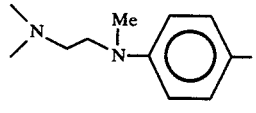 | " | " | " | —C≡C—Cl |
| " | " | " | " | —CH$_2$—C≡C—H |
| " | " | " | —C≡C—H | —OH |
| " | " | " | 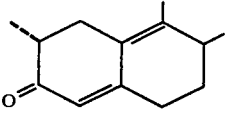 | —H |
| " | " | " | 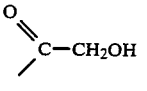 | —CH$_3$ |

| Structure | $R_1$ | $R_2$ | $R_3$ | $R_4$ |
|---|---|---|---|---|
| " | " | $CH_2CH_3$ | OH | $-C\equiv C-H$ |
| " | " | " | " | $-C\equiv C-CH_3$ |
| [dimethyl-dione decalin] | " | " | " | $-CH_2-C\equiv C-H$ |
| [dicyano-dione decalin] | $Me_3SiCH_2-$ | $CH_3$ | OH | $-CH_2-C\equiv C-H$ |
| " | " | $CH_2CH_3$ | $-C\equiv C-H$ | $-OH$ |
| " | " | " | OH | $-C\equiv C-H$ |
| " | " | " | " | $-C\equiv C-CH_3$ |
| " | " | " | " | $-CH_2-C\equiv C-H$ |
| [dimethyl-dione decalin with Me] | " | $\text{Me}_2N-CH_2CH_2CH_2-O-C_6H_4-$ | " | $-C\equiv C-CH_3$ |
| " | " | " | " | $-H$ |
|  |  |  | $\underset{O}{\overset{}{C}}-CH_2OH$ |  |
| " | " | $\text{Me}_2N-CH_2CH_2CH_2-S-C_6H_4-$ | " | " |
| " | " | " | OH | $-C\equiv C-H$ |
| " | " | " | " | $-C\equiv C-CH_3$ |
| " | " | " | " | $-CH_2-C\equiv C-H$ |
| " | " | " | " | $-CH_2-CH=CH_2$ |
| " | " | " | " | $-CH_2CN$ |
| [dimethyl-dione decalin] | " | " | " | $-C\equiv C-H$ |
| " | " | " | $-C\equiv C-H$ | $-OH$ |
| " | " | " | " | $-H$ |
|  |  |  | $\underset{O}{\overset{}{C}}-CH_2OH$ |  |
| " | " | " | " | $-CH_3$ |
|  |  |  | $O=\overset{|}{C}-CH_3$ |  |
| " | " | " | OH | $-H$ |
| " | " | $\text{Me}_2N-CH_2CH_2-N(Me)-C_6H_4-$ | OH | $-C\equiv C-H$ |
| " | " | " | " | $-C\equiv C-CF_3$ |

4,547,493
-continued
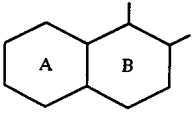
| A-B ring system | $R_1$ | $R_2$ | $R_3$ | $R_4$ |
|---|---|---|---|---|
| | " | " | " | —C≡C—CH₂CH₃ |
| 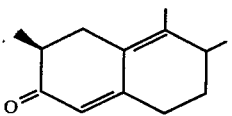 | | | | |
| " | " | " | " | —C≡C—Cl |
| " | " | " | " | —CH₂—C≡C—H |
| " | " | " | —C≡C—H | —OH |
| " | " | " | 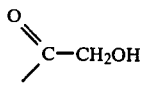 | —H |
| " | " | " | 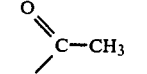 | —CH₃ |
| " | " | CH₂CH₃ | OH | —C≡C—H |
| " | " | " | " | —C≡C—CH₃ |
| 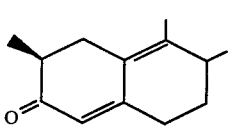 | | | | |
| " | " | " | " | —CH₂—C≡C—H |
| " | 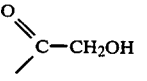 | CH₂CH₃ | —C≡C—H | —OH |
| " | " | " | 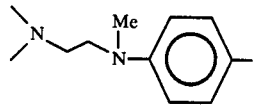 | —H |
| " | 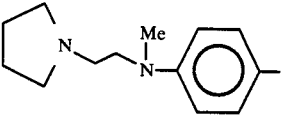 | CH₃ | OH | —C≡C—H |
| " | " | " | " | —C≡C—CH₃ |
| " | " | " | " | —CH₂—C≡C—H |
| " | " | " | —C≡C—H | —OH |
| " | " | " | 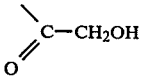 | —H |
| 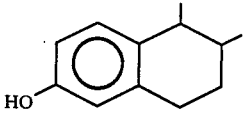 | 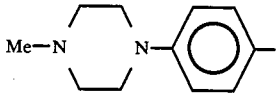 | " | " | " |
| " | " | " | —C≡C—H | —OH |
| " | " | " | OH | —C≡C—H |
| " | " | " | " | —CH₂—C≡C—H |
| " | " | " | " | —CH₂—CH=CH₂ |
| " | " | " | " | —CH₂CN |

-continued
| A B | | R₁ | R₂ | R₃ | R₄ |
|---|---|---|---|---|---|
| 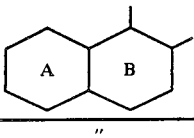 | | 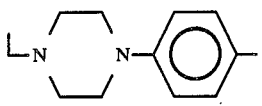 | " | " | —C≡C—H |
| | | " | " | " | —C≡C—CH₃ |
| 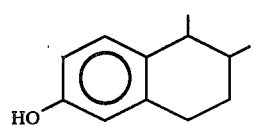 | | " | " | " | —CH₂—C≡C—H |
| " | | " | " | " | —CH₂—CH=CH₂ |
| " | | " | " | " | —CH₂—CN |
| " | | " | " | —C≡C—H | —OH |
| " | | 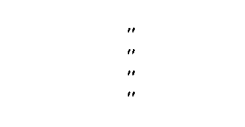 | " | —OH | —C≡C—H |
| " | | " | " | " | —C≡C—CH₃ |
| " | | " | " | " | —CH₂—C≡C—H |
| 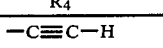 | | " | " | —C≡C—H | —OH |
| " | | " | " | 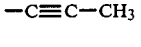 | —H |
| " | |  | " | " | " |
| " | | " | " | —C≡C—H | OH |
| " | | " | " | OH | —C≡C—H |
| " | | " | " | " | —C≡C—CH₃ |
| 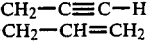 | | 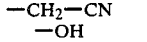 | CH₂CH₃ | —C≡C—H | —OH |
| " | | " | " | 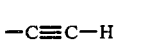 | —H |
| " | | 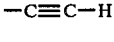 | CH₃ | OH | —C≡C—H |
| " | | " | " | " | —C≡C—CH₃ |
| " | | " | " | " | —CH₂—C≡C—H |

-continued

| ![AB ring system with methyl groups] | R₁ | R₂ | R₃ | R₄ |
|---|---|---|---|---|
| " | " | " | —C≡C—H | —OH |
| " | " | " | >C(=O)—CH₂OH | —H |
| ![6-methoxy tetralin with methyl groups] | Me—N(piperazine)N—C₆H₄— | " | " | " |
| " | " | " | —C≡C—H / OH | —OH |
| " | " | " | " | —C≡C—H |
| " | " | " | " | —CH₂—C≡C—H |
| " | " | " | " | —CH₂—CH=CH₂ |
| " | " | " | " | —CH₂CN |
| " | Et—N(piperazine)N—C₆H₄— | " | " | —C≡C—H |
| ![6-methoxy tetralin with methyl groups] | " | " | " | —C≡C—CH₃ |
| " | " | " | " | —CH₂—C≡C—H |
| " | " | " | " | —CH₂—CH=CH₂ |
| " | " | " | " | —CH₂—CN |
| " | " | " | —C≡C—H | —OH |
| " | " | " | —OH | —C≡C—H |
| " | ![N-methyl tetrahydroquinoline propyl] | " | " | " |
| " | " | " | " | —C≡C—CH₃ |
| " | " | " | " | —CH₂—C≡C—H |
| ![6-methoxy tetralin with methyl groups] | " | " | " | " |
| " | " | " | —C≡C—H | —OH |
| " | " | " | >C(=O)—CH₂OH | —H |
| " | Me₂N—CH₂CH₂CH₂—N(Me)—C₆H₄— | " | " | " |
| " | " | " | —C≡C—H / OH | OH |
| " | " | " | " | —C≡C—H |
| " | " | " | " | —C≡C—CH₃ |

-continued
| A-B structure | R₁ | R₂ | R₃ | R₄ |
|---|---|---|---|---|
| 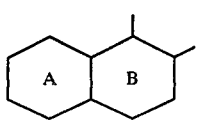 | 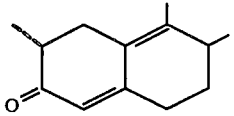 | CH₂CH₃ | —C≡C—H | —OH |
| " | " | " | 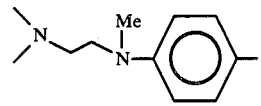 (COCH₂OH) | —H |
| " | 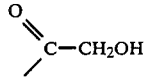 | CH₃ | OH | —C≡C—H |
| " | " | " | " | —C≡C—CH₃ |
| " | " | " | " | —CH₂—C≡C—H |
| " | " | " | —C≡C—H | —OH |
| " | " | " | 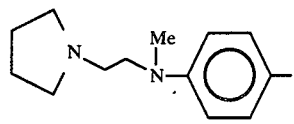 (COCH₂OH) | —H |
| 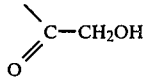 | 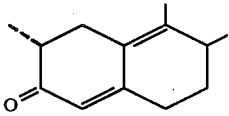 | " | " | " |
| " | " | " | —C≡C—H | —OH |
| " | " | " | OH | —C≡C—H |
| " | " | " | " | —CH₂—C≡C—H |
| " | " | " | " | —CH₂—CH=CH₂ |
| " | " | " | " | —CH₂CN |
| " | 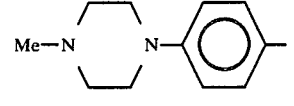 | " | " | —C≡C—H |
| " | " | " | " | —C≡C—CH₃ |
| 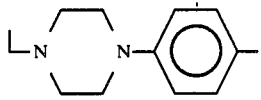 | " | " | " | —CH₂—C≡C—H |
| " | " | " | " | —CH₂—CH=CH₂ |
| " | " | " | " | —CH₂—CN |
| " | " | " | —C≡C—H | —OH |
| " | 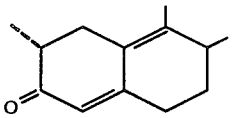 | " | —OH | —C≡C—H |
| " | " | " | " | —C≡C—CH₃ |

| | R₁ | R₂ | R₃ | R₄ |
|---|---|---|---|---|
| 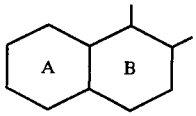 | " | " | " | —CH₂—C≡C—H |
| " | " | " | —C≡C—H | —OH |
| " | " | " | (C(=O)—CH₂OH) | —H |
| " | 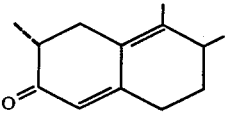 | " | " | " |
| " | " | " | —C≡C—H | OH |
| " | " | " | OH | —C≡C—H |
| " | " | " | " | —C≡C—CH₃ |
| 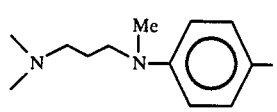 | 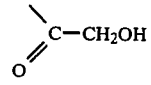 | CH₂CH₃ | —C≡C—H | —OH |
| " | " | " | (C(=O)—CH₂OH) | —H |
| " | 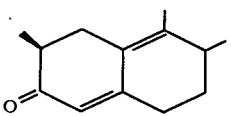 | CH₃ | OH | —C≡C—H |
| " | " | " | " | —C≡C—CH₃ |
| " | " | " | " | —CH₂—C≡C—H |
| " | " | " | —C≡C—H | —OH |
| " | " | " | (C(=O)—CH₂OH) | —H |
| 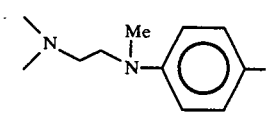 | 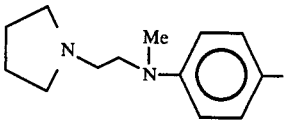 | " | " | " |
| " | " | " | —C≡C—H | —OH |
| " | " | " | OH | —C≡C—H |
| " | " | " | " | —CH₂—C≡C—H |
| " | " | " | " | —CH₂—CH=CH₂ |
| " | " | " | " | —CH₂CN |
| " | 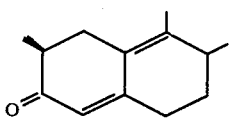 | " | " | —C≡C—H |

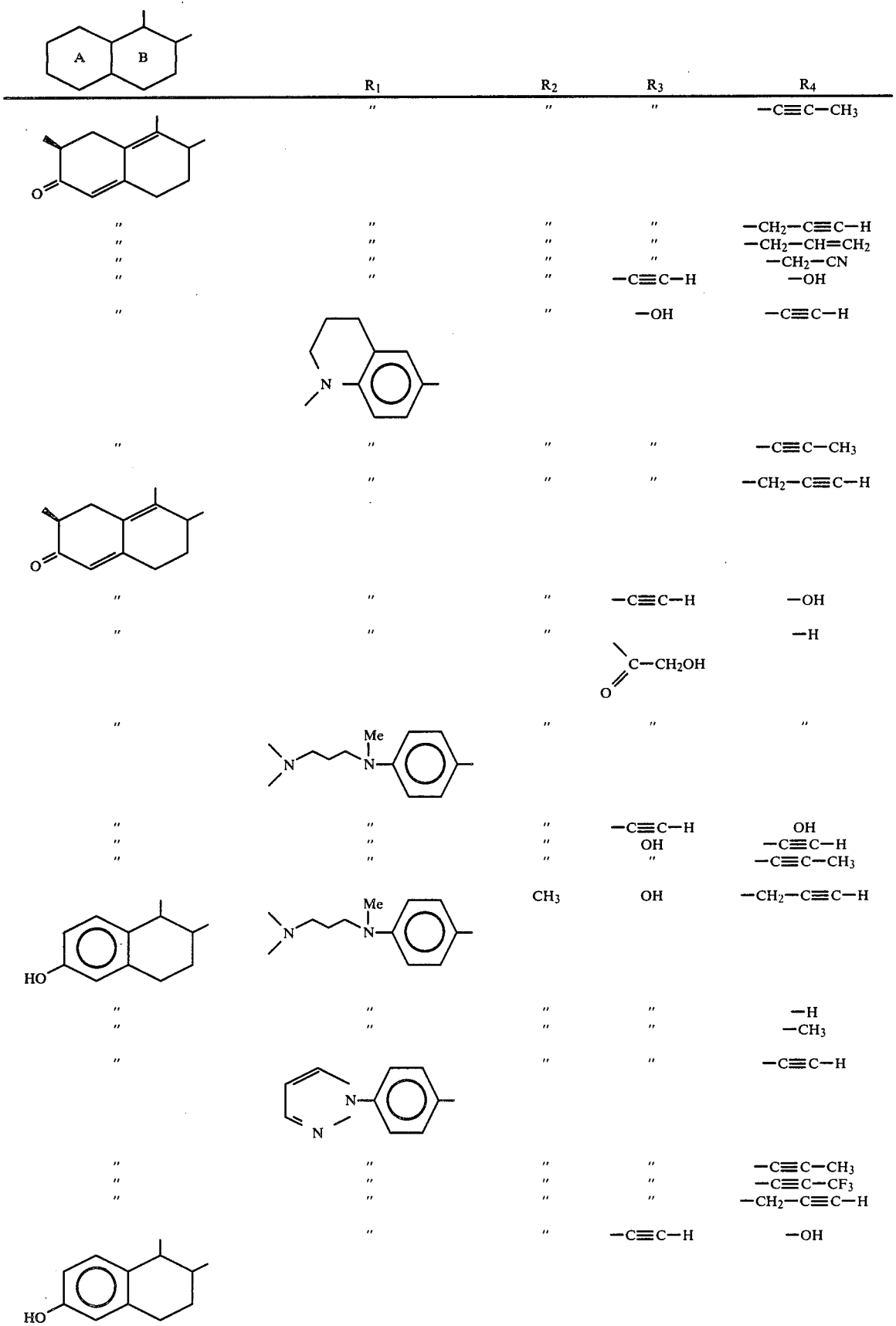
| | R₁ | R₂ | R₃ | R₄ |
|---|---|---|---|---|
| | " | " | " | —C≡C—CH₃ |
| | " | " | " | —CH₂—C≡C—H |
| | " | " | " | —CH₂—CH=CH₂ |
| | " | " | " | —CH₂—CN |
| | " | " | —C≡C—H | —OH |
| | " | | " | —OH | —C≡C—H |
| | " | | " | " | —C≡C—CH₃ |
| | " | | " | " | —CH₂—C≡C—H |
| | " | " | " | —C≡C—H | —OH |
| | " | " | " | >C(=O)—CH₂OH | —H |
| | " | | " | " | " |
| | " | " | " | —C≡C—H | OH |
| | " | " | " | OH | —C≡C—H |
| | " | " | " | " | —C≡C—CH₃ |
| | | CH₃ | OH | —CH₂—C≡C—H |
| | " | " | " | " | —H |
| | " | " | " | " | —CH₃ |
| | " | | " | " | —C≡C—H |
| | " | " | " | " | —C≡C—CH₃ |
| | " | " | " | " | —C≡C—CF₃ |
| | " | " | " | " | —CH₂—C≡C—H |
| | " | " | " | —C≡C—H | —OH |

-continued
| 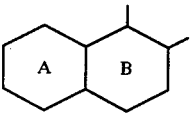 | R₁ | R₂ | R₃ | R₄ |
|---|---|---|---|---|
| " | 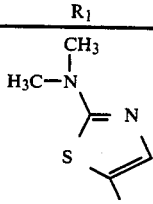 | " | OH | —C≡C—H |
| " | " | " | " | —C≡C—CH₃ |
| " | " | " | " | —C≡C—CF₃ |
| " | " | " | " | —CH₂—C≡C—H |
| " | " | " | —C≡C—H | —OH |
| " | " | " | —C≡C—CH₃ | —OH |
| 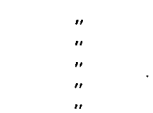 | 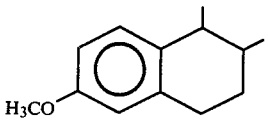 | CH₃ | OH | —CH₂—C≡C—H |
| " | " | " | " | —H |
| " | " | " | " | —CH₃ |
| " | 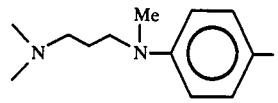 | " | " | —C≡C—H |
| " | " | " | " | —C≡C—CH₃ |
| " | " | " | " | —C≡C—CF₃ |
| " | " | " | " | —CH₂—C≡C—H |
| " | " | " | —C≡C—H | —OH |
| 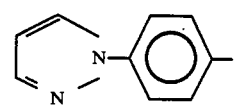 | " | " | " | " |
| " | 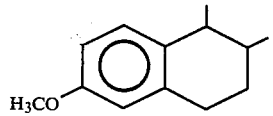 | " | OH | —C≡C—H |
| " | " | " | " | —C≡C—CH₃ |
| " | " | " | " | —C≡C—CF₃ |
| " | " | " | " | —CH₂—C≡C—H |
| " | " | " | —C≡C—H | —OH |
| " | " | " | —C≡C—CH₃ | —OH |
| 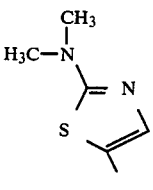 | 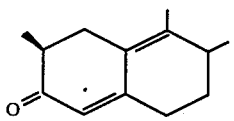 | CH₃ | OH | —CH₂—C≡C—H |
| " | " | " | " | —H |
| " | " | " | " | —CH₃ |
| " | 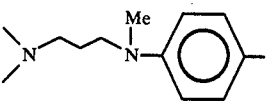 | " | " | —C≡C—H |
| " | " | " | " | —C≡C—CH₃ |
| " | " | " | " | —C≡C—CF₃ |

-continued

| [Structure with rings A, B] | R₁ | R₂ | R₃ | R₄ |
|---|---|---|---|---|
| | " | " | " | —CH₂—C≡C—H |
| | " | " | —C≡C—H | —OH |
| [Structure: bicyclic enone with methyl groups] | " | " | OH | —C≡C—H |
| | " | [Structure: H₃C—N(CH₃)—C(=N)—S— thiazole] | " | |
| | " | " | " | —C≡C—CH₃ |
| | " | " | " | —C≡C—CF₃ |
| | " | " | " | —CH₂—C≡C—H |
| | " | " | —C≡C—H | —OH |
| | " | " | —C≡C—CH₃ | —OH |
| [Structure: bicyclic enone with methyl groups] | " | [Structure: Me₂N—CH₂CH₂CH₂—N(Me)—C₆H₄—] | CH₃ | OH | —CH₂—C≡C—H |
| | " | " | " | —H |
| | " | " | " | —CH₃ |
| | " | " | " | —C≡C—H |
| | " | [Structure: pyridazine-N—C₆H₄—] | | | |
| | " | " | " | —C≡C—CH₃ |
| | " | " | " | —C≡C—CF₃ |
| | " | " | " | —CH₂—C≡C—H |
| | " | " | —C≡C—H | —OH |
| [Structure: bicyclic enone with methyl groups] | " | " | OH | —C≡C—H |
| | " | [Structure: H₃C—N(CH₃)—C(=N)—S— thiazole] | | | |
| | " | " | " | —C≡C—CH₃ |
| | " | " | " | —C≡C—CF₃ |
| | " | " | " | —CH₂—C≡C—H |
| | " | " | —C≡C—H | —OH |
| | " | " | —C≡C—CH₃ | —OH |

In the following examples there are described several preferred embodiments to illustrate the invention. However, it is to be understood that the invention is not intended to be limited to the specific embodiments.

2,2-dimethyl-11β-(4-dimethylaminophenyl)-17α-(prop-1-ynyl)-Δ$^{4,9}$-estradiene-17β-ol-3-one STEP A: 11β-(4-dimethylaminophenyl)-17α-(prop-1-ynyl)-17β-(2RS-tetrahydropyranyloxy)-Δ$^{4,9}$-estradiene-3-one 570 mg of p-toluene sulfonic acid were added to a solution of 1.075 g of 11β-(4-dimethylaminophenyl)-17α-(prop-1-ynyl)-Δ$^{4,9}$-estradiene-17β-ol-3-one [prepared in Example 1 of EPC Application Ser. No. 57,115] in 10 ml of tetrahydrofuran and 2 ml of 3,4-dihydro-pyran and the mixture was stirred at room temperature for one hour. 1 ml of triethylamine was added to the mixture which was then diluted with ethyl acetate. The organic phase was washed with aqueous saturated sodium bicabonate solution, dried and evaporated to dryness under reduced pressure to obtain 2 g of raw 11β-(4-dimethylaminophenyl)-17α-(prop-1-ynyl)-17β-(2RS-tetrahydropyranyloxy)-Δ$^{4,9}$-estradiene-3-one in the form of a yellow oil.

STEP B: 2,2-dimethyl-11β-(4-dimethylaminophenyl)-17α-(prop-1-ynyl)-17β-(2RS tetrahydropyranyloxy)-Δ$^{4,9}$-estradiene-3-one A solution of the product of Step A in 15 ml of anhydrous tetrahydrofuran was cooled to −60° C. and over 5 to 6 minutes 1 ml and 3 ml of a solution of 2M potassium tert.-butylate in tetrahydrofuran and 3 ml of a solution of 0.38 ml of methyl iodide in tetrahydrofuran were alternatively added thereto. The mixture was stirred for another five minutes and one ml of triethylamine was added thereto. The temperature was allowed to rise to room temperature and the mixture was evaporated to dryness to obtain 2,2-dimethyl-11β-(4-dimethylaminophenyl)-17α-(prop-1-ynyl)-17β-(2RS tetrahydropyranyloxy)-66$^{4,9}$-estradiene-3-one.

STEP C: 2,2-dimethyl-11β-(4-dimethylaminophenyl)-17α-(prop-1-ynyl)-Δ$^{4,9}$-estradiene-17β-ol-3-one 2.5 ml of 5N hydrochloric acid were added to a solution of the product of Step B in 10 ml of methanol and after standing for 15 minutes at room temperature, the mixture was diluted with water. The methanol was distilled off under reduced pressure and 2.5 ml of concentrated ammonium hydroxide were added thereto. The mixture was vacuum filtered and the product was washed with water and dissolved in ethyl acetate. The organic phase was dried and evaporated to dryness and the 1.5 g of residue were chromatographed over silica gel. Elution with a 9-1 benzene-ethyl acetate mixture yielded 990 mg of product which was crystallized from heptane. The mixture was vacuum filtered and the product was washed and dried to obtain 980 mg of 2,2-dimethyl-11β-(4-dimethylaminophenyl)-17α-(prop-1-ynyl)-Δ$^{4,9}$-estradiene-17β-ol-3-one melting at 170°-172° C.

A 2.2 g sample of the said product were dissolved in methylene chloride and the mixture was filtered. The filtrate was evaporated to dryness and the residue was dissolved in 10 ml of refluxing isopropyl ether and the solution cooled and crystallization was induced by scraping. The mixture stood at 5° C. and was then vacuum filtered. The product was washed and dried to obtain 1.88 g of the pure product melting at 171° C. and having a specific rotation of $[\alpha]_D^{20} = \pm 183.5° \pm 3.5°$ (c=1% in chloroform).

Analysis: C$_{31}$H$_{39}$NO$_2$; Calculated: %C 81.36; %H 8.59; %N 3.06; Found: 81.1; 8.8; 3.2.

EXAMPLE 2

11β-(4-dimethylaminophenyl)-17α-(prop-1-ynyl)-Δ$^{1,3,5(10)}$-estratriene-3,17β-diol and its 17β-acetoxy derivative 2 ml of 98% acetic anhydride and 1 ml of acetyl bromide were added dropwise under a nitrogen atmosphere to a solution of 2 g of 11β-(4-dimethylaminophenyl)-17α-(prop-1-ynyl)-Δ$^{4,9}$-estradiene-17β-ol-3-one in 20 ml of dry methylene chloride and the mixture was stirred at room temperature for one hour. 100 ml of aqueous sodium bicarbonate were added to the mixture which was stirred for 30 minutes. The decanted aqueous phase was extracted with methylene chloride and the combined organic phases were dried and evaporated to dryness. The 2.65 g of residue were dissolved in 25 ml of methanol and 2.6 ml of sodium hydroxide solution were added thereto at room temperature under nitrogen. The mixture was stirred for 45 minutes and was then acidified with 14 ml of 2N hydrochloric acid. The mixture was made alkaline by addition of ammonium hydroxide and was extracted with methylene chloride. The organic phase was washed with water, dried and evaporated to dryness under reduced pressure. The 2.3 g of residue were chromatographed over silica gel and eluted with an 8-2 methylene chloride-ethyl acetate mixture to obtain 430 mg of 11β-(4-dimethylaminophenyl)-17α-(prop-1-ynyl)-17β-acetoxy-Δ$^{1,3,5(10)}$-estratriene-3-ol with an Rf=0.58 and 800 mg of 11β-(4-dimethylaminophenyl)-17α-(prop-1-ynyl)-Δ$^{1,3,5(10)}$-estratriene-3,17β-diol with an Rf=.0.36.

The 430 mg of the 17β-acetoxy compound were dissolved in 4 ml of refluxing methylene chloride and the solution was filtered. 4 ml of isopropyl ether were added to the filtrate and the mixture was evaporated to a small volume and iced. The mixture was vacuum filtered and the product was washed with isopropyl ether and dried at 60° C. under reduced pressure to obtain 370 mg of the 17β-acetoxy compound melting at 236° C. and having a specific rotation of $[\alpha]_D^{20} = 194.5° \pm 3°$.

Analysis: C$_{31}$H$_{37}$NO$_3$; Calculated: %C 78.95; %H 7.91; %N 2.97; Found: 78.7; 7.9; 3.0.

880 mg of the 3,17β-diol compound from 2 preparations were dissolved in 12 ml of refluxing methylene chloride and the mixture was filtered. 12 ml of isopropyl ether were added to the filtrate and the mixture was concentrated to a volume of 5 ml. The mixture was iced and vacuum filtered and the product was washed with iced isopropyl ether and dried to obtain 770 mg of the 3,17β-diol compound melting at 246° C. and having a specific rotation of $[\alpha]_D^{20} = -188.5° \pm 2.5°$.

Analysis: C$_{29}$H$_{35}$NO$_2$; Calculated: %C 81.08; %H 8.21; %N 3.26; Found: 81.1; 8.2; 3.1.

EXAMPLE 3

2-(acetyloxy methylene)-11β-(4-dimethylaminophenyl)-17α-(prop-1-ynyl)-Δ$^{4,9}$-estradiene-17β-ol-3-one STEP A: 2-hydroxy methylene-11β-(4-dimethylaminophenyl)-17α-(prop-1-ynyl)-Δ$^{4,9}$-estradiene-17β-ol-3-one 5 g of a 55.5% suspension of sodium hydride in oil were washed three times with 50 ml of diethyl oxide to remove surnagent and then 100 ml of dry benzene and 5 g of 11β-(4-dimethylaminophenyl)-17α-(prop-1-ynyl)-Δ$^{4,9}$-estradiene-17β-ol-3-one were added thereto. 9.4 ml of ethyl formate were added thereto dropwise and the mixture was stirred at room temperature for 20 hours and was then poured into 200 ml of water. The mixture was washed three times with 50 ml of diethyl oxide and the wash liquids were extracted twice with 50 ml of water. The combined aqueous phases were adjusted to a pH of 3.2 by addition of 70 ml of 2N hydrochloric acid and then made basic by addition of 40 ml of aqueous saturated sodium bicarbonate solution. The mixture was extracted once with 100 ml and then three times with 50 ml of diethyloxide. The combined organic phases were washed with 50 ml of aqueous saturated sodium chloride solution, dried and evaporated to dryness under reduced pressure to obtain 5.2 of raw 2-hydroxy methylene-11β-(4-dimethylaminopropyl)-17α-prop-1-ynyl)-Δ$^{4,9}$-estradiene-17β-ol3-one which was used as is for the next step.

STEP B: 2-(acetyloxymethylene)-11β-(4-dimethylaminophenyl)-17α-(prop-1-ynyl)-Δ$^{4,9}$-estradiene-17β-ol-3-one 0.2 ml of pyridine and then 0.16 ml of acetyl chloride were added at 5° C. to a solution of 460 mg of the product of Step A in 20 ml of dry chloroform and the mixture stood in an ice bath for one hour after which 10 ml of aqueous sodium bicarbonate solution were added thereto. The mixture was stirred for 5 minutes and the decanted aqueous phase was washed with water, dried and evaporated to dryness under reduced pressure. The 510 mg of residue was dissolved in 10 ml of methylene chloride and 50 mg of activated carbon were added thereto. The mixture was filtered and the filtrate was evaporated to dryness to obtain 490 mg of product. The latter was empasted with petroleum ether and the product was washed with petroleum ether and then twice with 5 ml of isopropyl ether and dried at 50° C. under reduced pressure to obtain 380 mg of 2-(acetyloxymethylene)-11β-(4-dimethylaminophenyl)-17α-(prop-1-ynyl)-Δ$^{4,9}$-estradiene-17β-ol-3-one with a specific rotation of $[\alpha]_D^{20} = +182° \pm 3°$ (c=1% in chloroform).

Analysis: $C_{32}H_{37}NO_4$; Calculated: %C 76.92; %H 7.46; %N 2.8; Found: 77.0; 7.6; 2.6.

EXAMPLE 4

2-(4-morpholinylmethylene)-11β-(4-dimethylaminophenyl)-17α-(prop-1-ynyl)-Δ$^{4,9}$-estradiene-17β-ol-3-one 0.24 ml of morpholine were added to a solution of 1.065 g of 2-hydroxymethylene-11β-(4-dimethylaminophenyl)-17α-(prop-1-ynyl)-Δ$^{4,9}$-estradiene-17β-ol-3-one in 10 ml of methanol and the mixture was heated to 55° C. for one hour and then evaporated to dryness under reduced pressure at 50° C. The 1.25 g of residue was chromatographed over alumina and eluted with 70-30-1 cyclohexane-acetone-triethylamine mixture to obtain 1.06 g of 2-(4-morpholinylmethylene)-11β-(4-dimethylaminophenyl)-17α-(prop-1-ynyl)-Δ$^{4,9}$-estradiene-17β-ol-3-one with a Rf=0.4, and with specific rotation of $[\alpha]_D^{20} = +263° \pm 4.5°$ (c=0.7% in chloroform).

EXAMPLE 5

2α-methyl-11β-(4-dimethylaminophenyl)-17α-(prop-1-ynyl)-Δ$^{4,9}$-estradiene-17β-ol-3-one and its 2β-isomer A solution of 0.82 ml of cyclohexyl isopropylamine in 5 ml of tetrahydrofuran was slowly introduced at −70° C. under argon to a mixturwe of 3 ml of 1.6M of butyllithium in hexane and 5 ml of tetrahydrofuran and after standing for 10 minutes, a solution of 2.2 g of 11β-(4-dimethylaminophenyl)-17β-(2RS tetrahydropyranyloxy)-17α-(prop-1-ynyl)-Δ$^{4,9}$-estradiene-3-one in 8 ml of anhydrous tetrahydrofuran was added thereto at −70° C. The mixture stood at −70° C. for 10 minutes and then 0.5 ml of methyl iodide were added thereto. The mixture stood at −70° C. for 30 minutes and then was allowed to return to room temperature. One ml of triethylamine was added to the mixture which was diluted with ethyl acetate. The organic phase was washed with water, dried and evaporated to dryness to obtain 2.5 g of product. The latter was dissolved in 25 ml of methanol and 4 ml of 50% hydrochloric acid were added to the mixture which stood at room temperature for two hours and was diluted with water. The mixture was extracted with methylene chloride and the organic phase was washed with water, dried and evaporated under reduced pressure to obtain 2.04 g of a mixture of the two epimers of 2-methyl-11β-(4-dimethylaminophenyl)-17α-(prop-1-ynyl)-Δ$^{4,9}$-estradiene-17β-ol-3-one. The mixture was chromatographed over silica gel and eluted with a 2-3 ether-petroleum ether mixture to obtain 600 mg of the 2β-methyl and 345 mg of the 2α-methyl epimer and about 280 mg of the mixture. 1.1 g of the 2β-methyl isomer were crystallized from a methylene chloride-isopropyl ether to obtain 1.04 g of the 2β-methyl isomer melting at 211° C. 703 mg of 2α-methyl isomer were crystallized froma methylene chloride-isopropyl ether to obtain 614 mg of the product melting at 204° C. Another crystallization of the product gave 560 mg of product melting at 205° C.

Analysis: $C_{30}H_{37}NO_2$; Calculated: %C 81.22; %H, 8.40; %N 3.15; Found: 2α-isomer 81.2; 8.5; 3.2; 2β-isomer 80.8; 8.6; 3.2.

EXAMPLE 6

11β-(3-methoxyphenyl)-17α-(prop-1-ynyl)-Δ$^{5(10)}$-estrene-17β-ol-3-one and 11β-(3-methoxyphenyl)-17α-(E)-(prop-1-enyl)-Δ$^{5(10)}$-estrene-17β-ol-3-one.

STEP A: 3,3-ethylenedioxy-11β-(3-methoxyphenyl)-17α-(prop-1-ynyl)-Δ$^9$-estrene-5α,17β-diol A mixture of 33.8 ml of 0.8M of 3-methoxyphenyl magnesium bromide in tetrahydrofuran and 285 mg of cuprous chloride was stirred under nitrogen at −20° C. for 15 minutes and a solution of 3.3 g of 3,3-ethylenedioxy-5α,10α-epoxy-17α-(prop-1-ynyl)-Δ$^{9(11)}$-estrene-17β-ol in 33 ml of tetrahydrofuran was added over 15 minutes. After a few minutes, 33 ml of tetrahydrofuran were added and the mixture was stirred at −20° C. for one hour and poured into a mixture of 15 g of ammonium chloride in 200 ml of iced water. The mixture was stirred for 30 minutes and was extracted three times with ether. The organic phase was washed with water, dried and evaporated to dryness under reduced pressure to obtain 5.3 g of residue. The latter was chromatographed over silica gel and eluted with 95-1 methylene chloride-acetone mixture containing 1% of triethylamine to obtain 2.7 g of product with an Rf=0.30. 200 mg of product were crystallized from an isopropyl ether-methylene chloride mixture to obtain 165 mg of 3,3-ethylenedioxy-11β-(3-methoxyphenyl)-17α-(prop-1-ynyl)-Δ$^9$-estrene-5α,17β-diol in the form of white crystals melting at 228° C.

Analysis: $C_{30}H_{38}O_5$; Calculated: %C 75.28; %H 8.80; Found: 75.3; 8.1.

STEP B: 11β-(3-methoxyphenyl)-17α-(prop-1ynyl)-Δ$^{4,9}$-estradiene-17β-ol-3-one A mixture iof 2.5 g of the product of Step A, 2.5 g of Redex resin and 125 ml of 95% ethanol was refluxed with stirring for 90 minutes and was cooled and filtered. The filter was rinsed with 95% ethanol and the filtrate was evaporated to dryness under reduced pressure to obtain 2.38 g of residue. The latter was chromatographed over silica gel and eluted with a 3-2 petroleum ether-ethyl acetate mixture. The 1.75 g of amorphous product was crystallized from an ether-cyclo-hexane mixture and was vacuum filtered. The product was rinsed with cyclohexane and dried under reduced pressure to obtain 1.42 of 11β-(3-methoxyphenyl)-17α-(prop-1-ynyl)-Δ$^{4,9}$-estradiene-17β-ol-3-one melting at 164° C.

Analysis: $C_{28}H_{32}O_3$; Calculated: %C 80.73; %H 7.74; Found 80.7; 7.9.

STEP C:

170 mg of cut lithium were added in small portions at −55° C. to a solution of 20 ml of tetrahydrofuran, 5 ml of tert.-butanol, 4.17 g of 11β-(3-methoxyphenyl)-17α-(prop-1-ynyl)-Δ$^{4,9}$-estradiene-17β-ol-3-one and 100 ml of liquid ammonia and after two hours at −55° C., 50 ml of aqueous ammonium chloride solution were slowly added thereto. The temperature was allowed to rise to room temperature and the mixture was extracted with ethyl acetate. The organic phase was washed with aqueous sodium chloride solution, dried and evaporated to dryness to obtain 4.3 g of resin. The latter was chromatographed over silica gel and eluted with a 7-3 cyclohexane-ethyl acetate mixture to obtain 380 mg of 11β-(3-methoxyphenyl)-17α-(E)-(prop-1-enyl)-5,(10)-estrene-17β-ol-3-one with a Rf=0.27 and a specific rotation of $[\alpha]_D^{20} = +10.5° \pm 1°$ (c=1.2% in chloroform) and 2.65 g of 11β-(3-methoxyphenyl)-17α-(prop-1-ynyl)-Δ$^{5(10)}$-estrene-17β-ol-3-one with an Rf=0.25 and a specific rotation of $[\alpha]_D^{20} = -30° \pm 1.5°$ (c=1% in chloroform).

Analysis: 17α(prop-1-enyl) $C_{28}H_{36}O_3$; Calculated: %C 79.96; %H 8.63; Found: 79.8; 8.9.

Analysis: 17α-(prop-1-ynyl) $C_{28}H_{34}O_3$; Calculated: %C 80.34; %H 8.19; Found: 80.4; 8.3.

EXAMPLE 7

11β-(4-dimethylaminophenyl)-17α-(prop-1-ynyl)-isoxazolo[4,5]-Δ$^{4,9}$-estradiene-17β-ol 350 mg of hydroxylamine hydrochloride were added to a solution of 1.2 g of 2-hydroxymethylene-11β-(4-dimethylaminophenyl)-17α-(prop-1-ynyl)-Δ$^{4,9}$-estradiene-17β-ol-3-one in 6 ml of tert.-butanol and the mixture was refluxed for 10 minutes, cooled and diluted with water. The mixture was extracted with methylene chloride and the organic phase was washed, dried and evaporated to dryness under reduced pressure. The 1.23 g of residue was chromatographed over 90 g of silica gel and eluted with a 4-6 petroleum ether-ether mixture to obtain 755 mg of 11β-(4-dimethylaminophenyl)-17α-(prop-1-ynyl)isoxazolo[4,5-b]-Δ$^{4,9}$-estradiene-17β-ol.

EXAMPLE 8

2-cyano-11β-(4-dimethylaminophenyl)-17α-(prop-1-ynyl)-Δ$^{4,9}$-estradiene-17β-ol-3-one Nitrogen was bubbled at room temperature through a solution of 1.2 g of the product of Step A of Example 7 in 10 ml of methanol for 15 minutes and 3 ml of N potassium hydroxide solution were added thereto. The solution stood under nitrogen at room temperature for three hours and was diluted with water. The mixture was extracted with methylene chloride and the organic phase was washed with water, dried and evaporated to dryness under reduced pressure. The 1.19 g of residue was chromatographed over silica gel and eluted with a 7-3 ether-petroleum ether mixture to obtain 685 mg of 2-cyano-11β-(4-dimethylaminophenyl)-17α-(prop-1-ynyl)-Δ$^{4,9}$-estradiene-17β-ol-3-one.

Analysis: $C_{30}H_{34}O_2N_2$; ¼$H_2O$; Calculated: %C 78.48; %H 7.57; %N 6.10; %$H_2O \simeq 1$; Found: 78.2; 7.6; 5.9; ≃0.8.

EXAMPLE 9

2,2-dicyano-11β-(4-dimethylaminophenyl)-17α-(prop-1-ynyl)-Δ$^{4,9}$-estradiene-17β-ol-3-one 4.4 ml of a solution of 1.6M of butyllithium in hexane were added under nitrogen to 10 ml of anhydrous tetrahydrofuran and after cooling the mixture to −70° C., a solution of 1.15 ml of N-cyclohexyl-isopropylamine in 15 ml of anhydrous tetrahydrofuran was added thereto. The solution was cooled to −70° C. and a solution of 1.290 g of 11β-(4-dimethylaminophenyl)-17α-(prop-1-ynyl)-Δ$^{4,9}$-estradiene-17β-ol-3-one in 12 ml of tetrahydrofuran was added thereto to obtain solution A.

Solution A was added dropwise at −60° C. to a solution of 2.55 g of tosyl cyanide in 15 ml of tetrahydrofuran and the mixture stood at −60° C. for 40 minutes and then allowed to rise to room temperature. The mixture was poured into water and was extracted with ethyl acetate. The organic phase was washed, dried and evaporated to dryness under reduced pressure and the 2.85 g of residue were chromatographed over 80 g of silica gel. Elution with a 4-1 benzene-ethyl acetate mixture yielded 1.06 g of product which was crystallized from a methylene chloride-isopropyl ether mixture to obtain 774 mg of 2,2-dicyano-11β-(4-dimethylaminophenyl)-17α-(prop-1-ynyl)-Δ$^{4,9}$-estradiene-17β-ol-3-one melting at 265° C.

Analysis: $C_{31}H_{33}N_3O_2$; Calculated: %C 77.63; %H 6.93; %N 8.76; Found: 77.6; 7.0; 8.7.

EXAMPLE 10

11β-(4-dimethylaminophenyl)-17α-(prop-1-ynyl)-Δ$^{5(10)}$-estrene-17β-ol-3-one 15 ml of anhydrous tetrahydrofuran and 2.5 ml of tert.-butanol were added to liquid ammonia at −60° C. and then 2.15 g of 11β-(4-dimethylaminophenyl)-17α-(prop-1-ynyl)-Δ$^{4,9}$-estradiene-17β-ol-3-one were added thereto. 80 mg of lithium were added to the solution in 6 fractions over 30 minutes and after another 30 minutes at −60° C., the mixture was placed in an ice bath. 40 ml of an aqueous slution of 100 g/l of ammonium chloride were slowly added to the mixture which was stirred at room temperature for 30 minutes. The mixture was extracted with ethyl acetate and the organic phase was washed with aqueous ammonium chloride solution, dried and evaporated to dryness. The 2.3 g of residue was chromatographed over 90 g of silica gel and eluted with a 4-1 benzene-ethyl acetate mixture to obtain 1.67 g of 11β-(4-dimethylaminophenyl)-17α-(prop-1-ynyl)-Δ$^{5(10)}$-estrene-17β-ol-3-one. An analytical sample which was obtained by chromatography over silica gel and elution with a 2-1 ether-heptane mixture had a specific rotation $[\alpha]_D^{20} = -68.5° \pm 2.0$ (c=1% in chloroform).

Analysis: $C_{29}H_{37}NO_2$; Calculated: %C 80.7; %H 8.64; %N 3.25, Found: 80.6; 8.90; 3.05.

EXAMPLE 11

3-methoxy-11β-(4-dimethylaminophenyl)-17α-(prop-1-ynyl)-Δ$^{1,3,5(10)}$-estratriene-17β-ol 0.06 ml of methyl sulfate were added all at once to a solution of 215 mg of 11β-(4-dimethylaminophenyl)-17α-(prop-1-ynyl)-Δ$^{1,3,5(10)}$-estratriene-3,17β-diol, 6 ml of 0.1N sodium hydroxide solution and 6 ml of acetone cooled in an ice bath and the mixture was removed from the ice bath, stirred for 2½ hours and then was diluted with 30 ml of ethyl acetate. The decanted organic phase was washed with aqueous sodium chloride solution, dried and evaporated to dryness under reduced pressure. The 155 mg of residue were chromatographed over silica gel and eluted with a 3-2 petroleum ether-etyl acetate mixtutre after dissolution in methylene chloride to obtain 120 mg of 3-methoxy-11β-(4-dimethylaminophenyl)-17α-(prop-1-ynyl)-Δ$^{1,3,5(10)}$-estratriene-17β-ol with an Rf=0.4.

EXAMPLE 12

3-methoxy-11β-(4-dimethylaminophenyl)-17α-(prop-1ynyl)-17β-acetoxy-Δ$^{1,3,5(10)}$-estratriene 0.08 ml of methyl sulfate were added with stirring under nitrogen to a mixture of 330 mg of 11β-(4-dimethylaminophenyl)-17α-(prop-1-ynyl)-17β-acetoxy-Δ$^{1,3,5(10)}$-estratriene-3-ol, 1.65 ml of acetone, 0.33 ml of water and 0.42 ml of 2N sodium hydroxide solution and the mixture was stirred for one hour and was diluted with water. The mixture was extracted with ethyl acetate and the organic phase was dried and evaporated to dryness under reduced pressure. The residue was chromatographed over silica gel and eluted with a 4-1 cyclohexane-ethyl acetate mixture to obtain 220 mg of 3-methoxy-11β-(4-dimethylaminophenyl)-17α-(prop-1-ynyl)-17β-acetoxy-Δ$^{1,3,5(10)}$-estratriene.

EXAMPLE 13

11β-[4-(2-dimethylaminoethoxy)-phenyl]-Δ$^{1,3,5(10)}$-estratriene-3,17β-diol

STEP A: 3,3-ethylenedioxy-11β-[4-(2-dimethylaminoethoxy)-phenyl]-Δ$^9$-estrene-5α-ol-17-one A solution of 97.4 g of 4-bromo-4-(2-dimethylaminoethoxy)-benzene in 480 ml of tetrahydrofuran was added at about 35° C. over 75 minutes to a mixture of 11.5 g of magnesium turnings and 20 ml of tetrahydrofuran and the mixture was stirred for one hour and 380 ml of the solution were poured into a suspension of 23.5 g of a complex of CuBr.(CH$_3$)$_2$S and 235 ml of tetrahydrofuran. After stirring for 15 minutes at room temperature, a solution of 30 g of 3,3-ethylenedioxy-5α,10α-epoxy-Δ$^{9(11)}$-estrene-17-one [described in EPC application No. 57,115] in 150 ml of tetrahydrofuran was added to the mixture over 20 minutes and the mixture was stirred at room temperature for 16 hours and was poured into 3 liters of aqueous saturated ammonium chloride solution. The mixture was extracted with ether and the organic phase was washed with aqueous saturated ammonium chloride solution, then with aqueous saturated sodium chloride solution, dried and evaporated to dryness under reduced pressure. The 66.7 g of residue were chromatographed over silica gel and eluted with a 9-1 chloroform-methanol mixture containing 1% of triethylamine and then over alumina and eluted with an 8-2 benzene-ethyl acetate mixture to obtain 30.65 g of 3,3-ethylenedioxy-11β-[4-(2-dimethylaminoethoxy)-phenyl]-Δ$^9$-estrene-5α-ol-17-one.

STEP B: 11β-[4-(2-dimethylaminoethoxy)-phenyl]-Δ$^{4,9}$-estradiene-3,17-dione

A mixture of 5 g of the product of Step A, 100 ml of methanol and 15 ml of 2N hydrochloric acid was stirred at room temperature for 3 hours and was then poured into 400 ml of ether. The mixture was made alkaline by the addition of 100 ml of 0.5M sodium bicarbonate solution and was stirred for 15 minutes. The decanted aqueous phase was extracted with ether and the organic phase was washed with aqueous saturated sodium chloride solution, dried and evaporated to dryness under reduced pressure. The 3.90 g of product were empasted with a minimum of isopropyl ether 3 times to obtain 3.10 g of 11β-[4-(2-dimethylaminoethoxy)-phenyl]-Δ$^{4,9}$-estradiene-3,17-dione melting at 206° C.

STEP C: 11β-[4-(2-dimethylaminoethoxy)-phenyl]-Δ$^{1,3,5(10)}$-estratriene-3-ol-17-one A mixture of 4 g of acetic anhydride and 2 ml of acetyl bromide was added at 0° to 5° C. to a solution of 4 g of the product of Step B in 40 ml of methylene chloride and the mixture was allowed to rise to room temperature and was then stirred for 2 hours. The mixture was poured into 200 ml of aqueous saturated sodium bicarbonate solution and was stirred for 15 minutes. The mixture was extracted with methylene chloride and the organic phase was washed with water, dried and evaporated to dryness under reduced pressure. The 4.33 g of residue were dissolved in 40 ml of methanol and after the addition of 4 ml of sodium hydroxide, the mixture was stirred for 90 minutes at room temperature and was poured into 200 ml of water. The mixture was adjusted to a pH of ≃2 by addition of 30 ml of 2N hydrochloric acid and was then adjusted to a pH of ≃9 by addition of 5 ml of ammonium hydroxide. The mixture was extracted with methylene chloride and the organic phase was washed with water, dried and evaporated to dryness under reduced pressure. The residue was chromatographed over silica gel and was eluted with a 9-1 methylene chloride-methanol mixture to obtain 2.6 g of 11β-[4-(2-dimethylaminoethoxy)-phenyl]-Δ$^{1,3,5(10)}$-estratriene-3-ol-17-one.

STEP D: 11β-[4-(2-dimethylaminoethoxy)-phenyl]-Δ$^{1,3,5(10)}$-estratriene-3,17β-diol 545 mg of sodium borohydride were added in small fractions to a mixture of 2.1 g of the product of Step C and 21 ml of methanol and the mixture was stirred at room temperature for one hour and was poured into 210 ml of a mixture of ice and water. The mixture was extracted with methylene chloride and the organic phase was washed with aqueous saturated sodium chloride solution, dried and evaporated to dryness under reduced pressure. The residue was chromatographed over silica gel and eluted with an 8-2 acetone-methanol mixture to obtain 1.37 g of product which was crystallized from a methylene chloride-isopropyl ether to obtain 1.27 g of 11β-[4-(2-dimethylaminoethoxy)-phenyl]-Δ$^{1,3,5(10)}$-estratriene-3,17-diol melting at 130° C. and having a specific rotation of $[\alpha]_D^{20} = -46.5° \pm 1.5°$ (c=0.8% in chloroform).

EXAMPLE 14

11β-[4-2-dimethylaminoethoxy)-phenyl]-Δ$^{1,3,5(10)}$-estratriene-17β-ol

STEP A: A AND B isomers of 11β-[4-(2-dimethylaminoethoxy)-phenyl]-Δ$^{4,9}$-estradiene-3,17β-diol 1.74 g of sodium borohydride were added in small fractions over 20 minutes to a solution of 5 g of 11β-[4-(2-dimethylaminoethoxy)-phenyl]-Δ[4,9]-estradiene-3,17-dione in 100 ml of methanol and the mixture was stirred at room temperature for one hour and was poured into 750 ml of ice and water. The mixture was stirred for 30 minutes and was vacuum filtered. The product was washed until the wash water was neutral and dried to obtain 4.6 g of A and B isomers of 11β-[4-(2-dimethylaminoethoxy)-phenyl]-Δ[4,9]-estradiene-3,17β-diol melting at 110° C.

STEP B: 11β-[4-(2-dimethylaminoethoxy)-phenyl]-Δ[1,3,5(10)]-estratriene-17β-ol

A mixture of 1 g of the product of Step A, 20 ml of tetrahydrofuran and 1 ml of 6N hydrochloride acid was stirred at room temperature for 3 hours and was poured into 200 ml of aqueous saturated sodium bicarbonate solution. The mixture was extracted with ethyl acetate and the organic phase was washed with aqueous saturated sodium chloride solution, dried and evaporated to dryness under reduced pressure. The residue was chromatographed over silica gel and eluted with an 8-2 petroleum ether-acetone mixture to obtain 325 mg of product which was dissolved in a 1-1 methylene chloride-isopropyl ether mixture. The solution was slowly concentrated to half its volume to obtain 300.5 mg of 11β-[4-(2-dimethylaminoethoxy)-phenyl]-Δ[1,3,5(10)]-estratriene-17β-ol melting at 155° C. and having a specific rotation of $[\alpha]_D^{20} = -38.5° \pm 2°$ (c=0.8% in chloroform).

EXAMPLE 15

3-(2-dimethylamino-ethoxy)-11β-phenyl-Δ[1,3,5(10)]-estratriene-17β-ol

STEP A: 3,3-ethylenedioxy-11β-phenyl-Δ[9]-estrene-5αol-17-one 80 g of bromobenzene were added over 70 minutes to a refluxing mixture of 13 g of magnesium turnings and 30 ml of tetrahydrofuran and the mixture was allowed to return to 20° C. with stirring. The mixture was cooled to −25° C. to obtain 330 ml of a solution of 0.85M of phenyl magnesium bromide. 4.165 g of cuprous chloride were added thereto all at once and the mixture was stirred at −25° C. for 10 minutes after which a solution of 11.5 g of 3,3-ethylenedioxy-5α,10α-epoxy-Δ[9(11)]-estrene-17-one in 60 ml of tetrahydrofuran was added dropwise at −25° C. over 20 minutes. The mixture was held at −25° C. for two hours and was then poured into a mixture of 600 ml of ice and 45 g of ammonium chloride. The mixture was stirred for 30 minutes and was extracted with ether. The organic phase was washed with water, dried and evaporated to dryness under reduced pressure. The residue was chromatographed over silica gel and eluted with a 6-4 benzene-ethyl acetate mixture contain 1% of triethylamine to obtain 7.86 g of 3,3-ethylenedioxy-11β-phenyl-Δ[9]-estrene-5α-ol-17-one melting at 173° C. and having a specific rotation of $[\alpha]_D^{20} = +54.5° \pm 1.5°$ (c=1% in chloroform.

STEP B: 11β-phenyl-Δ[4,9]-estradiene-3,17-dione

A mixture of 7.4 g of the product of Step A in 225 ml of 95% ethanol was heated to 40° C. and 7.4 g of redex CF resin were added thereto all at once. The mixture was refluxed with stirring under an inert gas for one hour and was filtered. The product was empasted four times with 20 ml of 95% ethanol and the filtrate was evaporated to dryness under reduced pressure. The 6.5 g of resin were chromatographed over silica gel and eluted with a 9-1 chloroform-ethyl acetate mixture. The 486 mg of product were dissolved at reflux in a mixture of 12.5 ml of isopropyl ether and 3 ml of methylene chloride and the mixture was filtered hot. The filtrate was concentrated to a small volume and crystallization was refluxed was effected. The mixture was vacuum filtered and the product was washed with isopropyl ether to obtain 369.4 mg of 11β-phenyl-Δ[4,9]-estradiene-3,17-one melting at a 197° C. and having a specific rotation of $[\alpha]_D^{20} = +223° \pm 3°$ (c=0.5% in chloroform).

STEP C: 11β-phenyl-Δ[1,3,5(10)]-estratriene-3-ol-17-one

A mixture of 3.75 ml of acetic anhydride and 1.9 ml of acetyl bromide was added dropwise with stirring at 0° C. to a solution of 3.76 g of the product of Step B in 26.3 ml of methylene chloride and the mixture was stirred at room temperature for 75 minutes and was added dropwise with stirring to 90 ml of aqueous saturated sodium bicarbonate solution. After stirring for 15 minutes, the mixture was extracted with methylene chloride and the organic phase was washed with water, dried and evaporated to dryness under reduced pressure. The residue was added to 26.3 ml of methanol and then 18.8 ml of sodium hydroxide solution were added thereto. The mixture was stirred for 16 hours and was acidified to a pH of about 1 at approximately 20° C. by addition of 40 ml of sulfuric acid diluted to one-fifth. The mixture was stirred for 20 minutes and was then vacuum filtered. The product was empasted four times with 25 ml of water to obtain 4.030 g of product which was crystallized from methylene chloride to obtain 3.01 g of 11β-phenyl-Δ[1,3,5(10)]-estratriene-3-ol-17-one melting at 290° C. and having a specific rotation of $[\alpha]_D^{20} = -9° \pm 2°$ (c=0.5% in chloroform).

STEP D: 11β-phenyl-Δ[1,3,5(10)]-estratriene-3,17β-diol 144 mg of sodium borohydride were added over 10 minutes under an inert atmosphere with stirring to a mixture of 1 g of the product of Step C in 10 ml of methanol at 50° C. and after stirring at 50° C. for one hour, the mixture was cooled to 20° C. The pH was adjusted to 5 by dropwise addition of 0.4 ml of acetic acid and the mixture was stirred for 10 minutes and poured into 30 ml of ice and water. The mixture was stirred for 30 minutes and was vaccuum filtered. The product was empasted with water and dried to obtain 896 mg of 11β-phenyl-Δ[1,3,5(10)]-estratriene-3,17β-diol melting at 228° C. and having a specific rotation of $[\alpha]_D^{20} = -34° \pm 2°$ (c=0.5% in chloroform).

STEP E: 3-(2-dimethylaminoethoxy)-11β-phenyl-Δ[1,3,5(10)]-estratriene-17β-ol 3.5 ml of an 95% ethanolic solution of N sodium hydroxide were added all at once to a mixture of 1.220 g of the product of Step D and 12.2 ml of 95% ethanol and the mixture was heated to 60° C. after which a solution of the amine prepared from 555 mg of dimethylamino-2-chlorethane hydrochloride in 1.7 ml of 95% ethanol was added all at once. The mixture was neutralized by the addition of freshly prepared 3.85 ml of N sodium hydroxide in 95% ethanol and the mixture was refluxed with stirring under an inert atmosphere for 90 minutes and was cooled to 20° C. and filtered. The product was empasted with 10 ml of 95% ethanol and the filtrate was evaporated to dryness. The residue and 20 ml of methylene chloride and 20 ml of water was stirred for 10 minutes and the decanted aqueous phase was extracted with methylene chloride. The organic phase was washed with water, dried and evaporated to dryness under reduced pressure. The 1.261 g of residue was chromatographed over silica gel and eluted with a 6-4 chloroformmethanol mixture to obtain 939 mg of 3-(2-dimethylaminoethoxy)-11β-phenyl-$\Delta^{1,3,5(10)}$-estratriene-17β-ol with a specific rotation of $[\alpha]_D^{20} = -32° \pm 2°$ (c=0.7% in chloroform).

EXAMPLE 16

Tablets were prepared containing 50 mg of the product of Example 5 and sufficient excipient of talc, starch and magnesium stearate for a final weight of 120 mg.

PHARMACOLOGICAL STUDY

I. Activity of products on hormonal receptors

A. Mineralcorticoidal receptor of kidneys of the rat

Male Sprague-Dawley EOPS rats weighing 140 to 160 g surrenalectomized 4 to 8 days previously were killed and their kidneys were perfused in situ with 50 ml of a buffer (10 mM of Tris 0.25M of Saccharose and sufficient hydrochloric acid for a pH of 7.4). The kidneys were then removed, decapsulated and homogenized at 0° C. with a polytetrafluoroethylene-glass Potter (1 g of tissue per 3 ml of buffer). The homogenate was centrifuged for 10 minutes at 800 g at 0° C.

After elimination of the fixation of tritiated aldosterone with glucocorticoid receptor, 21-methyl-$\Delta^{1,4,6}$-pregnatriene-20-yne-11β,17β-diol-3-one fixed only with the glucocorticoid receptor was added to the supernatant at a final concentration of $10^{-6}$M. The supernatant was ultracentrifuged at 105,000 g for 60 minutes and 0° C. and aliquoits of the resulting surnageant were incubated at 0° C. with a constant concentration (T) of tritiated aldosterone in the presence of increasing concentrations of (0–2500×$10^{-9}$M) of cold aldosterone or the cold test product. After a time (t) of incubation, the concentration of tied tritiated aldosterone (B) was measured by the technique of adsorption on carbon dextran.

B. Androgen receptor of prostate of rats

Male Sprague-Dawley EOPS rats weighing of 160 to 200 g were castrated and 24 hours later, the animals were killed. The prostates were removed, weighed and homogenized at 0° C. with a polytetrafluoroethylene-glass Potter with a buffered TS solution (Tris, 10 mM, 0.25M Saccharose, HCl-pH of 7.4) using 1 g of tissue per 5 ml of TS. The homogenate was then ultracentrifuged at 105,000 g after 60 minutes at 0° C. and aliquoits of the resulting supernatant were incubated at 0° C. for 2 hours with a constant concentration (T) of product P or 17-methyl-$4,9,11$-estratriene-17-ol-3-one in the presence of increasing concentration (0– 1,000×$10^{-9}$M) of either cold P, cold testosterone or the test compound. The concentration of tied tritiated (B) was measured for each incubate by the technique of adsorption on carbon-dextran.

C. Progestogen receptor of the uterus of rabbits

Immature rabbits weighing about 1 kg received a cutaneous application of 25 μg of estradiol and the animals were killed 5 days later. The uterus was removed, weighed and homogenized at 0° C. with a polytetrafluoroethylene-glass Potter in a buffered TS solution [Tris 10. mM, 0.25M of saccharose, HCl-pH of 7.4] with 1 g of tissue per 50 ml of TS. The homogenate was ultracentrifuged at 105,000 g for 90 minutes at 0° C. and aliquoits of the resulting supernatant were incubated at 0° C. for a time (t) with a constant concentration (T) of tritiated product R or 17,21-dimethyl-19-nor-$\Delta^{4,9}$-pregnadiene-3,20-dione in the presence of increasing concentrations (0 to 2500×$10^{-9}$M) of either cold R, cold progesterone or cold test compound. The concentration of tied tritiated R (B) was then measured for each incubate by the technique of adsorption on carbon-dextran.

D. Gluocorticoid receptor of thymus of rats

Male Sprague-Dawley EOPS rats weighing 160 to 200 g were surrenalectomized and the animals were killed 4 to 8 days later. The thymus were removed and homogenized at 0° C. in a buffered TS solution of 10 mM, Tris, 0.25M of Saccharose, 2 mM of dithiothreitol, HCl for a pH of 7.4 using a polytetrafluoroethylene-glass Potter at a rate of 1 g of tissue per 10 ml of TS. The homogenate was ultracentrifuged at 105,000 g for 90 minutes at 0° C. and aliquoits of the resulting surnageant were incubated at 0° C. for a time (t) with a constant concentration (T) of tritiated dexamethasone in the presence of an increasing concentration (0 to 2500×$10^{-9}$M) of either cold dexamethasone or cold test product. The concentration of tied tritiated dexamethasone (B) was measured for each incubate by the adsorption on carbon-dextran technique.

E. Estrogen receptor of uterus of mice

Immature female mice 18 to 21 days old were killed and the uterus were removed and homogenized at 0° C. with a polytetrafluoroethylene-glass Potter in a buffered TS solution consisting of 10 mM Tris, 0125M Saccharose, HCl for a pH of 7.4 at a rate of 1 g of tissue per 25 ml of TS. The homogenate was then ultracentrifuged at 105,000 g for 90 minutes at 0° C. and aliquoits of the resulting tritiated were incubated at 0° C. for a time (t) with a constant concentration (T) of tritiated estradiol in the presence of increasing concentrations (0 to 1000×$10^{-9}$M) of either cold estradiol or cold test compound. The concentration of tied tritiated estradiol (B) was measured for each incubate by the technique of adsorption on carbon-dextran.

The calculation of the relative affinity of concentration (ARL) was identical for all of the above receptor tests. One traced the following two curves: the percentage of tied tritiated hormone B/T as a function of the logarithm of the cold hormone concentration and B/T as a function of the logarithm of the concentration of the cold test product. One determined the line of the equation.

$$I_{50} = \frac{\frac{B}{T} \text{max.} + \frac{B}{T} \text{min.}}{2}$$

B/T max. is the percentage of tied tritiated hormone for an incubation of the hormone at concentration T B/T min. is the percentage of tied tritiated hormone for an incubation of the tritiated hormone at a concentration (T) in the presence of a large excess of cold hormone (2500×$10^{-9}$M).

The intersection of the $I_{50}$ line and the curves permits one to determine the concentrations of the cold hormone of the reference (CH) and the cold test compound (CX) which inhibit by 50% the tieing of tritiated hormone with the receptor. The relative affinity of tieing (ARL) of the test product was determined by the equation:

$$ARL = 100 \times \frac{CH}{CX}$$

The results are reported in the following Table.

| Product of Example | Time of incubation at 0° C. | | | | | | | | | |
|---|---|---|---|---|---|---|---|---|---|---|
| | Mineralo corticoid | | Androgen | | Pro-gestogen | | Gluco-corticoid | | Estrogen | |
| | 1 H | 24 H | ½ H | 24 H | 2 H | 24 H | 4 H | 24 H | 2 H | 5 H (25° C.) |
| 1 | <0,1 | <0,1 | — | — | 4 | 4 | 97 | 38 | <0,1 | <0,1 |
| 2 (17 OH) | 0,2 | <0,1 | * | * | 39 | 130 | 153 | 222 | 5 | <0,1 |
| 2 (17 OAc) | <0,1 | <0,1 | <0,1 | <0,1 | 5 | 52 | 58 | 100 | <0,1 | 0,3 |
| 5 (2α) | <0,1 | <0,1 | 0,5 | 0,4 | 40 | 39 | 214 | 255 | <0,1 | <0,1 |
| 5 (2β) | <0,1 | <0,1 | 0,7 | 0,5 | 44 | 44 | 224 | 299 | <0,1 | <0,1 |
| 9 | <0,1 | <0,1 | <0,1 | <0,1 | <0,1 | <0,1 | 14 | 7 | <0,1 | <0,1 |
| 10 | 1,5 | <0,1 | — | — | 27 | 62 | 83 | 115 | <0,1 | <0,1 |
| 13 | — | — | 5 | 6 | — | — | 3,9 | — | 78 | 239 |
| 14 | — | — | 10,6 | 0,5 | — | — | 0,4 | — | 4,1 | 1,4 |
| 15 | — | — | 1,3 | 0,2 | — | — | 2 | — | 0,1 | 0,1 |

*The product presented an affinity for the receptor.

CONCLUSION

The tested compounds and especially those of Examples 2 and 5 present a very remarkable affinity for glucocorticoid and progestogen receptors as well as a slightly moderate affinity for androgen receptors. These results lead to the conclusion that the products present an agonist or antagonistic activity to glucocorticoids, progestogens and androgens. Moreover, the products of Examples 13 and 14 present an agonist or antagonistic activity to estrogens.

II Antiglucocorticoidal Activity

The test used was that of Dausse et al [Molecular Pharmacology, Vol. 13 (1977), p. 948–955] entitled "The relationship between glucocorticoid structure and effects upon thymocytes" for mice thymocytes. The thymocytes of surrenalectomized rats were incubated at 37° C. for 3 hours in a nutritive medium containing $5 \times 10^{-8}M$ of dexamethasone in the presence or absence of the test compound at different concentrations. Tritiated uridine was added and incubation was continued for one hour. The incubates were cooled and treated with a 5% trifluoroacetic acid solution and the mixture was filtered with Whatman GF/A paper. The filter was washed 3 times with a 5% trifluoroacetic acid solution and retained radioactivity on the filter was determined. Glucocorticoids and especially dexamethasone provoked a lessening of incorporation of tritiated uridine and the tested compounds, especially those of Examples 1,2,5 and 10 opposed this effect as can be seen from the following Table.

| Product of Example | $5 \times 10^{-8}$ of Dexamethasone + test product in concentration of | % inhibition of effect of Dexamethasone |
|---|---|---|
| 1 | $10^{-8}M$ | 8 |
| | $10^{-7}M$ | 18 |
| | $10^{-6}M$ | * |
| 2 (17 OH) | $10^{-8}M$ | 41 |
| | $10^{-7}M$ | 91 |
| | $10^{-6}M$ | * |
| 2 (17 OAc) | $10^{-8}M$ | 24 |
| | $10^{-7}M$ | 76 |
| | $10^{-6}M$ | * |
| 3 | $10^{-8}M$ | 0 |
| | $10^{-7}M$ | 0 |
| | $10^{-6}M$ | 60 |
| 4 | $10^{-8}M$ | 0 |
| | $10^{-7}M$ | 0 |
| | $10^{-6}M$ | 51 |
| 5 (2α) | $10^{-8}M$ | 19 |
| | $10^{-7}M$ | 57 |
| | $10^{-6}M$ | 100 |
| 5 (2β) | $10^{-8}M$ | 10 |

-continued

| Product of Example | $5 \times 10^{-8}$ of Dexamethasone + test product in concentration of | % inhibition of effect of Dexamethasone |
|---|---|---|
| | $10^{-7}M$ | 57 |
| | $10^{-6}M$ | * |
| 7 | $10^{-8}M$ | 0 |
| | $10^{-7}M$ | 27 |
| | $10^{-6}M$ | * |
| 9 | $10^{-8}M$ | 3 |
| | $10^{-7}M$ | 1 |
| | $10^{-6}M$ | 2 |
| 10 | $10^{-8}M$ | 0 |
| | $10^{-7}M$ | 23 |
| | $10^{-6}M$ | * |
| 6 | $10^{-8}M$ | 0 |
| | $10^{-7}M$ | 0 |
| | $10^{-6}M$ | 68 |
| 6 (17α propenyle) | $10^{-8}M$ | 0 |
| | $10^{-7}M$ | 0 |
| | $10^{-6}M$ | 56 |

*A dose of $10^{-6}M$ inhibited the effect of dexamethasone totally

CONCLUSION

The products of the invention used alone do not provoke any effect of the glucocorticoid type at doses provoking an ant agonist effect and the tested products present a very remarkable antiglucocorticoid activity and are devoid of any glucocorticoid activity.

Various modifications of the products and methods of the invention may be made without departing from the spirit or scope thereof and it is to be understood that the invention is intended to be limited only as defined in the appended claims.

What we claim is:

1. A compound selected from the group consisting of 19-nor-steroids of the formula

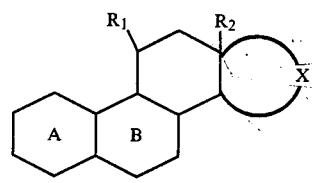

wherein $R_1$ is an organic group of 1 to 18 carbon atoms optionally containing at least one atom selected from the group consisting of oxygen, sulfur, nitrogen, phosphorus and silicon with the atom immediately adjacent the 11-carbon atom being carbon, $R_2$ is a hydrocarbon of 1 to 8 carbon atoms, X is the remainder of a pentagonal or hexagonal ring optionally substituted and optionally containing one unsaturated bond, the A and B rings are selected from the group consisting of (a) (b)
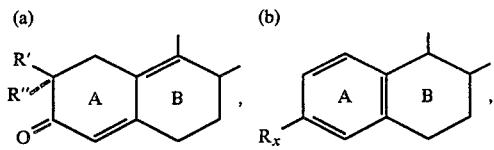

(c) (d)
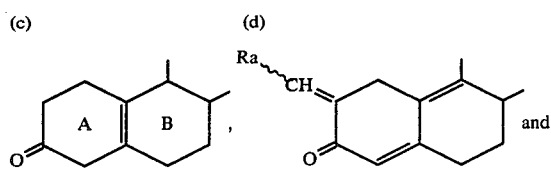
and (e)
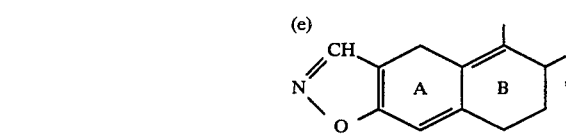

R' and R" are individually selected from the group consisting of hydrogen, —CN and alkyl of 1 to 4 carbon atoms with at least one being other than hydrogen, $R_x$ is selected from the group consisting of hydrogen and $OR_e$, $R_e$ is selected from the group consisting of hydrogen, optionally substituted alkyl of 1 to 6 carbon atoms and acyl, $R_a$ may be in the E or Z positions as indicated by the wavy line and is selected from the group consisting of

and acyloxy $R_a'$ and $R_a''$ are alkyl of 1 to 4 carbon atoms or taken together with the nitrogen atom form a heterocycle of 5 to 6 chain members optionally containing another heteroatom with the proviso that when A and B are

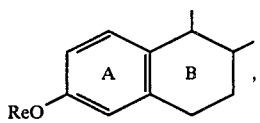

$R_1$ contains at least one nitrogen, phosphorus or silicium atom and when A and B are

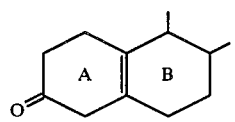

$R_1$ is not a linear akyl and their non-toxic, pharmaceutically acceptable acid addition salts.

2. A compound of claim 1 wherein X is

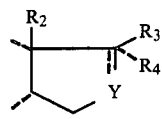

wherein $R_2$ has the definition of claim 1, the dotted line in the 16,17-position indicates an optional double bond, Y is

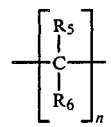

n is 1 or 2, $R_5$ is selected from the group consisting of hydrogen, alkyl of 1 to 8 carbon atoms, alkenyl and alkynyl of 2 to 8 carbon atoms, aryl of 6 to 14 carbon atoms and aralkyl of 7 to 15 carbon atoms, $R_6$ is selected from the group consisting of hydrogen, —OH, alkyl of 1 to 8 carbon atoms, alkenyl and alkynyl of 2 to 8 carbon atoms, aryl of 6 to 14 carbon atoms and aralkyl of 7 to 15 carbon atoms and $R_3$ and $R_4$ are individually selected from the group consisting of hydrogen, —OH, —OAlK$_4$,

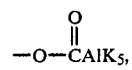

alkenyl and alkynyl of 2 to 8 carbon atoms,

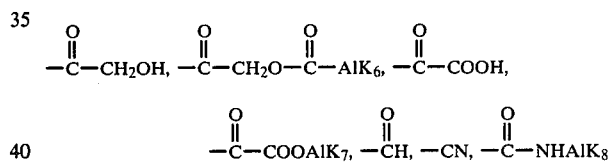

or $R_3$ and $R_4$ together with the carbon atoms are

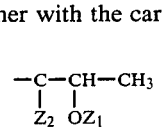

or

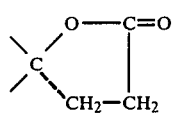

AlK$_4$, AlK$_6$ and AlK$_8$ are selected from the group consisting of alkyl of 1 to 8 carbon atoms and aralkyl of 7 to 15 carbon atoms, AlK$_6$ are selected from the group consisting of alkyl of 1 to 8 carbon atoms, optionally substituted and aralkyl of 7 to 15 carbon atoms, AlK$_7$ and Z$_2$ are alkyl of 1 to 8 carbon atoms and Z$_1$ is selected from the group consisting of hydrogen, alkyl of 1 to 8 carbon atoms and acyl of 1 to 8 carbon atoms.

3. A compound of claim 2 wherein the D ring does not contain unsaturation, n is 1 and $R_5$ and $R_6$ is hydrogen.

4. A compound of claim 1 or 2 wherein $R_3$ is —OH or

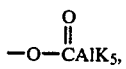

Alk$_5$ is alkyl of 1 to 8 carbon atoms or aralkyl of 7 to 15 carbon atoms and R$_4$ is alkenyl or alkynyl of 2 to 4 carbon atoms.

5. A compound of claim 1 or 2 wherein R$_1$ is aryl or aralkyl carrying an amino of the formula

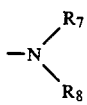

wherein R$_7$ and R$_8$ are alkyl of 1 to 8 carbon atoms or primary, secondary or tertiary alkyl of 1 to 8 carbon atoms containing at least one heteroatom of the group consisting of —O—, —S— or —N— with at least one being nitrogen or substituted with a heterocycle containing at least one nitrogen atom.

6. A compound of claim 1 or 2 wherein R$_1$ is selected from the group consisting of 2-pyridyl, 3-pyridyl and 4-pyridyl,

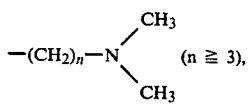

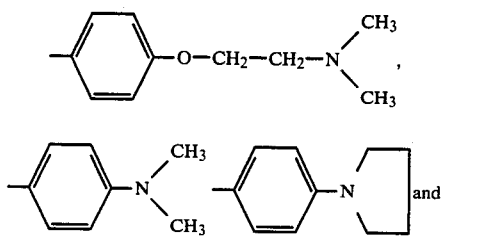

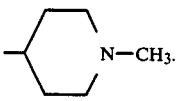

7. A compound of claim 1 or 2 wherein R$_1$ is selected from the group consisting of thienyl, furyl, cycloalkyl of 3 to 6 carbon atoms and phenyl optionally substituted with at least one member of the group consisting of —OH, halogen, —CF$_3$, alkyl and alkoxy of 1 to 8 carbon atoms and alkylthio of 1 to 8 carbon atoms optionally oxidixed to sulfoxide or sulfone and A and B rings are not

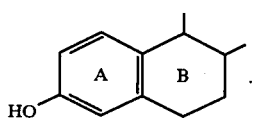

8. A compound of claim 1 or 2 wherein R$_1$ is phenyl substituted with a member of the group consisting of chlorine, fluorine, methylthio, methylsulfonyl, methoxy, —OH and allyloxy.

9. A compound of claim 1 or 2 wherein the A and B rings are

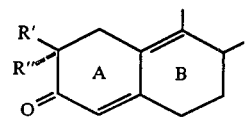

wherein R' and R" are both methyl or both —CN or one is hydrogen and the other is methyl or —CN.

10. A compound of claim 1 or 2 wherein A and B rings are

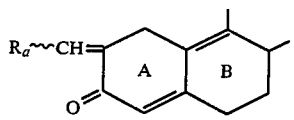

wherein R$_a$ is morpholino or acetoxy.

11. A compound of claim 1 selected from the group consisting of 2,2-dimethyl-11β-(4-dimethylaminophenyl)-17α-(prop-1-ynyl)-Δ$^{4,9}$-estradiene-17β-ol-3-one, 2,2-dicyano-11β-(4-dimethylaminophenyl)-17α-(prop-1-ynyl)-Δ$^{4,9}$-estradiene-17β-ol-3-one, 2,α-methyl-11β-(4-dimethylaminophenyl)-17α-(prop-1-ynyl)-Δ$^{4,9}$-estradiene-17β-ol-3-one, 2β-methyl-11β-(4-dimethylaminophenyl)-Δ$^{4,9}$-estradiene-17β-ol-3-one, 2-cyano-11β-(4-dimethylaminophenyl)-17α-(prop-1-ynyl)-Δ$^{4,9}$-estradiene-17β-ol-3-one and their non-toxic, pharmaceutically acceptable acid addition salts.

12. A compound of claim 1 selected from the group consisting of 11β-(4-dimethylaminophenyl)-17α-(prop-1-ynyl)-Δ$^{1,3,5(10)}$-estratriene-3-; 17β-diol, 11β-(4-dimethylaminophenyl)-17β-acetoxy-17α-(prop-1-ynyl)-Δ$^{1,3,5(10)}$-estratriene-3-ol, 3-methoxy-11β-(4-dimethylaminophenyl)-17α-(prop-1-ynyl)-Δ$^{1,3,5(10)}$-estratriene-17β-ol, 3-methoxy-11β-(4-dimethylaminophenyl)-17β-acetoxy-17α-(prop-1-ynyl)-Δ$^{1,3,5(10)}$-estratriene and their non-toxic, pharmaceutically acceptable acid addition salts.

13. A compound of claim 1 selected from the group consisting of 11β-(3-methoxyphenyl)-17α-(prop-1-ynyl)-Δ$^{5(10)}$-estrene-17β-ol-3-one, E isomer of 11β-(3-methoxyphenyl)-17α-(prop-1-enyl)-Δ$^{5(10)}$-estrene-17β-ol-3-one, 11β-(4-dimethylaminophenyl)-17α-(prop-1-ynyl)-Δ$^{5(10)}$-estrene-17β-ol-3-one and their non-toxic, pharmaceutically acceptable acid addition salts.

14. A compound of claim 1 selected from the group consisting of 2-(acetyloxymethylene)-11β-(4-dimethylaminophenyl)-17α-(prop-1-ynyl)-Δ$^{4,9}$-estradiene-17β-ol-3-one, 2-(4-morpholinomethylene)-11β-(4-dimethylaminophenyl)-17α-(prop-1-ynyl)-Δ$^{4,9}$-estradiene-17β-ol-3-one and their non-toxic, pharmaceutically acceptable acid addition salts.

15. A compound of claim 1 selected from the group consisting of 11β-(4-dimethylaminophenyl)-17α-(prop-1-ynyl)-isoxazolo[4,5-b]-Δ$^{4,9}$-estradiene-17β-ol and its non-toxic, pharmaceutically acceptable acid addition salts.

16. A compound of claim 1 selected from the group consisting of 11β-[4-(2-dimethylaminoethoxy)-phenyl]-Δ$^{1,3,5(10)}$-estratriene-3, 17β-diol, 11β-[4-(2-dimethylaminoethoxy)-phenyl]-Δ$^{1,3,5(10)}$-estratriene-17β-ol, 3-(2-dimethylaminoethoxy)-11β-phenyl-Δ$^{1,3,5(10)}$-estratriene-17β-ol and their non-toxic, pharmaceutically acceptable acid addition salts.

17. A compound of the formula

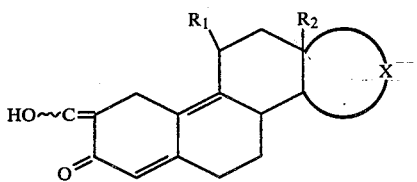

wherein $R_1$, $R_2$ and X have the definition of claim 1.

18. An antiglucocorticoidal composition comprising an antiglucocorticoidally effective amount of at least one compound of claim 1 and an inert pharmaceutical carrier.

19. A composition of claim 18 wherein X is

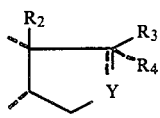

wherein $R_2$ has the definition of claim 1, the dotted line in the 16,17-position indicates an optional double bond, Y is

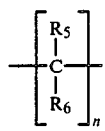

n is 1 or 2, $R_5$ is selected from the group consisting of hydrogen, alkyl of 1 to 8 carbon atoms, alkenyl and alkynyl of 2 to 8 carbon atoms, aryl of 6 to 14 carbon atoms and aralkyl of 7 to 15 carbon atoms, $R_6$ is selected from the group consisting of hydrogen, —OH, alkyl of 1 to 8 carbon atoms, alkenyl and alkynyl of 2 to 8 carbon atoms, aryl of 6 to 14 carbon atoms and aralkyl of 7 to 15 carbon atoms and $R_3$ and $R_4$ are individually selected from the group consisting of hydrogen, —OH, —OAlK$_4$,

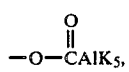

alkenyl and alkynyl of 2 to 8 carbon atoms,

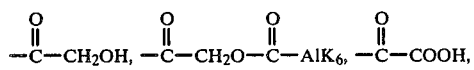

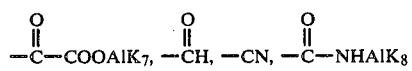

or $R_3$ and $R_4$ together with the carbon atoms are

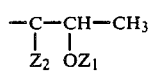

or

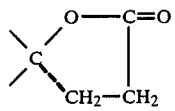

AlK$_4$, AlK$_5$ and AlK$_8$ are selected from the group consisting of alkyl of 1 to 8 carbon atoms and aralkyl of 7 to 15 carbon atoms, AlK$_6$ are selected from the group consisting of alkyl of 1 to 8 carbon atoms, optionally susbituted and aralkyl of 7 to 15 carbon atoms, AlK$_7$ and $Z_2$ are alkyl of 1 to 8 carbon atoms and $Z_1$ is selected from the group consisting of hydrogen, alkyl of 1 to 8 carbon atoms and acyl of 1 to 8 carbon atoms.

20. A composition of claim 18 wherein the D ring does not contain unsaturation, n is 1 and $R_5$ and $R_6$ are hydrogen.

21. A composition of claim 18 wherein $R_3$ is —OH or

AlK$_5$ is alkyl of 1 to 8 carbon atoms or aralkyl of 7 to 15 carbon atoms and $R_4$ is alkenyl or alkynyl of 2 to 4 carbon atoms.

22. A composition of claim 18 wherein $R_1$ is aryl or aralkyl carrying an amino of the formula

wherein $R_7$ and $R_8$ are alkyl of 1 to 8 carbon atoms or primary, secondary or tertiary alkyl of 1 to 8 carbon atoms containing at least one heteroatom of the group consisting of —O—, —S— or —N— with at least one being nitrogen or substituted with a heterocycle containing at least one nitrogen atom.

23. A composition of claim 18 wherein $R_1$ is selected from the group consisting of 2-pyridyl, 3-pyridyl and 4-pyridyl,

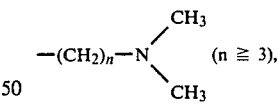

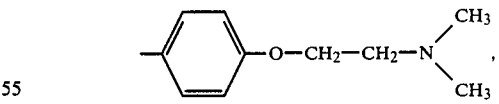

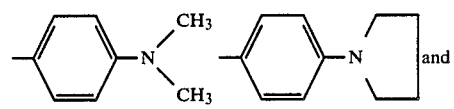 and

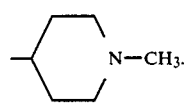

24. A composition of claim 18 wherein $R_1$ is selected from the group consisting of thienyl, furyl, cycloalkyl of 3 to 6 carbon atoms and phenyl optionally substituted with at least one member of the group consisting of —OH, halogen, —CF$_3$, alkyl and alkoxy of 1 to 8 carbon atoms and alkylthio of 1 to 8 carbon atoms optionally oxidized to sulfoxide or sulfone and A and B rings are not

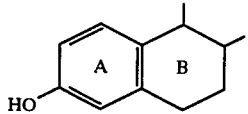

25. A composition of claim 18 wherein R$_1$ is phenyl substituted with a member of the group consisting of chlorine, fluorine, methylthio, methylsulfonyl, methoxy, —OH and allyloxy.

26. A composition of claim 18 wherein the A and B rings are:

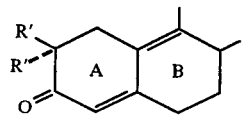

wherein R' and R" are both methyl or both —CN or one is hydrogen and the other is methyl or —CN.

27. A composition of claim 18 wherein A and B are

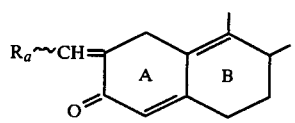

wherein R$_a$ is morpholino or acetoxy.

28. A method of inducing antiglucocorticoidal activity in warm-blooded animals comprising administering to warm-blooded animals an antiglucocorticoidally effective amount of at least one compound of claim 1.

29. A method of claim 28 wherein X is

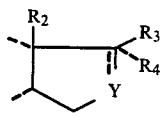

wherein R$_2$ has the definition of claim 1, the dotted line in the 16,17-position indicates an optional double bond, Y is

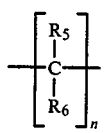

n is 1 or 2, R$_5$ is selected from the group consisting of hydrogen, alkyl of 1 to 8 carbon atoms, alkenyl and alkynyl of 2 to 8 carbon atoms, aryl of 6 to 14 carbon atoms and aralkyl of 7 to 15 carbon atoms, R$_6$ is selected from the group consisting of hydrogen, —OH, alkyl of 1 to 8 carbon atoms, alkenyl and alkynyl of 2 to 8 carbon atoms, aryl of 6 to 14 carbon atoms and aralkyl of 7 to 15 carbon atoms and R$_3$ and R$_4$ are individually selected from the group consisting of hydrogen, —OH, —OAlK$_4$,

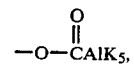

alkenyl and alkynyl of 2 to 8 carbon atoms,

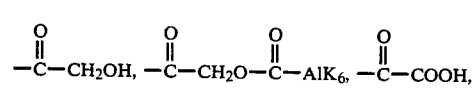

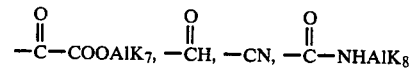

or R$_3$ and R$_4$ together with the carbon atoms are

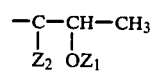

or

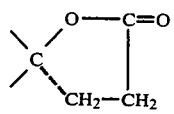

AlK$_4$, AlK$_6$ and AlK$_8$ are selected from the group consisting of alkyl of 1 to 8 carbon atoms and aralkyl of 7 to 15 carbon atoms, AlK$_6$ are selected from the group consisting of alkyl 1 to 8 carbon atoms optionally substitued and aralkyl of 7 to 15 carbon atoms, AlK$_7$ and Z$_2$ are alkyl of 1 to 8 caron atoms and Z$_1$ is selected from the group consisting of hydrogen, alkyl of 1 to 8 carbon atoms and acyl of 1 to 8 carbon atoms.

30. A method of claim 28 wherein the D ring does not contain unsaturation, n is 1 and R$_5$ and R$_6$ are hydrogen.

31. A method of claim 28 wherein R$_3$ is —OH or

AlK$_5$ is alkyl of 1 to 8 carbon atoms or aralkyl of 7 to 15 carbon atoms and R$_4$ is alkenyl or alkynyl of 2 to 4 carbon atoms.

32. A method of claim 28 wherein R$_1$ is aryl or aralkyl carrying an amino of the formula

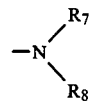

wherein R$_7$ and R$_8$ are alkyl of 1 to 8 carbon atoms or primary, secondary or tertiary alkyl of 1 to 8 carbon atoms containing at least one heteroatom of the group consisting of —O—, —S— or —N— with at least one being nitrogen or substituted with a heterocycle containing at least one nitrogen atom.

33. A method of claim 28 wherein R$_1$ is selected from the group consisting of 2-pyridyl, 3-pyridyl and 4-pyridyl,

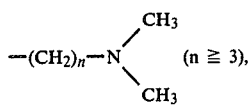

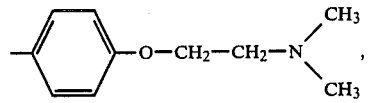

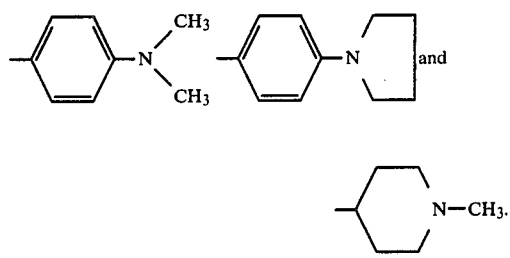

34. A method of claim 28 and wherein $R_1$ is selected from the group consisting of thienyl, furyl, cycloalkyl of 3 to 6 carbon atoms and phenyl optionally substituted with at least one member of the group consisting of —OH, halogen, —CF$_3$, alkyl and alkoxy of 1 to 8 carbon atoms and alkylthio of 1 to 8 carbon atoms optionally oxidized to sulfoxide or sulfone and A and B rings are not

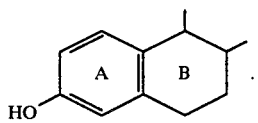

35. A method of claim 28 wherein $R_1$ is phenyl substituted with a member of the group consisting of chlorine, fluorine, methylthio, methylsulfonyl, methoxy, —OH and allyloxy.

36. A method of claim 28 wherein the A and B rings are

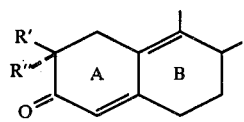

wherein R' and R" are both methyl or both —CN or one is hydrogen and the other is methyl or —CN.

37. A method of claim 28 wherein A and B are

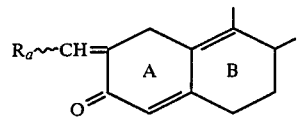

wherein $R_a$ is morpholino or acetoxy.

38. A method of claim 28 wherein the compound is selected from the group consisting of 2,2-dimethyl-11β-(4-dimethylaminophenyl)-17α-(prop-1-ynyl)-Δ$^{4,9}$-estradiene-17β-ol-3-one, 2,2-dicyano-11β-(4-dimethylaminophenyl)-17α-(prop-1-ynyl)-Δ$^{4,9}$-estradiene-17β-ol-3-one, 2α-methyl-11β-(4-dimethylaminophenyl)-17α-(prop-1-ynyl)-Δ$^{4,9}$-estradiene-17β-ol-3-one, 2β-methyl-11β-(4-dimethylaminophenyl)-Δ$^{4,9}$-estradiene-17β-ol-3-one, 2-cyano-11β-(4-dimethylaminophenyl)-17α-(prop-1-ynyl)-Δ$^{4,9}$-estradiene-17β-ol-3-one and their non-toxic, pharmaceutically acceptable acid addition salts.

39. A method of claim 28 wherein the compound is selected from the group consisting of 11β-(4-dimethylaminophenyl)-17α-(prop-1-ynyl)-Δ$^{1,3,5(10)}$-estratriene-3,17β-diol, 11β-(4-dimethylaminophenyl)-17β-acetoxy-17α-(prop-1-ynyl)-Δ$^{1,3,5(10)}$-estratriene-3-ol, 3-methoxy-11β-(4-dimethylaminophenyl)-17α-(prop-1-ynyl)-Δ$^{1,3,5(10)}$-estratriene-17β-ol, 3-methoxy-11β-(4-dimethylaminophenyl)-17β-acetoxy-17α-(prop-1-ynyl)-Δ$^{1,3,5(10)}$-estratriene and their non-toxic, pharmaceutically acceptable acid addition salts.

40. A metuod of claim 28 wherein the compound is selected from the group consisting of 11β-(3-methoxyphenyl)-17α-(prop-1-ynyl)-Δ$^{5(10)}$-estrene-17β-ol-3-one, E isomer of 11β-(3-methoxyphenyl)-17α-(prop-1-enyl)-Δ$^{5(10)}$-estrene-17β-ol-3-one, 11β-(4-dimethylaminophenyl)-17α-(prop-1-ynyl)-Δ$^{5(10)}$-estrene-17β-ol-3-one and its non-toxic, pharmaceutically acceptable acid addition salts.

41. A method of claim 28 wherein the compound is selected from the group consisting of 2-(acetyloxy methylene)-11β-(4-dimethylaminophenyl)-17α-(prop-1-ynyl)-Δ$^{4,9}$-estradiene-17β-ol-3-one, 2-(4-morpholinomethylene)-11β-(4-dimethylaminophenyl)-17α-(prop-1-ynyl)-Δ$^{4,9}$-estradiene-17β-ol-3-one and their non-toxic, pharmaceutically acceptable acid addition salts.

42. A method of claim 28 wherein the compound is selected from the group consisting of 11β-(4-dimethylaminophenyl)-17α-(prop-1-ynyl)-isoxazolo[4,5-b]-Δ$^{4,9}$-estradiene-17β-ol and its non-toxic, pharmaceutically acceptable acid addition salts.

43. A method of claim of claim 28 wherein the compound is selected from the group consisting of 11β-[4-(2-dimethylaminoethoxy)-phenyl]-Δ$^{1,3,5(10)}$-estratriene-3,17β-diol, 11β-[4-(2-dimethylaminoethoxy)-phenyl]-Δ$^{1,3,5(10)}$-estratriene-17β-ol, 3-(2-dimethylaminoethoxy)-11β-phenyl-Δ$^{1,3,5(10)}$-estratriene-17β-ol and their non-toxic, pharmaceutically acceptable acid addition salts.

44. A method of inducing contraception or interruption of pregnancy in warm-blooded animals comprising administering to female warm-blooded animals a sufficient amount of at least one compound of claim 1 to interrupt pregnancy or to induce contraception.

* * * * *

UNITED STATES PATENT AND TRADEMARK OFFICE
CERTIFICATE OF CORRECTION

PATENT NO. : 4,547,493

DATED : Oct. 15, 1985

INVENTOR(S) : JEAN-GEORGES TEUTSCH, VESPERTO TORELLI, ROGER DERAEDT, DANIEL PHILIBERT

It is certified that error appears in the above-identified patent and that said Letters Patent are hereby corrected as shown below:

| Col. | Line | | |
|---|---|---|---|
| [57] | Formula (a) | " 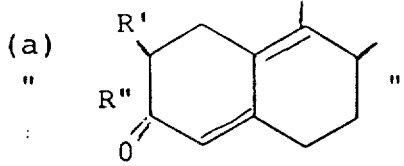 " | should be 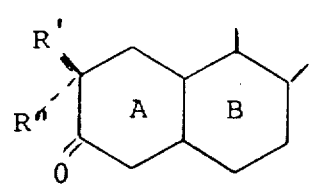 |
| 6 | 10 | "(n ≩ 3)" should be --(n ≧ 3)-- | |
| 7 | 26 | "17β" should be --17α -- | |
| 13 | 35 | "17β-ol3-one" should be --17β-ol-3-one.-- | |
| 13 | 50 | "Δ5(10)-estrene" should be --Δ$^{5(10)}$-estrene-- | |
| 25 | Col. 1 | | should be |
| | | " 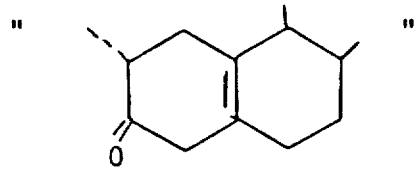 " | -- 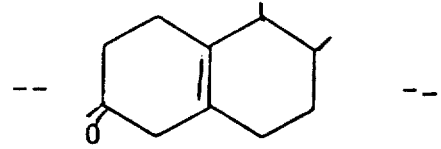 -- |

UNITED STATES PATENT AND TRADEMARK OFFICE
CERTIFICATE OF CORRECTION

PATENT NO. : 4,547,493

DATED : Oct. 15, 1985

INVENTOR(S) : JEAN-GEORGES TEUTSCH, VESPERTO TORELLI, ROGER DERAEDT, DANIEL PHILIBERT

It is certified that error appears in the above-identified patent and that said Letters Patent are hereby corrected as shown below:

| Col. | Line |  |  |  |
|---|---|---|---|---|
| 49 | Col. 2 | 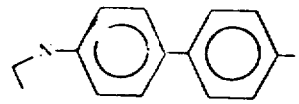 |  | 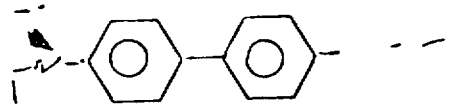 |
| 51 | " | " |  | " |
| 53 | " | " |  | " |
| 55 | " | " |  | " |
| 61 | Col. 1 | 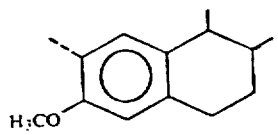 | should be | 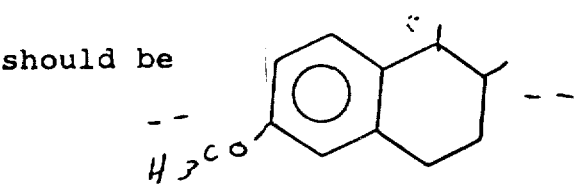 |
| " | " | " |  | " |
| 69 | " | 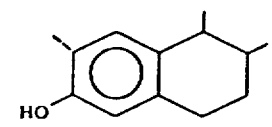 | should be | 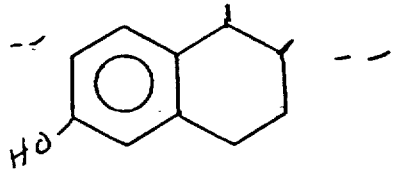 |
| " | " | " |  | " |
| 71 | " | " |  | " |

UNITED STATES PATENT AND TRADEMARK OFFICE
CERTIFICATE OF CORRECTION

PATENT NO. : 4,547,493

DATED : Oct. 15, 1985

Page 3 of 5

INVENTOR(S) : JEAN-GEORGES TEUTSCH, VESPERTO TORELLI, ROGER DERAEDT, DANIEL PHILIBERT

It is certified that error appears in the above-identified patent and that said Letters Patent are hereby corrected as shown below:

| Col. | Line |
|------|------|
| 71   | Col. 1 |
| 73   | "    |
| 73   | "    |
| 73   | "    |
| 77   | "    |
| 77   | "    |
| 79   | "    |
| 79   | "    |
| 81   | "    |

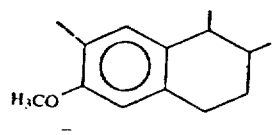 should be 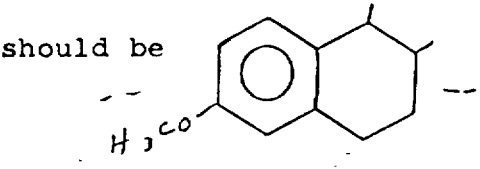

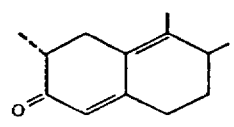 should be 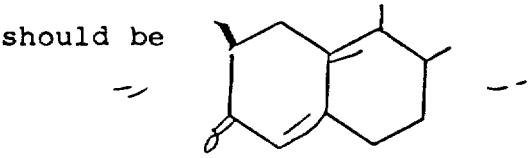

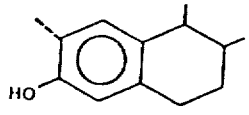 should be 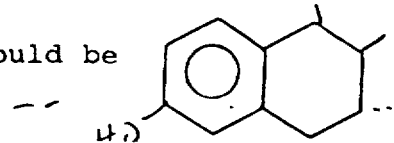

UNITED STATES PATENT AND TRADEMARK OFFICE
CERTIFICATE OF CORRECTION

PATENT NO. : 4,547,493

DATED : Oct. 15, 1985

INVENTOR(S) : JEAN-GEORGES TEUTSCH, VESPERTO TORELLI, ROGER DERAEDT, DANIEL PHILIBERT

It is certified that error appears in the above-identified patent and that said Letters Patent are hereby corrected as shown below:

| Col. | Line |
|------|------|
| 81 | Col. 1 |

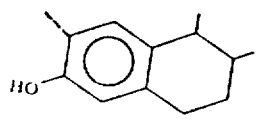 should be

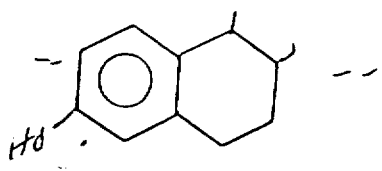

| 81 | " |
| " | " |
| 83 | " |

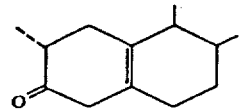 should be 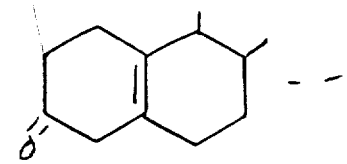

| 83 | " | " " | " " |
| 85 | " | " " | " " |
| 85 | " | " | " " |
| 87 | " | | |

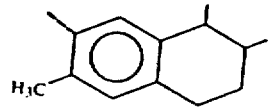 should be 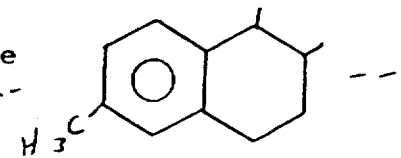

| 89 | | | |
| " | " | " " | " " |
| " | " | " " | " " |
| " | " | " " | " " |
| 91 | " | " " | " " |

UNITED STATES PATENT AND TRADEMARK OFFICE
CERTIFICATE OF CORRECTION

PATENT NO. : 4,547,493

DATED : Oct. 15, 1985

INVENTOR(S) : JEAN-GEORGES TEUTSCH, VESPERTO TORELLI, ROGER DERAEDT, DANIEL PHILIBERT

It is certified that error appears in the above-identified patent and that said Letters Patent are hereby corrected as shown below:

| Col. | Line | |
|---|---|---|
| 117 | Col. 1 | Insert --Example 1-- |
| 117 | 37 | " $-66^{4-9}$ " should be $--\Delta^{4,9}--$ |
| 120 | 57 | "95.1" should be --95.5-- |
| 133 | Claim 6 | "(n ⪈ 3)" should be --(n ≥ 3)-- |
| 135 | Claim 19 | 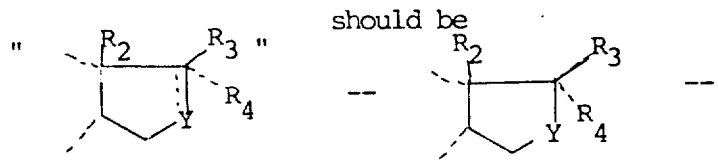 |
| 136 | claim 23 | "(n ⪈3)" should be -- (n ≥3)-- |
| 139 | Claim 33 | " " " |

Signed and Sealed this

Eighth Day of April 1986

[SEAL]

Attest:

DONALD J. QUIGG

Attesting Officer     Commissioner of Patents and Trademarks